US012655206B2

(12) United States Patent
Hsia et al.

(10) Patent No.: US 12,655,206 B2
(45) Date of Patent: *Jun. 16, 2026

(54) METHOD OF TREATING PSORIATIC ARTHRITIS PATIENTS WITH INADEQUATE RESPONSE TO TNF THERAPY WITH ANTI-IL23 SPECIFIC ANTIBODY

(71) Applicant: Janssen Biotech, Inc., Horsham, PA (US)

(72) Inventors: Elizabeth Hsia, Kennett Square, PA (US); Chetan Karyekar, Horsham, PA (US); Alexa Kollmeier, San Diego, CA (US); Wim Noel, Flemish Brabant (BE); Jaime Oliver Vigueras, Zug (CH); Agata Schubert-Wlodarczyk, Warsaw (PL); May Shawi, Horsham, PA (US); Virginia Taliadouros, Leiden (NL); Xie Xu, San Diego, CA (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/691,219

(22) Filed: Mar. 10, 2022

(65) Prior Publication Data

US 2022/0289834 A1     Sep. 15, 2022

Related U.S. Application Data

(60) Provisional application No. 63/188,707, filed on May 14, 2021, provisional application No. 63/160,078, filed on Mar. 12, 2021.

(51) Int. Cl.
| | |
|---|---|
| *A61K 39/00* | (2006.01) |
| *A61P 19/02* | (2006.01) |
| *A61P 37/06* | (2006.01) |
| *C07K 16/24* | (2006.01) |

(52) U.S. Cl.
CPC ........... *C07K 16/244* (2013.01); *A61P 19/02* (2018.01); *A61P 37/06* (2018.01); *C07K 16/241* (2013.01); *A61K 2039/505* (2013.01); *A61K 2039/545* (2013.01); *C07K 2317/76* (2013.01)

(58) Field of Classification Search
CPC .................... A61K 39/395; A61K 2039/55522
See application file for complete search history.

(56) References Cited

U.S. PATENT DOCUMENTS

| | | |
|---|---|---|
| 4,309,989 A | 1/1982 | Fahim |
| 4,399,216 A | 8/1983 | Axel |
| 4,589,330 A | 5/1986 | Teron |
| 4,634,665 A | 1/1987 | Axel |
| 4,656,134 A | 4/1987 | Ringold |
| 4,676,980 A | 6/1987 | Segal |
| 4,683,195 A | 7/1987 | Mullis |
| 4,683,202 A | 7/1987 | Mullis |
| 4,704,692 A | 11/1987 | Ladner |
| 4,766,067 A | 8/1988 | Biswas |
| 4,767,402 A | 8/1988 | Kost |
| 4,795,699 A | 1/1989 | Tabor |
| 4,800,159 A | 1/1989 | Mullis |
| 4,816,567 A | 3/1989 | Cabilly |
| 4,818,542 A | 4/1989 | Deluca |
| 4,873,316 A | 10/1989 | Meade |
| 4,889,818 A | 12/1989 | Gelfand |
| 4,921,794 A | 5/1990 | Tabor |
| 4,939,666 A | 7/1990 | Hardman |
| 4,946,778 A | 8/1990 | Ladner |
| 4,956,288 A | 9/1990 | Barsoum |
| 4,965,188 A | 10/1990 | Mullis |
| 4,994,370 A | 2/1991 | Silver |
| 5,066,584 A | 11/1991 | Gyllensten |
| 5,091,310 A | 2/1992 | Innis |
| 5,122,464 A | 6/1992 | Wilson |
| 5,130,238 A | 7/1992 | Malek |
| 5,142,033 A | 8/1992 | Innis |
| 5,149,636 A | 9/1992 | Axel |
| 5,168,062 A | 12/1992 | Stinski |
| 5,179,017 A | 1/1993 | Axel |
| 5,223,409 A | 6/1993 | Ladner |
| 5,225,539 A | 7/1993 | Winter |
| 5,260,203 A | 11/1993 | Ladner |
| 5,266,491 A | 11/1993 | Nagata |
| 5,304,489 A | 4/1994 | Rosen |

(Continued)

FOREIGN PATENT DOCUMENTS

| | | |
|---|---|---|
| EP | 0003089 B1 | 8/1981 |
| EP | 0229246 | 7/1987 |

(Continued)

OTHER PUBLICATIONS

US 5,733,746 A, 03/1998, Treco (withdrawn)

(Continued)

*Primary Examiner* — Prema M Mertz

(74) *Attorney, Agent, or Firm* — Ice Miller LLP

(57)     ABSTRACT

A method of treating psoriatic arthritis in a patient having showed an inadequate response to treatment with an anti-TNF therapy by administering an IL-23 specific antibody, e.g., guselkumab, in a clinically proven safe and clinically proven effective amount and the patient achieves significant ACR20/50/70, IGA, HAQ-DI, CRP, SF-36 PCS/MCS, MDA, VLDA, enthesitis, dactylitis, and LEI/dactylitis improvement as measured 16, 24 and 48 weeks after initial treatment.

34 Claims, 1 Drawing Sheet

Specification includes a Sequence Listing.

(56) References Cited

U.S. PATENT DOCUMENTS

| | | | |
|---|---|---|---|
| 5,385,839 A | 1/1995 | Stinski | |
| 5,403,484 A | 4/1995 | Ladner | |
| 5,427,908 A | 6/1995 | Dower | |
| 5,455,030 A | 10/1995 | Ladner | |
| 5,496,549 A | 3/1996 | Yamazaki | |
| 5,518,889 A | 5/1996 | Ladner | |
| 5,530,101 A | 6/1996 | Queen | |
| 5,534,621 A | 7/1996 | Ladner | |
| 5,545,806 A | 8/1996 | Lonberg | |
| 5,545,807 A | 8/1996 | Surani | |
| 5,565,362 A | 10/1996 | Rosen | |
| 5,569,825 A | 10/1996 | Lonberg | |
| 5,571,698 A | 11/1996 | Ladner | |
| 5,576,195 A | 11/1996 | Robinson | |
| 5,580,717 A | 12/1996 | Dower | |
| 5,580,734 A | 12/1996 | Treco | |
| 5,582,996 A | 12/1996 | Curtis | |
| 5,585,089 A | 12/1996 | Queen | |
| 5,595,898 A | 1/1997 | Robinson | |
| 5,601,819 A | 2/1997 | Wong | |
| 5,618,920 A | 4/1997 | Robinson | |
| 5,625,126 A | 4/1997 | Lonberg | |
| 5,625,825 A | 4/1997 | Rostoker | |
| 5,627,052 A | 5/1997 | Schrader | |
| 5,633,425 A | 5/1997 | Lonberg | |
| 5,641,670 A | 6/1997 | Treco | |
| 5,643,759 A | 7/1997 | Pfreundschuh | |
| 5,643,768 A | 7/1997 | Kawasaki | |
| 5,656,730 A | 8/1997 | Lee | |
| 5,658,754 A | 8/1997 | Kawasaki | |
| 5,661,016 A | 8/1997 | Lonberg | |
| 5,693,493 A | 12/1997 | Robinson | |
| 5,693,762 A | 12/1997 | Queen | |
| 5,698,417 A | 12/1997 | Robinson | |
| 5,698,435 A | 12/1997 | Robinson | |
| 5,714,352 A | 2/1998 | Jakobovits | |
| 5,723,323 A | 3/1998 | Kauffman | |
| 5,733,761 A | 3/1998 | Treco | |
| 5,750,373 A | 5/1998 | Garrard | |
| 5,763,192 A | 6/1998 | Kauffman | |
| 5,763,733 A | 6/1998 | Whitlow | |
| 5,766,886 A | 6/1998 | Studnicka | |
| 5,767,260 A | 6/1998 | Whitlow | |
| 5,770,359 A | 6/1998 | Wilson | |
| 5,770,428 A | 6/1998 | Boris-Lawrie | |
| 5,789,650 A | 8/1998 | Lonberg | |
| 5,807,706 A | 9/1998 | Carter | |
| 5,814,476 A | 9/1998 | Kauffman | |
| 5,817,483 A | 10/1998 | Kauffman | |
| 5,821,333 A | 10/1998 | Carter | |
| 5,824,514 A | 10/1998 | Kauffman | |
| 5,827,690 A | 10/1998 | Meade | |
| 5,827,739 A | 10/1998 | Wilson | |
| 5,833,985 A | 11/1998 | Ball | |
| 5,837,500 A | 11/1998 | Ladner | |
| 5,839,446 A | 11/1998 | Waner | |
| 5,849,992 A | 12/1998 | Meade | |
| 5,851,198 A | 12/1998 | Castellano | |
| 5,856,456 A | 1/1999 | Whitlow | |
| 5,885,793 A | 3/1999 | Griffiths | |
| 5,932,448 A | 8/1999 | Tso | |
| 5,959,083 A | 9/1999 | Bosslet | |
| 5,959,084 A | 9/1999 | Ring | |
| 5,976,862 A | 11/1999 | Kauffman | |
| 5,989,530 A | 11/1999 | Lorenz | |
| 5,994,616 A | 11/1999 | Rosen | |
| 6,010,902 A | 1/2000 | Ledbetter | |
| 6,019,968 A | 2/2000 | Platz | |
| 6,037,453 A | 3/2000 | Jardieu | |
| 6,060,285 A | 5/2000 | Lenz | |
| 6,106,833 A | 8/2000 | Ring | |
| 6,132,992 A | 10/2000 | Ledbetter | |
| 6,180,370 B1 | 1/2001 | Queen | |
| 6,193,967 B1 | 2/2001 | Morganelli | |
| 6,204,023 B1 | 3/2001 | Robinson | |
| 6,210,668 B1 | 4/2001 | Lindhofer | |
| 7,935,344 B2 * | 5/2011 | Benson | A61P 35/00 424/145.1 |
| 7,993,645 B2 * | 8/2011 | Benson | A61P 17/06 424/145.1 |
| 8,221,760 B2 * | 7/2012 | Benson | A61K 9/0019 424/133.1 |
| 8,722,033 B2 | 5/2014 | Towne et al. | |
| 9,783,607 B2 * | 10/2017 | Benson | A61P 37/00 |
| 10,030,070 B2 * | 7/2018 | Benson | A61P 17/06 |
| 11,548,941 B2 | 1/2023 | Angsana et al. | |
| 2003/0003097 A1 | 1/2003 | Reff | |
| 2004/0161816 A1 | 8/2004 | Kauffman | |
| 2011/0206680 A1 | 8/2011 | Valdes | |
| 2015/0064193 A1 * | 3/2015 | Wang | A61P 19/02 424/142.1 |
| 2015/0147337 A1 * | 5/2015 | Reichert | A61K 39/39591 424/145.1 |
| 2017/0281762 A1 | 10/2017 | Mpofu et al. | |
| 2018/0094052 A1 | 4/2018 | Randazzo et al. | |
| 2018/0134784 A1 | 5/2018 | Fitzgerald et al. | |
| 2019/0135910 A1 | 5/2019 | Hsia | |
| 2020/0095315 A1 | 3/2020 | Johans et al. | |
| 2020/0369761 A1 | 11/2020 | Germinaro et al. | |
| 2020/0385453 A1 | 12/2020 | Hsia | |
| 2021/0347880 A1 | 11/2021 | Adedokun et al. | |
| 2021/0363234 A1 | 11/2021 | Germinaro et al. | |
| 2021/0363235 A1 | 11/2021 | Hsia et al. | |
| 2022/0025035 A1 | 1/2022 | Hsia et al. | |
| 2022/0298236 A1 | 9/2022 | Hsia et al. | |
| 2025/0304674 A1 | 10/2025 | Baum et al. | |

FOREIGN PATENT DOCUMENTS

| | | | |
|---|---|---|---|
| EP | 368684 | | 5/1990 |
| EP | 0438474 | | 7/1991 |
| EP | 0463151 | | 1/1992 |
| EP | 550400 | | 7/1993 |
| EP | 0710719 | | 5/1996 |
| EP | 0814259 | | 12/1997 |
| EP | 371998 | | 1/2005 |
| GB | 2272440 | | 5/1994 |
| WO | 8605803 | | 10/1986 |
| WO | 8806630 | | 9/1988 |
| WO | 8906283 | | 7/1989 |
| WO | 9004036 | A1 | 4/1990 |
| WO | 9005370 | | 5/1990 |
| WO | 1990005370 | | 5/1990 |
| WO | 1990014424 | | 11/1990 |
| WO | 1990014430 | | 11/1990 |
| WO | 1990014443 | | 11/1990 |
| WO | 9100360 | | 1/1991 |
| WO | 1991017271 | | 11/1991 |
| WO | 9118980 | | 12/1991 |
| WO | 9119818 | | 12/1991 |
| WO | 9200373 | | 1/1992 |
| WO | 9201047 | A1 | 1/1992 |
| WO | 1992001047 | | 1/1992 |
| WO | 1992003461 | | 3/1992 |
| WO | 9205258 | | 4/1992 |
| WO | 9206204 | | 4/1992 |
| WO | 1992011272 | | 7/1992 |
| WO | 9214843 | | 9/1992 |
| WO | 9218619 | | 10/1992 |
| WO | 1992016221 | A1 | 10/1992 |
| WO | 9220791 | | 11/1992 |
| WO | 9308278 | | 4/1993 |
| WO | 1993006213 | | 4/1993 |
| WO | 9308829 | | 5/1993 |
| WO | 9311236 | | 6/1993 |
| WO | 9319172 | | 9/1993 |
| WO | 1994018219 | | 8/1994 |
| WO | 9425585 | | 11/1994 |
| WO | 9501438 | | 1/1995 |
| WO | 9515388 | A1 | 6/1995 |
| WO | 9516027 | | 6/1995 |
| WO | 9607754 | | 3/1996 |
| WO | 9613583 | | 5/1996 |

(56) References Cited

FOREIGN PATENT DOCUMENTS

| | | |
|---|---|---|
| WO | 9619256 | 6/1996 |
| WO | 9634096 | 10/1996 |
| WO | 9708320 | 3/1997 |
| WO | 9713852 | 4/1997 |
| WO | 1997020032 | 6/1997 |
| WO | 9801757 | 1/1998 |
| WO | 9824884 | 6/1998 |
| WO | 9824893 | 6/1998 |
| WO | 9850433 | 11/1998 |
| WO | 9853847 | 12/1998 |
| WO | 9906834 | 2/1999 |
| WO | 9916419 | 4/1999 |
| WO | 9954342 | 10/1999 |
| WO | 0042072 | 7/2000 |
| WO | 03011878 | 2/2003 |
| WO | 2015119841 A1 | 8/2015 |
| WO | 2017172771 A2 | 10/2017 |
| WO | 2018140121 A1 | 8/2018 |
| WO | WO 2018218215 A1 * | 11/2018 ......... A61K 39/3955 |
| WO | 2019224283 A1 | 11/2019 |
| WO | 2022190034 | 9/2022 |

OTHER PUBLICATIONS

Coates et al Ann Rheum Dis 2022, 81:359-369.*
Mantravadi et al (2017). Expert Rev Clin Pharmacol. 10(8): 899-910.*
Clinical Trial NCT03158285 (May 18, 2017).*
Delaunay et al (2005), Journal of Rheumatology, 32(11), pp. 2183-2185.*
Kilic et al. (2012), Rheumatol Int, 32:2675-2679.*
Chimenti et al. (2013) Dermatology, 227:305-310.*
Wofford et al. (2014), Expert Rev. Clin. Immunol. 10(2):189-202.*
NCT02319759, (Dec. 18, 2014), NIH, US National Library of Medicine, ClinicalTrials.gov.*
Babcook, John S. et al. "A novel strategy for generating monoclonal antibodies from single, isolated lymphocytes producing antibodies of defined specificities," Proceedings of the National Academy of Sciences of the United States of America, vol. 93 (Jul. 1996) pp. 7843-7848.
Carter, Paul et al., "Humanization of an Anti-P185HER2 Antibody for Human Cancer therapy," Proceedings of the National Academy of Sciences of the United States of America, vol. 89, issue 10 (May 15, 1992) pp. 4285-4289.
Chothia et al., "Canonical Structures for the Hypervariable Regions of Immunoglobulins," Journal of Molecular Biology, vol. 196, issue 4 (Aug. 20, 1987) pp. 901-917.
Conrad, Udo et al. "Compartment-specific accumulation of recombinant immunoglobulins in plant cells: an essential tool for antibody production and immunomodulation of physiological functions and pathogen activity," Plant Molecular Biology, vol. 38 (1998) pp. 101-109.
Cramer, C. L. et al. "Transgenic Plants for Therapeutic Proteins: Linking Upstream and Downstream Strategies," Plant Biotechnology, vol. 240 (2000) pp. 95-118.
Deodhar, Atul et al., "Guselkumab in patients with active psoriatic arthritis who were biologic-naive or had previously received TNF(alpha) inhibitor treatment (Discover-1): a double-blind, randomised, placebo-controlled phase 3 trial," The Lancet, vol. 395 (Apr. 2020) pp. 1115-1125.
Elliott, M.J. et al. "Repeated therapy with monoclonal antibody to tumour necrosis factor α (cA2) in patients with rheumatoid arthritis," The Lancet, vol. 344, issue 8930 (Oct. 1994) pp. 1125-1127.
Eren, Lubin R. et at. "Human monoclonal antibodies specific to hepatitis B virus generated in a human/mouse radiation chimera: The Trimera system," Immunology, vol. 93, issue 2 (Feb. 2008) pp. 154-161.
Felson et al., "American College of Rheumatology Preliminary Definition of Improvement in Rheumatoid Arthritis," Arthritis and Rheumatism, 1995, 38(6):727-735.

Fischer, Rainer et al. "Towards molecular farming in the future: transient protein expression in plants," Biotechnology and Applied Biochemistry, vol. 30, issue 2 (Oct. 1999) pp. 113-116.
Fishwild, Dianne M. et al. "High-avidity human IgGK monoclonal antibodies from a novel strain of minilocus transgenic mice," Nature Biotechnology, vol. 14 (1996) pp. 845-851.
Gray, Forest et al. "Secretion capture and report web: use of affinity derivatized agarose microdroplets for the selection of hybridoma cells," Journal of Immunological Methods, vol. 182, issue 2 (Jun. 1995) pp. 155-163.
Green, L. L. et al. "Antigen-specific human monoclonal antibodies from mice engineered with human Ig heavy and light chain YACs," Nature Genetics, vol. 7 (1994) pp. 13-21.
Hanes et al, "In vitro selection and evolution of functional proteins by using ribosome display," Proceedings of the National Academy of Sciences USA, vol. 94, pp. 4937-4942 (1997).
Hanes, Jozef et al. "Ribosome display efficiently selects and evolves high-affinity antibodies in vitro from immune libraries," Proceedings of the National Academy of Sciences of the United States of America, vol. 95 (Nov. 1998) pp. 14130-14135.
Hood, Elizabeth E. et al. "Molecular Farming of Industrial Proteins from Transgenic Maize," Chemicals via Higher Plant Bioengineering (Advances in Experimental Medicine and Biology), vol. 464(1999) pp. 127-147.
International Search Report and Written Opinion issued in App. No. PCT/IB2022/52163, dated Jun. 22, 2022, 12 pages.
Jones, Peter T. "Replacing the complementarity-determining regions in a human antibody with those from a mouse," Nature, vol. 321 (1986) pp. 522-525.
Kenney, John S. et al. "Production of Monoclonal Antibodies Using a Secretion Capture Report Web," Nature Biotechnology, vol. 13 (1995) pp. 787-790.
Ki-Wei, Tan et al. "Novel systemic therapies for the treatment of psoriasis", Expert Opinion on Pharmacotherapy, vol. 17, issue 1 (2016) pp. 79-92.
Lonberg, Nils et al. Antigen-specific human antibodies from mice comprising four distinct genetic modifications, Nature, vol. 368 (1994) pp. 856-859.
Lonberg, Nils et al. "Human Antibodies from Transgenic Mice," International Reviews of Immunology, vol. 13, issue 1 (1995) pp. 65-93.
Lonberg, Nils, "Human antibodies from transgenic animals," Nature Biotechnology, vol. 23 (2005) pp. 1117-1125.
Ma, Julian K-C et al. "Plant Antibodies for Immunotherapy ," Plant Physiology, vol. 109 (1995) pp. 341-346.
Ma, Julian K-C et al. "Immunotherapeutic potential of antibodies produced in plants," Trends in Biotechnology, vol. 13, issue 12 (Dec. 1995) pp. 522-527.
Mease, Philip J. et al. "Guselkumab, an Anti-interleukin-23p19 Monoclonal Antibody, in Biologic-naive Patients with Active Psoriatic Arthritis: Week 24 Results of the Phase 3, Randomized, Double-blind, Placebo-controlled Study," Abstract No. L13 (Oct. 2019) pp. 1-5.
Mendez, Michael J. et al. "Functional transplant of megabase human immunoglobulin loci recapitulates human antibody response in mice," Nature Genetics, vol. 15 (1997) pp. 146-156.
Milstein, C. et al. "Hybrid hybridomas and their use in immunohistochemistry," Nature, vol. 305 (1983) pp. 537-540.
Nguyen, Hai et al. "Production of Human Monoclonal Antibodies in SCID Mouse," Microbiology and Immunology, vol. 41, issue 12 (1997) pp. 901-907.
Powell, Kevin T. et al. "Gel Microdroplets and Flow Cytometry: Rapid Determination of Antibody Secretion by Individual Cells Within a Cell Population," Biotechnology, vol. 8 (1990) pp. 333-337.
Presta, L.G. et al., "Humanization of an Antibody Directed Against IgE," The Journal of Immunology, vol. 151, issue 5 (Sep. 1, 1993) pp. 2623-2632.
Riechmann, Lutz et al. "Reshaping human antibodies for therapy," vol. 332 (1988) pp. 323-327.
Sandhu, J. S. et al. "The Use of SCID Mice in Biotechnology and as a Model for Human Disease," Critical Reviews in Biotechnology, vol. 16, issue 1 (1996) pp. 95-118.

(56) References Cited

OTHER PUBLICATIONS

Shield, Robert L. et al. "High Resolution Mapping of the Binding Site on Human IgG1 for FcγRI, FcγRII, FcγRIII, and FcRn and Design of IgG1 Variants with Improved Binding to the FcγR," The Journal of Biological Chemistry, vol. 276, issue 9 (Mar. 2001) pp. 6591-6604.

Sims, M. J. et al. "A Humanized CD18 Antibody Can Block Function Without Cell Destruction," The Journal of Immunology, vol. 151, issue 4 (Aug. 15, 1993) pp. 2296-2308.

Sprague, Judy et al. "Expression of a recombinant DNA gene coding for the vesicular stomatitis virus nucleocapsid protein," Journal of Virology, vol. 45, issue 2 (Feb. 1983) pp. 773-781.

Steenbakkers, Peter G. et al. "Efficient generation of monoclonal antibodies from preselected antigen specific B cells," Molecular Biology Reports, vol. 19 (1994) pp. 125-134.

Suresh, M.R. et al. "[17] Bispecific monoclonal antibodies from hybrid hybridomas," Methods in Enzymology, vol. 121 (1986) pp. 210-228.

Taylor, Lisa D. et al. "A transgenic mouse that expresses a diversity of human sequence heavy and light chain immunoglobulins," Nucleic Acids Research, vol. 20, No. 23 (1992) pp. 6287-6295.

Taylor, Lisa D. et al. "Human immunoglobulin transgenes undergo rearrangement, somatic mutation and class switching in mice that lack endogenous IgM," International Immunology, vol. 6, issue 4 (Apr. 1994) pp. 579-591.

Toussi, Atrin et al. "Updated therapies for the management of Psoriatic Arthritis," Clinical Immunology, vol. 220 (Nov. 2020). 10 pages.

Traunecker, Andre. "Bispecific single chain molecules (Janusins) target cytotoxic lymphocytes on HIV infected cells," et al., The EMBO Journal, vol. 10, No. 12 (1991) pp. 3655-3659.

Tuaillon, Nadine et al. "Human immunoglobulin heavy-chain minilocus recombination in transgenic mice: Gene-segment use in , u and y transcripts," Proceedings of the National Academy of Sciences of the United States of America, vol. 90 (Apr. 1993) pp. 3720-3724.

Umaña, Pablo et al. "Engineered glycoforms of an antineuroblastoma IgG1 with optimized antibody-dependent cellular cytotoxic activity," Nature Biotechnology, vol. 17 (1999) pp. 176-180.

Verhoeyen, Martine et al. "Reshaping Human Antibodies: Grafting an Antilysozyme Activity," Science, vol. 239, issue 4847 (Mar. 1998) pp. 1534-1536.

Wen, Li "Limiting dilution assay for human B cells based on their activation by mutant EL4 thymoma cells: total and anti-malaria responder B cell frequencies," European Journal of Immunology, vol. 17, issue 6 (1987) pp. 887-892.

Whitelam, Garry C. et al. "Antibody production in transgenic plants," Biochemical Society Transactions, vol. 22, issue 4 (1994) pp. 940-944.

Mantravadi et al., "Tumor necrosis factor inhibitors in psoriatic arthritis," Expert Rev. Clin. Pharmacol. 10(8):899-910 (2017).

Mease et al., "Guselkumab in biologic-naive patients with active psoriatic arthritis (Discover-2): a double-blind, randomised, placebo-controlled phase 3 trial," Lancet 395(10230):1126-1136 (2020).

Clinical Trial NCT03158285 "A Study Evaluating the Efficacy and Safety of Guselkumab Administered Subcutaneously in Participants With Active Psoriatic Arthritis", Version 38, Aug. 12, 2020.

Hu C., et al., "Improvement in Latent Variable Indirect Response Modeling of Multiple Categorical Clinical Endpoints: Application to Modeling of Guselkumab Treatment Effects in Psoriatic Patients," Journal of Pharmacokinetics and Pharmacodynamics, Jun. 20, 2017, vol. 44 (5), pp. 437-448.

Jesitus J., et al., "Guselkumab for Scalp, Hand and Foot Psoriasis: IL-23 Inhibitor Outduels Adalimumab," Dermatology Times, Aug. 2018, vol. 39 (9), pp. 49-51.

Johnsson H.J., et al., "Interleukin-12 and Interleukin-23 Inhibition in Psoriatic Arthritis," Clinical and Experimental Rheumatology, Sep. 1, 2015, vol. 33 (5), pp. S115-S118.

Kavanaugh A., et al., "Infliximab Maintains a High Degree of Clinical Response in Patients with Active Psoriatic Arthritis Through 1 Year of Treatment: Results from the IMPACT 2 Trial," Annals of the Rheumatic Diseases, Nov. 17, 2006, vol. 66 (4), pp. 498-505.

Krstic A., et al., "The Potential of Interleukin-17 to Mediate Hematopoietic Response," Immunology Research, Mar. 4, 2012, vol. 52, pp. 34-41.

Langley R.G., et al., "Secukinumab in Plaque Psoriasis - Results of Two Phase 3 Trials, " The New England Journal of Medicine, Jul. 24, 2014, vol. 371, No. 4, pp. 326-338.

Langley R.G., et al., "Efficacy and Safety of Guselkumab in Patients With Psoriasis Who Have an Inadequate Response to Ustekinumab: Results of the Randomized, Double-Blind, Phase 3 NAVIGATE Trial," British Journal of Dermatology, 2018, vol. 178, No. 1, pp. 114-123 (22 Pages).

Langrish C.L., et al., "IL-23 Drives a Pathogenic T Cell Population That Induces Autoimmune Inflammation," The Journal Of Experimental Medicine, Jan. 17, 2005, vol. 201 (2), pp. 233-240.

Lebwohl M., et al., "Phase 3 Studies Comparing Brodalumab with Ustekinumab in Psoriasis," The New England Journal of Medicine, Oct. 1, 2015, vol. 373, No. 14, pp. 1318-1328.

Leonard J.P., et al., "Prevention of Experimental Autoimmune Encephalomyelitis by Antibodies Against Interleukin 12," The Journal of Experimental Medicine, Jan. 1, 1995, vol. 181, pp. 381-386.

Leonardi C.L., et al., "Efficacy and Safety of Ustekinumab, a Human Interleukin-12/23 Monoclonal Antibody, in Patients With Psoriasis: 76-week Results From a Randomised, Double-blind, Placebo-controlled Trial (PHOENIX 1)," Lancet, May 17, 2008, vol. 371, pp. 1665-1674.

Liu Y., et al., "A Genome-Wide Association Study of Psoriasis and Psoriatic Arthritis Identifies New Disease Loci," Plos Genetics, Mar. 2008, vol. 4, No. 3 (e1000041), pp. 1-14.

Lloyd P., et al., "Psoriatic Arthritis: An Update," Arthritis, Oct. 17, 2012, vol. 2012, Article ID. 176298, pp. 1-6.

Ma Y-Q., et al., "Research Progress of Interleukin-23 Inhibitors in Treating Psoriasis," Chinese Journal of New Drugs, Apr. 2018, vol. 27, No. 8, Abstract Only, 1 page.

Machado A., et al., "Guselkumab for the Treatment of Psoriasis," BioDrugs, 2018, vol. 32, pp. 119-128.

Malfait A.M., et al., "Blockade of II-12 During the Induction of Collagen-Induced Arthritis (Cia) Markedly Attenuates the Severity of the Arthritis," Clinical & Experimental Immunology, 1998, vol. 111, pp. 377-383.

Markham A., "Guselkumab: First Global Approval," Drugs, 2017, vol. 77, pp. 1487-1492.

Mcinnes I.B., et al., "Secukinumab, a Human Anti-Interleukin-17A Monoclonal Antibody, in Patients with Psoriatic Arthritis (FUTURE 2): A Randomised, Double-Blind, Placebo-Controlled, Phase 3 Trial," The Lancet, Sep. 19, 2015, vol. 386 (9999), pp. 1137-1146.

Mcinnes I.B., et al., "Efficacy and Safety of Ustekinumab in Patients with Active Psoriatic Arthritis: 1 Year Results of the Phase 3, Multicentre, Double-Blind, Placebo-Controlled PSUMMIT 1 Trial," The Lancet, Jun. 13, 2013, vol. 382 (9894), pp. 780-789.

Mcinnes I.B., et al., "Swollen Joints are Associated with Ultrasound Power Doppler Synovitis, Whereas Tender Joints in the Absence of Swelling are Not: An Analysis of Agreement and Correlation in Very Early Dmard Naïve Psoriatic Arthritis," Annals of the Rheumatic Diseases, Jun. 6, 2020, vol. 79, p. 1152.

Mease P., "A Short History of Biological Therapy for Psoriatic Arthritis," Clinical and Experimental Rheumatology, Oct. 15, 2015, vol. 33, No. 5, Suppl. 93, pp. S104-S108, XP009520315.

Mease P. J., et al., "Brodalumab, an Anti-IL17RA Monoclonal Antibody, in Psoriatic Arthritis," The New England Journal of Medicine, Jun. 12, 2014, vol. 370 (24), pp. 2295-2306.

Mease P. J., et al., "Secukinumab Inhibition of Interleukin-17A in Patients with Psoriatic Arthritis," The New England Journal of Medicine, Oct. 1, 2015, vol. 373 (14), pp. 1329-1339.

Mease P.J., et al., "How Much Improvement in Functional Status is Considered Important by Patients with Active Psoriatic Arthritis: Applying the Outcome Measures in Rheumatoid Arthritis Clinical Trials (OMERACT) Group Guidelines," Annals of the Rheumatic Diseases, 2004, vol. 63 (Suppl 1), pp. SAT0015.

Mease P. J., et al., "Impact of Guselkumab, an Interleukin-23 p19 Subunit Inhibitor, on Enthesitis and Dactylitis in Patients with

(56) References Cited

OTHER PUBLICATIONS

Moderate to Severe Psoriatic Arthritis: Results from a Randomised, Placebo-Controlled, Phase II Study," RMD Open, Jul. 13, 2020, vol. 6 (2), pp. 1-10.

Mease P. J., et al., "Ixekizumab, an Interleukin-17A Specific Monoclonal Antibody, for the Treatment of Biologic-Naive Patients with Active Psoriatic Arthritis: Results from the 24-Week Randomised, Double-Blind, Placebo-Controlled and Active (Adalimumab)-Controlled Period of the Phase III Trial SPIRIT-P1," Annals of the Rheumatic Diseases, Aug. 23, 2016, vol. 76 (1), pp. 79-87.

Mease P. J., et al., "Minimally Important Difference of Health Assessment Questionnaire in Psoriatic Arthritis: Relating Thresholds of Improvement in Functional Ability to Patient-Rated Importance and Satisfaction," The Journal of Rheumatology, Nov. 2011, vol. 38 (11), pp. 2461-2465.

Megna M., et al., "Guselkumab for the Treatment of Psoriasis," Expert Opinion on Biological Therapy, 2018, vol. 18, No. 4, pp. 459-468 (11 Pages).

Mortezavi M., et al., "IL12/IL23 Inhibition in the Treatment of Psoriatic Arthritis," Current Treatment Options in Rheumatology, 2015, vol. 1, pp. 197-209.

Mumtaz A., et al., "Development of a Preliminary Composite Disease Activity Index in Psoriatic Arthritis," Annals of Rheumatological Disease, Apr. 1, 2011, vol. 70, No. 2, pp. 272-277 (8 Pages).

Murphy C.A., et al., "Divergent Pro- and Antiinflammatory Roles for IL-23 and IL-12 in Joint Autoimmune Inflammation," The Journal of Experimental Medicine, Dec. 15, 2003, vol. 198 (12), pp. 1951-1957.

Nair R.P., et al., "Genomewide Scan Reveals Association of Psoriasis with IL-23 and NF-KB Pathways," Nature Genetics, Feb. 2009, vol. 41 (2), pp. 199-204.

Nakamura M., et al., "Guselkumab for the Treatment of Psoriasis: A Review of Phase III Trials," Dermatology and Therapy, 2017, vol. 7, pp. 281-292.

NCT02203032, "A Study of Guselkumab In Participants With Moderate to Severe Plaque-Type Psoriasis and an Inadequate Response to US," Clinical Trials.gov [online], Jul. 12, 2016, 8 pages.

NCT02207231, "A Study of Guselkumab in the Treatment of Participants with Moderate to Severe Plaque-Type Psoriasis," Clinical Trials.gov [online], Jul. 4, 2016, 12 pages.

NCT02207244, "A Study of Guselkumb in the Treatement of Participants with Moderate to Severe Plaque-Type Psoriasis With Randomized Withdrawal," Clinical Trials.gov [online], Mar. 7, 2016, 12 pages.

NCT02905331, "Efficacy and Safety Study of Guselkumab in the Treatment of Participants with Moderate to Severe Plaque-Type Psoriasis," ClinicalTrials.gov, Sep. 6, 2018, 17 pages.

Ogdie A., et al., "The Changing Face of Clinical Trials in Psoriatic Arthritis," Curr. Rheumatol. Rep., Apr. 2017, vol. 19 (4), 18 pages.

Ohtsuki M., et al., "Guselkumab, an Anti-Interleukin-23 Monoclonal Antibody, for the Treatment of Moderate to Severe Plaque-Type Psoriasis in Japanese Patients: Efficacy and Safety Results From a Phase 3, Randomized, Double-Blind, Placebo-Controlled Study," The Journal of Dermatology, Japanese Dermatological Association, Tokyo, JP, May 7, 2018, vol. 45, No. 9, pp. 1053-1062, XP055766710.

Olivieri I., et al., "Advances in the Management of Psoriatic Arthritis," Nature Reviews Rheumatology, 2014, vol. 10, No. 9, pp. 531-542 (12 Pages), Published Online on Jul. 8, 2014.

Oppmann B., et al., "Novel p19 Protein Engages IL-12p40 to Form a Cytokine, IL-23, with Biological Activities Similar as Well as Distinct from IL-12," Immunity, Nov. 2000, vol. 13 (5), pp. 715-725.

Orchard T.R., et al., "Peripheral Arthropathies in Inflammatory Bowel Disease: Their Articular Distribution and Natural History," Gut, Mar. 1998, vol. 42, No. 3, pp. 387-391.

Ouyang W., et al., "The Biological Functions of T Helper 17 Cell Effector Cytokines in Inflammation," Immunity, Apr. 2008, vol. 28 (4), pp. 454-467.

Papp K.A., et al., "Efficacy and Safety of Ustekinumab, a Human Interleukin-12/23 Monoclonal Antibody, in Patients With Psoriasis: 52-week Results From a Randomised, Double-blind, Placebo-controlled Trial (PHOENIX 2)," Lancet, May 17, 2008, vol. 371, pp. 1675-1684.

Papp K.A., et al., "Risankizumab versus Ustekinumab for Moderate-to-Severe Plaque Psoriasis," The New England Journal of Medicine, Apr. 20, 2017, vol. 376 (16), pp. 1551-1560.

Parham C., et al., "A Receptor for the Heterodimeric Cytokine IL-23 is Composed of IL-12R{beta}1 and a Novel Cytokine Receptor Subunit, IL-23R," The Journal of Immunology, Dec. 25, 2002, vol. 168 (11), pp. 5699-5708.

Presky D.H., et al., "A Functional Interleukin 12 Receptor Complex Is Composed of Two Beta-Type Cytokine Receptor Subunits," Proceedings of the National Academy of Sciences, Nov. 1996, vol. 93, p. 14002-14007.

Rahman P., et al., "Association of Interleukin-23 Receptor Variants With Ankylosing Spondylitis," Arthritis & Rheumatism, Apr. 2008, vol. 58, No. 4, pp. 1020-1025.

Rahman P., et al., "Integrated Safety Results of Two Phase-3 Trials of Guselkumab in Patients With Psoriatic Arthritis Through the Placebo-Controlled Periods," Scientific Abstracts, Jun. 5, 2020, vol. 79, pp. 767-777.

Reich K., et al., "Efficacy and Safety of Guselkumab, an Anti-interleukin-23 Monoclonal Antibody, Compared With Adalimumab For the Treatment of Patients With Moderate to Severe Psoriasis With Randomized Withdrawal and Retreatment: Results From the Phase III, Double-blind, Placebo- and Active Comparator-controlled Voyage 2 Trial," , Journal of the American Academy of Dermatology, 2017, vol. 76, No. 3, pp. 418-431, Published Online on Jan. 2, 2017.

Ritchlin C.T., et al., "New Therapies for Psoriasis and Psoriatic Arthritis," Current Opinion Rheumatology, 2016, vol. 28 (3), pp. 204-210.

Sands B.E., et al., "Efficacy and Safety of MEDI2070, an Antibody Against Interleukin 23, in Patients With Moderate to Severe Crohn's Disease: A Phase 2a Study," Gastroenterology, Jul. 2017, vol. 153 (1), pp. 77-86.

Scher J.U., et al., "Decreased Bacterial Diversity Characterizes an Altered Gut Microbiota in Psoriatic Arthritis and Resembles Dysbiosis of Inflammatory Bowel Disease," Arthritis & Rheumatology, Jan. 2015, vol. 67, No. 1, pp. 128-139 (20 Pages).

Schoels M.M., et al., "Disease Activity in Psoriatic Arthritis (PsA): Defining Remission and Treatment Success using the DAPSA Score," Annals of Rheumatological Diseases, 2016, vol. 75, No. 5, pp. 811-818, Published Online on Aug. 12, 2015.

Sherlock J.P., et al., "IL-23 Induces Spondyloarthropathy by Acting on ROR-yt+ CD3+CD4-CD8- Entheseal Resident T Cells," Nature Medicine, Jul. 1, 2012, vol. 18 (7), pp. 1069-1076.

Siebert S., et al., "Guselkumab Induces Sustained Reduction in Acute Phase Proteins and Th17 Effector Cytokines in Active Psoriatic Arthritis in Two Phase-3 Clinical Trials (Discover-1 and Discover-2)," Scientific Abstracts, Jun. 1, 2020, vol. 79, pp. 144-145.

TALTZ (ixekizumab) Injection, for Subcutaneous Use, United States Prescribing Information, Eli Lilly and Company, Aug. 2024, 21 pages.

Targan S.R., et al., "A Randomized, Double-Blind, Placebo-Controlled Phase 2 Study of Brodalumab in Patients With Moderate-to-Severe Crohn's Disease," The American Journal of Gastroenterology, Nov. 2016, vol. 111, No. 11, pp. 1599-1607.

Tato C.M., et al., "Immunology: What Does It Mean to Be Just 17?," Nature, May 11, 2006, vol. 441 (7090), pp. 166-168.

Taylor W., et al., "Classification Criteria for Psoriatic Arthritis," Arthritis & Rheumatism, Aug. 2006, vol. 54, No. 8, pp. 2665-2673.

Teng M.W., et al., "IL-12 and IL-23 Cytokines: From Discovery to Targeted Therapies for Immune-Mediated Inflammatory Diseases," Nature Medicine, Jul. 2015, vol. 21 (7), pp. 719-729.

"TREMFYATM (guselkumab) injection for subcutaneous use" Jul. 2017, 97 pages.

Trinchieri G., "Interleukin-12 and the Regulation of Innate Resistance and Adaptive Immunity," Immunology, Feb. 2003, vol. 3, pp. 133-146.

(56) References Cited

OTHER PUBLICATIONS

Umaña et al., "Engineered Glycoforms of an Antineuroblastoma IgG1 with Optimized Antibody-dependent Cellular Cytotoxic Activity," Nature Biotechnology, vol. 17, No. 2, pp. 176-180, Feb. 1999.

Ungprasert P., et al., "Indirect Comparisons of the Efficacy of Biological Agents in Patients With Psoriatic Arthritis With an Inadequate Response to Traditional Disease-modifying Anti-rheumatic Drugs or to Non-steroidal Anti- inflammatory Drugs: A Meta-analysis," Seminars in Arthritis and Rheumatism, Feb. 2016, vol. 45, No. 4, pp. 428-438.

Valeri L., et al., "Mediation Analysis Allowing for Exposure-Mediator Interactions and Causal Interpretation: Theoretical Assumptions and Implementation With SAS and SPSS Macros," Psychological Methods, Jun. 2013, vol. 18 (2), pp. 137-150.

Ware J.E. Jr., et al., "The MOS 36-Item Short-Form Health Survey (SF-36). I. Conceptual Framework and Item Selection," Medical Care, Jun. 1992, vol. 30 (6), pp. 473-483.

Wechter T., et al., "Targeting p19 as a Treatment Option for Psoriasis: An Evidence-Based Review of Guselkumab," Therapeutics and Clinical Risk Management, 2018, vol. 14, pp. 1489-1497.

Wilson N.J., et al., "Development, Cytokine Profile and Function of Human Interleukin 17-Producing Helper T Cells," Nature Immunology, Sep. 2007, vol. 8 (9), pp. 950-957.

Yanqiao et al., "Research Progress of Interleukin-23 Inhibitors in Treating Psoriasis," Chinese Journal of New Drugs, vol. 27, No. 8, pp. 899-904, Dec. 31, 2018.

Aggarwal S., et al., "Interleukin-23 Promotes a Distinct CD4 T Cell Activation State Characterized by the Production of Interleukin-17," The Journal of Biological Chemistry, Jan. 17, 2003, vol. 278 (3), pp. 1910-1914.

Al-Salama Z.T., et al., "Guselkumab: A Review in Moderate to Severe Plaque Psoriasis," American Journal of Clinical Dermatology, 2018, vol. 19, pp. 907-918.

Anonymous: "Highlights of Prescribing Information," Annex A, Tremfya FDA label, TREMFYA (guselkumab) injection, for subcutaneous use Initial U.S. Approval: 2017, (Revised Jul. 2017), pp. 1-24.

Baeten D., et al., "Secukinumab, an Interleukin-17A Inhibitor, in Ankylosing Spondylitis," Th New Bngland Journal of Medicine, Dec. 24, 2015, vol. 373, No. 26, pp. 2534-2548.

Blauvelt A., et al., "Efficacy and Safety of Guselkumab, An Anti-interleukin-23 Monoclonal Antibody, Compared With Adalimumab For the Continuous Treatment of Patients With Moderate to Severe Psoriasis: Results From the Phase Iii, Double-blinded, Placebo- and Active Comparator-controlled Voyage 1 Trial," Journal of the American Academy of Dermatology, Mar. 31, 2017, vol. 76, No. 3, pp. 405-417, (Mar. 17, 2017).

Blauvelt A., et al., "Efficacy and Safety of Switching to Ixekizumab in Etanercept Non-Responders: A Subanalysis from Two Phase III Randomized Clinical Trials in Moderate-to-Severe Plaque Psoriasis (UNCOVER-2 and -3)," American Journal of Clinical Dermatology, Apr. 2017, vol. 18, pp. 273-280.

Bowes J., et al., "Confirmation of TNIP1 and IL23A as Susceptibility Loci for Psoriatic Arthritis," Annals of Rheumatological Diseases, 2011, vol. 70, pp. 1641-1644, (Accepted on Apr. 24, 2011).

Brown A.N., "Repository Corticotropin Injection in Patients With Refractory Psoriatic Arthritis: A Case Series," Open Access Rheumatology: Research and Reviews, Nov. 11, 2016, vol. 2016, No. 8, pp. 97-102.

Calabresi E., et al., "One Year in Review 2018: Psoriatic Arthritis," Clinical and Experimental Rheumatology, 2019, vol. 37, No. 2, pp. 167-178.

Cauli A., et al., "Patient Global Assessment in Psoriatic Arthritis: A Multicenter GRAPPA and OMERACT Study," The Journal of Rheumatology, May 2011, vol. 38 (5), pp. 898-903.

Cella D., et al., "Content Validity and Psychometric Evaluation of Functional Assessment of Chronic Illness Therapy- Fatigue in Patients with Psoriatic Arthritis," Journal of Patient-Reported Outcomes, May 20, 2019, vol. 3 (30), 12 pages.

Chen Z., et al., "Distinct Regulation of IL-17 in Human Helper T Lymphocytes," Arthritis & Rheumatism, Sep. 2007, vol. 56 (9), pp. 2936-2946.

CNTO1959PSA3001: Janssen Research & Development, Llc, "A Phase 3, Multicenter, Randomized, Double-blind, Placebo-controlled Study Evaluating the Efficacy and Safety of Guselkumab Administered Subcutaneously in Subjects with Active Psoriatic Arthritis Including Those Previously Treated with Biologic Anti-TNFa Agent(s)," Jan. 25, 2018, 127 pages.

CNTO1959PSA3002: Janssen Research & Development, Llc, "A Phase 3, Multicenter, Randomized, Double-blind, Placebo-controlled Study Evaluating the Efficacy and Safety of Guselkumab Administered Subcutaneously in Subjects with Active Psoriatic Arthritis," Jan. 23, 2018, 143 pages.

CNTO1959PSA3003: Janssen Research & Development, Llc, "A Study of Guselkumab in Participants With Active Psoriatic Arthritis and an Inadequate Response to Anti-Tumor Necrosis Factor Alpha (Anti-TNF Alpha) Therapy," Sep. 16, 2024, 11 pages.

Coates L.C., et al., "Defining Minimal Disease Activity in Psoriatic Arthritis: A Proposed Objective Target for Treatment," Annals of Rheumatological Diseases, 2010, vol. 69, pp. 48-53.

Coates L.C., et al., "Group for Research and Assessment of Psoriasis and Psoriatic Arthritis 2015 Treatment Recommendations for Psoriatic Arthritis," Arthritis & Rheumatology, May 2016, vol. 68, No. 5, pp. 1060-1071.

Coates L.C., et al., "Group for Research and Assessment of Psoriasis and Psoriatic Arthritis/Outcome Measures in Rheumatology Consensus-Based Recommendations and Research Agenda for Use of Composite Measures and Treatment Targets in Psoriatic Arthritis," Arthritis & Rheumatology, Mar. 3, 2018, vol. 70, No. 3, pp. 345-355.

Coates L.C., et al., "Validation of Minimal Disease Activity Criteria for Psoriatic Arthritis Using Interventional Trial Data," Arthritis Care & Research, Jul. 7, 2010, vol. 62, No. 7, pp. 965-969.

COSENTYX (secukinumab): Novartis Pharmaceuticals Corporation, "Cosentyx (Secukinumab) Injection, for Subcutaneous or Intravenous Use, United States Prescribing Information," Jan. 2015, Revised: Jul. 2023, 58 pages.

Cua J.P., et al., "Interleukin-23 Rather Than Interleukin-12 is the Critical Cytokine for Autoimmune Inflammation of the Brain," Letters to Nature, 2003, vol. 421, pp. 744-748.

Davidson N.J., et al., "IL-12, But Not IFN-y, Plays a Major Role in Sustaining the Chronic Phase of Colitis in IL-10- Deficient Mice," The Journal of Immunology, 1998, vol. 161 (6), pp. 3143-3149.

Deodhar A., et al., "Efficacy and Safety of Guselkumab in Patients With Active Psoriatic Arthritis: A Randomised, Double-Blind, Placebo-Controlled, Phase 2 Study," The Lancet, Jun. 2, 2018, vol. 391, pp. 2213-2224.

Deodhar A.A., et al., "Efficacy and Safety Results of Guselkumab, an Anti-IL23 Monoclonal Antibody, in Patients With Active Psoriatic Arthritis Over 24 Weeks: A Phase 2a, Randomized, Double-Blind, Placebo-Controlled Study," Arthritis & Rheumatology, Oct. 19, 2016, vol. 68 (Suppl 10), 3 pages.

Deodhar A.A., et al., "Efficacy and Safety Results of Guselkumab in Patients With Active Psoriatic Arthritis Over 56 Weeks From a Phase 2a, Randomized, Double-Blind, Placebo-Controlled Study," Arthritis & Rheumatology, Sep. 18, 2017, vol. 69 (Suppl 10), 4 pages.

Deodhar A.A., et al., "Efficiency and Safety Results of Guselkumab, an Anti-IL23 Monoclonal Antibody, in Patients With Active Psoriatic Arthritis Over 24 Weeks: A Phase 2A, Randomized, Double-Blind, Placebo-Controlled Study," Abstract No. 4L, Arthritis & Rheumatology, 2016, vol. 68, Suppl. 10, 4 Pages.

Dr. Huber W., et al., "Secukinumab, a Human Anti-il-17a Monoclonal Antibody, for Moderate to Severe Crohn's Disease: Unexpected Results of a Randomised, Double-blind Placebo-controlled Trial," Gut, Dec. 2012, vol. 61, No. 12, pp. 1693-1700 (18 Pages).

Duerr R.H., et al., "A Genome-Wide Association Study Identifies IL23R as an Inflammatory Bowel Disease Gene," Science, Dec. 1, 2006, vol. 314, No. 5804, pp. 1461-1463 (9 Pages).

Feagan B.G., et al., "Induction Therapy With the Selective Interleukin-23 Inhibitor Risankizumab in Patients With Moderate-to-severe

(56)                    References Cited

OTHER PUBLICATIONS

Crohn's Disease: A Randomised, Double-blind, Placebo-controlled Phase 2 Study," Lancet, Apr. 29, 2017, vol. 389, pp. 1699-1709.

Feagan B.G., et al., "Ustekinumab as Induction and Maintenance Therapy for Crohn's Disease," The New England Journal of Medicine, Nov. 17, 2016, vol. 375, No. 20, pp. 1946-1960.

Felson D.T., et al., "The American College of Rheumatology Preliminary Core Set of Disease Activity Measures for Rheumatoid Arthritis Clinical Trials," Arthritis & Rheumatism, Jun. 1993, vol. 36 (6), pp. 729-740.

Fredriksson T., et al., "Severe Psoriasis-Oral Therapy With a New Retinoid," Dermatologica, 1978, vol. 157 (4), pp. 238-244.

Fries J.F., et al., "Measurement of Patient Outcome in Arthritis," Arthritis & Rheumatism, Feb. 1980, vol. 23 (2), pp. 137-145.

Gaspari A.A., et al., "New and Emerging Biologic Therapies for Moderate-To-Severe Plaque Psoriasis: Mechanistic Rationales and Recent Clinical Data for IL-17 and IL-23 Inhibitors," Dermatologic Therapy, 2015, vol. 28, pp. 179-193.

Gladman D.D., et al., "SAT0322: The Effect of Guselkumab on Dactylitis: Results From a Phase 2 Study in Patients With Active Psoriatic Arthritis," Abstract No. 633, ACR Abstracts, 2018, 3 Pages.

Gomez-Reino J.J., et al., "Switching TNF Antagonists in Patients with Chronic Arthritis: An Observational Study of 488 Patients over a Four-year Period," Arthritis Research & Therapy, Jan. 6, 2006, vol. 08, Article No. R29, 7 pages.

Gordon K.B., et al., "A Phase 2 Trial of Guselkumab Versus Adalimumab for Plaque Psoriasis," The New England Journal of Medicine, Jul. 9, 2015, vol. 373, No. 2, pp. 136-144.

Gordon K.B., et al., "Phase 3 Trials of Ixekizumab in Moderate-to-Severe Plaque Psoriasis," The New England Journal of Medicine, Jul. 28, 2016, vol. 375, No. 4, pp. 345-356.

Gossec L., et al., "European League Against Rheumatism (Eular) Recommendations for the Management of Psoriatic Arthritis With Pharmacological Therapies: 2015 Update," Annals of Rheumatological Diseases, 2016, vol. 75, pp. 499-510.

Gottlieb A.B., et al., "Treatment Patterns, Unmet Need, and Impact of Psoriatic Arthritis on Patient-Reported Outcomes in the United States," Arthritis Rheumatol., 2016, vol. 68, 5 pages.

Healy P. J., et al., "Measuring Clinical Enthesitis in Psoriatic Arthritis: Assessment of Existing Measures and Development of an Instrument Specific to Psoriatic Arthritis," Arthritis & Rheumatism (Arthritis Care & Research), May 15, 2008, vol. 59 (5), pp. 686-691.

Helliwell P. S., et al., "Comparison of Composite Measures of Disease Activity in Psoriatic Arthritis Using Data From an Interventional Study With Golimumab," Arthritis Care & Research, May 2014, vol. 66, No. 5, pp. 749-756.

Helliwell P. S., et al., "Composite Disease Activity and Responder Indices for Psoriatic Arthritis: A Report from the GRAPPA 2013 Meeting on Development of Cutoffs for Both Disease Activity States and Response," The Journal of Rheumatology, 2014, vol. 41, No. 6, pp. 1212-1217.

Helliwell P. S., et al., "Efficacy of Guselkumab, a Monoclonal Antibody That Specifically Binds to the P19-Subunit of IL-23, on Endpoints Related to Axial Involvement in Patients With Active PSA," Annals of the Rheumatic Diseases, Jun. 1, 2020, vol. 79 (Suppl 1), pp. 36-37.

Helliwell P.S., et al., "Guselkumab Demonstrated an Independent Treatment Effect on Fatigue After Adjustment for Clinical Response (Acr20) in Patients With Psoriatic Arthritis: Results From Phase-3 Trials Discover 1 & 2," Annals of the Rheumatic Diseases, Jun. 1, 2020, vol. 79 (Suppl 1), 1 page.

Helliwell P. S., et al., "Radiographic Progression in Psoriatic Arthritis Achieving a Good Response to Treatment: Data Using Newer Composite Indices of Disease Activity," Arthritis Care & Research, May 2018, vol. 70, No. 5, pp. 797-800.

Her M., et al., "A Review of Disease Activity Measures for Psoriatic Arthritis: What is the Best Approach," Expert Review of Clinical Immunology, 2014, vol. 10, No. 9, pp. 1241-1254.

Hong K., et al., "IL-12, Independently of IFN-Gamma, Plays a Crucial Role in the Pathogenesis of a Murine Psoriasis- Like Skin Disorder," The Journal of Immunology, 1999, vol. 162 (12), pp. 7480-7491.

Howell S.T., et al., "Treating Moderate-to-Severe Psoriasis With Guselkumab: A Review of Phase II and Phase III Trials," Annals of Pharmacotherapy, 2018, vol. 52, No. 4, pp. 380-387.

Hu C., et al., "A Comprehensive Evaluation of Exposure-Response Relationships in Clinical Trials: Application to Support Guselkumab Dose Selection for Patients with Psoriasis," Journal of Pharmacokinetics and Pharmacodynamics, Mar. 16, 2018, vol. 45 (4), pp. 523-535.

* cited by examiner

Bolded p values are adjusted for multiplicity of testing; p values shown in parentheses are not adjusted for multiplicity of testing

SEQUENCE LISTING

<160> NUMBER OF SEQ ID NOS: 10

<210> SEQ ID NO 1
<211> LENGTH: 5
<212> TYPE: PRT
<213> ORGANISM: Homo sapiens

<400> SEQUENCE: 1

Asn Tyr Trp Ile Gly

```
1               5

<210> SEQ ID NO 2
<211> LENGTH: 17
<212> TYPE: PRT
<213> ORGANISM: Homo sapiens

<400> SEQUENCE: 2

Ile Ile Asp Pro Ser Asn Ser Tyr Thr Arg Tyr Ser Pro Ser Phe Gln
1               5                   10                  15

Gly

<210> SEQ ID NO 3
<211> LENGTH: 8
<212> TYPE: PRT
<213> ORGANISM: Homo sapiens

<400> SEQUENCE: 3

Trp Tyr Tyr Lys Pro Phe Asp Val
1               5

<210> SEQ ID NO 4
<211> LENGTH: 14
<212> TYPE: PRT
<213> ORGANISM: Homo sapiens

<400> SEQUENCE: 4

Thr Gly Ser Ser Ser Asn Ile Gly Ser Gly Tyr Asp Val His
1               5                   10

<210> SEQ ID NO 5
<211> LENGTH: 7
<212> TYPE: PRT
<213> ORGANISM: Homo sapiens

<400> SEQUENCE: 5

Gly Asn Ser Lys Arg Pro Ser
1               5

<210> SEQ ID NO 6
<211> LENGTH: 11
<212> TYPE: PRT
<213> ORGANISM: Homo sapiens

<400> SEQUENCE: 6

Ala Ser Trp Thr Asp Gly Leu Ser Leu Val Val
1               5                   10

<210> SEQ ID NO 7
<211> LENGTH: 117
<212> TYPE: PRT
<213> ORGANISM: Homo sapiens

<400> SEQUENCE: 7

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
            35                  40                  45

Gly Ile Ile Asp Pro Ser Asn Ser Tyr Thr Arg Tyr Ser Pro Ser Phe
            50                  55                  60
```

```
Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Tyr Tyr Lys Pro Phe Asp Val Trp Gly Gln Gly Thr Leu
                100                 105                 110

Val Thr Val Ser Ser
            115

<210> SEQ ID NO 8
<211> LENGTH: 111
<212> TYPE: PRT
<213> ORGANISM: Homo sapiens

<400> SEQUENCE: 8

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ser Gly
                20                  25                  30

Tyr Asp Val His Trp Tyr Gln Gln Leu Pro Gly Thr Ala Pro Lys Leu
                35                  40                  45

Leu Ile Tyr Gly Asn Ser Lys Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ser Glu Asp Glu Ala Asp Tyr Tyr Cys Ala Ser Trp Thr Asp Gly
                85                  90                  95

Leu Ser Leu Val Val Phe Gly Gly Gly Thr Lys Leu Thr Val Leu
                100                 105                 110

<210> SEQ ID NO 9
<211> LENGTH: 447
<212> TYPE: PRT
<213> ORGANISM: Homo sapiens

<400> SEQUENCE: 9

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
                20                  25                  30

Trp Ile Gly Trp Val Arg Gln Met Pro Gly Lys Gly Leu Glu Trp Met
        35                  40                  45

Gly Ile Ile Asp Pro Ser Asn Ser Tyr Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Tyr Tyr Lys Pro Phe Asp Val Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160
```

-continued

```
Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
        210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
                275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
                355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445

<210> SEQ ID NO 10
<211> LENGTH: 217
<212> TYPE: PRT
<213> ORGANISM: Homo sapiens

<400> SEQUENCE: 10

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ser Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Lys Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ser Glu Asp Glu Ala Asp Tyr Tyr Cys Ala Ser Trp Thr Asp Gly
                85                  90                  95
```

-continued

```
Leu Ser Leu Val Val Phe Gly Gly Gly Thr Lys Leu Thr Val Leu Gly
            100             105                 110

Gln Pro Lys Ala Ala Pro Ser Val Thr Leu Phe Pro Pro Ser Ser Glu
            115             120                 125

Glu Leu Gln Ala Asn Lys Ala Thr Leu Val Cys Leu Ile Ser Asp Phe
    130             135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
            195                 200                 205

Lys Thr Val Ala Pro Thr Glu Cys Ser
    210             215
```

METHOD OF TREATING PSORIATIC ARTHRITIS PATIENTS WITH INADEQUATE RESPONSE TO TNF THERAPY WITH ANTI-IL23 SPECIFIC ANTIBODY

CROSS-REFERENCE TO RELATED APPLICATIONS

This application claims the benefit of U.S. Provisional Application Ser. No. 63/160,078, filed 12 Mar. 2021 and 63/188,707, filed 14 May 2021. The entire contents of each of the aforementioned applications is incorporated herein by reference in their entireties.

REFERENCE TO SEQUENCE LISTING SUBMITTED ELECTRONICALLY

This application contains a sequence listing, which is submitted electronically via EFS-Web as an ASCII formatted sequence listing with a file name "JBI6473USNP1SEQLIST.txt" creation date of Mar. 4, 2022, and having a size of 9 KB. The sequence listing submitted via EFS-Web is part of the specification and is herein incorporated by reference in its entirety.

FIELD OF THE INVENTION

The present invention concerns methods for treating psoriatic arthritis with an antibody that binds the human IL-23 protein. In particular, it relates to a method of administering an anti-IL-23 specific antibody, e.g., guselkumab, which is safe and effective for patients suffering from psoriatic arthritis.

BACKGROUND OF THE INVENTION

Interleukin (IL)-12 is a secreted heterodimeric cytokine comprised of 2 disulfide-linked glycosylated protein subunits, designated p35 and p40 for their approximate molecular weights. IL-12 is produced primarily by antigen-presenting cells and drives cell-mediated immunity by binding to a two-chain receptor complex that is expressed on the surface of T cells or natural killer (NK) cells. The IL-12 receptor beta-1 (IL-12Rβ1) chain binds to the p40 subunit of IL-12, providing the primary interaction between IL-12 and its receptor. However, it is IL-12p35 ligation of the second receptor chain, IL-12Rβ2, that confers intracellular signaling (e.g. STAT4 phosphorylation) and activation of the receptor-bearing cell. IL-12 signaling concurrent with antigen presentation is thought to invoke T cell differentiation towards the T helper 1 (Th1) phenotype, characterized by interferon gamma (IFNγ) production. Th1 cells are believed to promote immunity to some intracellular pathogens, generate complement-fixing antibody isotypes, and contribute to tumor immunosurveillance. Thus, IL-12 is thought to be a significant component to host defense immune mechanisms.

It was discovered that the p40 protein subunit of IL-12 can also associate with a separate protein subunit, designated p19, to form a novel cytokine, IL-23. IL-23 also signals through a two-chain receptor complex. Since the p40 subunit is shared between IL-12 and IL-23, it follows that the IL-12Rβ1 chain is also shared between IL-12 and IL-23. However, it is the IL-23p19 ligation of the second component of the IL-23 receptor complex, IL-23R, that confers IL-23 specific intracellular signaling (e.g., STAT3 phosphorylation) and subsequent IL-17 production by T cells. Recent studies have demonstrated that the biological functions of IL-23 are distinct from those of IL-12, despite the structural similarity between the two cytokines.

Abnormal regulation of IL-12 and Th1 cell populations has been associated with many immune-mediated diseases since neutralization of IL-12 by antibodies is effective in treating animal models of psoriasis, multiple sclerosis (MS), rheumatoid arthritis, inflammatory bowel disease, insulin-dependent (type 1) diabetes mellitus, and uveitis. However, since these studies targeted the shared p40 subunit, both IL-12 and IL-23 were neutralized in vivo. Therefore, it was unclear whether IL-12 or IL-23 was mediating disease, or if both cytokines needed to be inhibited to achieve disease suppression. Studies have confirmed through IL-23p19 deficient mice or specific antibody neutralization of IL-23 that IL-23 inhibition can provide equivalent benefit as anti-IL-12p40 strategies. Therefore, there is increasing evidence for the specific role of IL-23 in immune-mediated disease. Neutralization of IL-23 without inhibition of IL-12 pathways could then provide effective therapy of immune-mediated disease with limited impact on important host defense immune mechanism. This would represent a significant improvement over current therapeutic options.

Psoriasis is a common, chronic immune-mediated skin disorder with significant co-morbidities, such as psoriatic arthritis (PsA), depression, cardiovascular disease, hypertension, obesity, diabetes, metabolic syndrome, and Crohn's disease. Plaque psoriasis is the most common form of the disease and manifests in well demarcated erythematous lesions topped with white silver scales. Plaques are pruritic, painful, often disfiguring and disabling, and a significant proportion of psoriatic patients have plaques on hands/nails face, feet and genitalia. As such, psoriasis negatively impacts health-related quality of life (HRQoL) to a significant extent, including imposing physical and psychosocial burdens that extend beyond the physical dermatological symptoms and interfere with everyday activities. For example, psoriasis negatively impacts familial, spousal, social, and work relationships, and is associated with a higher incidence of depression and increased suicidal tendencies.

Psoriatic arthritis (PsA) is a multi-system disease characterized by joint inflammation and psoriasis, with diverse clinical and radiographic manifestations including dactylitis, enthesitis, sacroiliitis, and/or joint deformity. Functional impairment, decreased quality of life, and increased healthcare resource utilization associated with poorly-controlled PsA present significant economic burden. Despite availability of biologics (e.g., tumor-necrosis-factor [TNF]α inhibitors, ustekinumab, secukinumab), and other agents (e.g., apremilast), significant unmet needs exist for new PsA therapies that can provide high levels of efficacy and safety in treating heterogeneous disease components Histologic characterization of psoriasis lesions reveals a thickened epidermis resulting from aberrant keratinocyte proliferation and differentiation as well as dermal infiltration and co-localization of CD3+T lymphocytes and dendritic cells. While the etiology of psoriasis is not well defined, gene and protein analysis have shown that IL-12, IL-23 and their downstream molecules are over-expressed in psoriatic lesions, and some may correlate with psoriasis disease severity. Some therapies used in the treatment of psoriasis modulate IL-12 and IL-23 levels, which is speculated to contribute to their efficacy. Th1 and Th17 cells can produce effector cytokines that induce the production of vasodilators, chemoattractants and expression of adhesion molecules on endothelial cells which in turn, promote monocyte and neutrophil recruitment, T cell infiltration, neovascularization and keratinocyte activation and hyperplasia. Activated keratinocytes can produce chemoattractant factors that promote neutrophil, monocyte, T cell, and dendritic cell trafficking, thus establishing a cycle of inflammation and keratinocyte hyperproliferation.

Elucidation of the pathogenesis of psoriasis has led to effective biologic treatments targeting tumor necrosis factor-alpha (TNF-α), both interleukin (IL)-12 and IL-23 and, most recently, IL-17 as well as IL-23 alone (including guselkumab). Guselkumab (also known as CNTO 1959, marketed as Tremfaya®) is a fully human IgG1 lambda monoclonal antibody that binds to the p19 subunit of IL-23 and inhibits the intracellular and downstream signaling of IL-23, required for terminal differentiation of T helper (Th)17 cells. Guselkumab is currently approved in the United States, European Union, and other countries worldwide for the treatment of moderate to severe plaque psoriasis and active psoriatic arthritis. In addition, guselkumab is being evaluated in several other immune-mediated disorders, including generalized pustular psoriasis, erythrodermic psoriasis, palmoplantar pustulosis, hidradenitis suppurativa, Crohn's disease and ulcerative colitis.

SUMMARY OF THE INVENTION

The invention relates to treatment of psoriastic arthritis (PsA). In particular, the invention relates to a clinically proven safe and effective method of treating PsA by administering an anti-IL-23 specific antibody to the subject.

In one general aspect, the invention relates to a method of treating psoriatic arthritis (PsA) in a subject in need thereof who is a non-responder to, has inadequate response (refractory) to and/or is intolerant of an anti-TNFα therapy, such as an anti-TNFα antibody, comprising subcutaneously administering an effective amount of an anti-IL-23 antibody (also referred to as IL-23p19 antibody), such as guselkumab, to the subject, wherein the anti-IL-23 antibody is administered once every 4 weeks (q4w). Preferably, the subject achieves at least a 20% improvement in the American College of Rheumatology core set disease index (ACR20) after the treatment, without having a clinically apparent adverse event.

In an embodiment, the anti-TNFα therapy is selected from the group consisting of etanercept, adalimumab, golimumab, or certolizumab pegol therapy, infliximab or biosimilars of those molecules.

In certain embodiments, the anti-IL-23 antibody comprises a heavy chain variable region and a light chain variable region, the heavy chain variable region comprising a complementarity determining region heavy chain 1 (CDRH1) amino acid sequence of SEQ ID NO: 1, a CDRH2 of SEQ ID NO: 2, and a CDRH3 of SEQ ID NO: 3; and the light chain variable region comprising a complementarity determining region light chain 1 (CDRL1) amino acid sequence of SEQ ID NO: 4, a CDRL2 of SEQ ID NO: 5, and a CDRL3 of SEQ ID NO: 6.

In certain embodiments, the anti-IL-23 antibody comprises the heavy chain variable region of the amino acid sequence of SEQ ID NO: 7, and the light chain variable region of the amino acid sequence of SEQ ID NO: 8.

In certain embodiments, the anti-IL-23 antibody comprises the heavy chain amino acid sequence of SEQ ID NO: 9, and the light chain amino acid sequence of SEQ ID NO: 10.

4

In certain embodiments, the anti-IL-23 antibody is administered at a total dosage of 25 mg to 200 mg, preferably about 50 mg to about 150 mg, more preferably about 100 mg, per administration.

In certain embodiments, the subject is a responder to the treatment with the anti-IL-23 antibody and is identified as having a statistically significant improvement in disease activity, wherein the disease activity is determined by one or more criteria selected from the group consisting of a 20% improvement in the American College of Rheumatology core set disease index (ACR20), a 50% improvement in the American College of Rheumatology core set disease index (ACR50), a 70% improvement in the American College of Rheumatology core set disease index (ACR70), Health Assessment Questionnaire Disability Index (HAQ-DI), Investigator's Global Assessment (IGA), Disease Activity Score 28 (DAS28) C-reactive protein (CRP), resolution of enthesitis, resolution of dactylitis, Leeds enthesitis index (LEI), dactylitis assessment score, Short Form Health survey (SF-36) in the mental and physical component summary (MCS and PCS), achievement of minimal disease activity (MDA), and achievement of very low disease activity (VLDA).

In another general aspect, the invention relates to a method of treating psoriastic arthritis in a subject in need thereof comprising subcutaneously administering an anti-IL-23 antibody to the subject, wherein the anti-IL-23 antibody is administered at an initial dose, a dose 4 weeks thereafter, and at a dosing interval of once every 8 weeks (q8w) thereafter, and wherein the subject has at least one psoriatic plaque of ≥2 cm diameter or nail changes consistent with psoriasis or documented history of plaque psoriasis. Preferably, the subject achieves at least a 20% improvement in the American College of Rheumatology core set disease index (ACR20) after the treatment, without having a clinically apparent adverse event.

In certain embodiments, the subject has had inadequate response to a standard therapy for the PsA. Optionally, the subject is also administered with the standard therapy during a treatment according to embodiments of the invention.

The details of one or more embodiments of the invention are set forth in the description below. Other features and advantages will be apparent from the following detailed description and the appended claims.

BRIEF DESCRIPTION OF THE DRAWINGS

The foregoing summary, as well as the following detailed description of the invention, will be better understood when read in conjunction with the appended drawings. It should be understood that the invention is not limited to the precise embodiments shown in the drawings.

DETAILED DESCRIPTION OF THE INVENTION

Figure 1A:
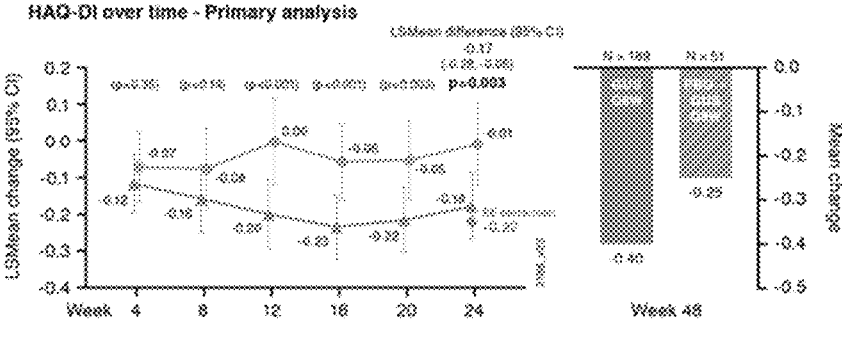
FIGS. 1A-1D show key secondary outcomes through week 48 of COSMOS. Primary analysis through week 24 and post-hoc NRI analysis at week 48 of LSmean change and mean change in HAQ-DI score (FIG. 1A), ACR50 response (FIG. 1B), LSmean change and mean change in SF-36 PCS score (FIG. 1C), and PASI100 response (FIG. 1D). After week 24, analyses were performed using NRI, including imputation of EE patients as nonresponders (see Patients and Methods). Results for the placebo→guselkumab group at week 48 are reported for patients who did not enter EE and crossed over to guselkumab at week 24. ACR50, improvement in American College of Rheumatology response criteria; CI, confidence interval; GUS, guselkumab; HAQ-DI, Health Assessment Questionnaire-Disability Index; LS, least squares; PASI100, 100% improvement in Psoriasis Area and Severity Index; PBO, placebo; Q8W every 8 weeks; SF-36 PCS, 36-item Short-Form Health Survey Physical Component Summary.
Figure 1B:
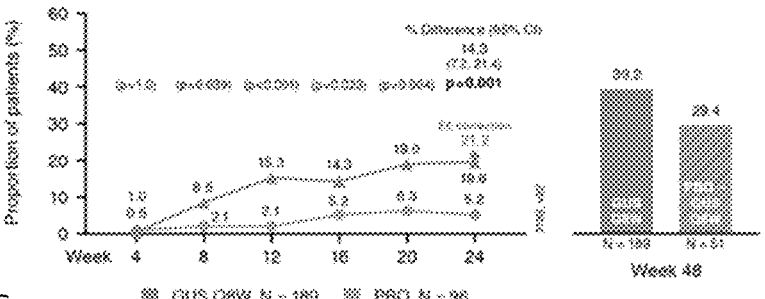
Figure 1C:
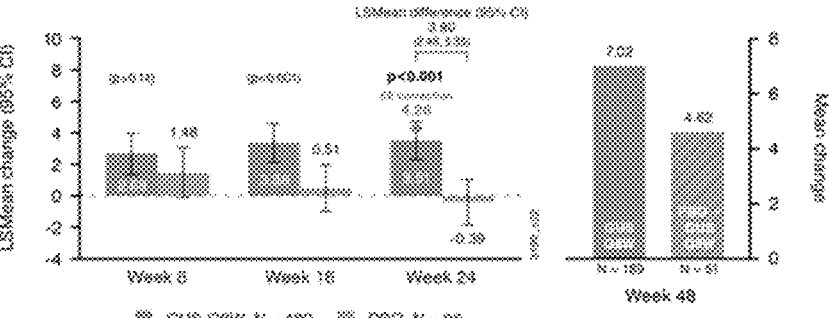
Figure 1D:
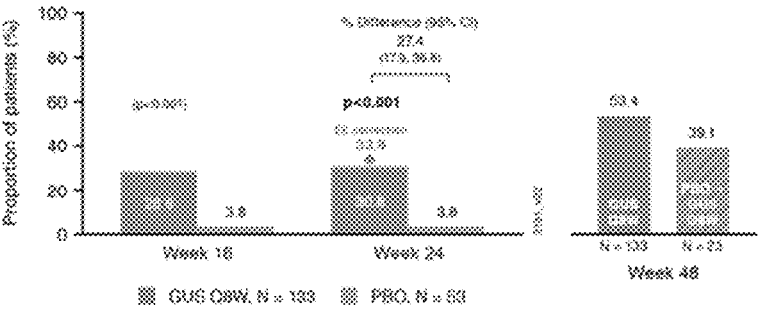

As used herein the method of treatment of psoriasis arthritis comprises administering isolated, recombinant and/or synthetic anti-IL-23 specific human antibodies and diagnostic and therapeutic compositions, methods and devices.

As used herein, an "anti-IL-23 specific antibody," "anti-IL-23 antibody," "antibody portion," or "antibody fragment" and/or "antibody variant" and the like include any protein or peptide containing molecule that comprises at least a portion of an immunoglobulin molecule, such as but not limited to, at least one complementarity determining region (CDR) of a heavy or light chain or a ligand binding portion thereof, a heavy chain or light chain variable region, a heavy chain or light chain constant region, a framework region, or any portion thereof, or at least one portion of an IL-23 receptor or binding protein, which can be incorporated into an antibody of the present invention. Such antibody optionally further affects a specific ligand, such as but not limited to, where such antibody modulates, decreases, increases, antagonizes, agonizes, mitigates, alleviates, blocks, inhibits, abrogates and/or interferes with at least one IL-23 activity or binding, or with IL-23 receptor activity or binding, in vitro, in situ and/or in vivo. As a non-limiting example, a suitable anti-IL-23 antibody, specified portion or variant of the present invention can bind at least one IL-23 molecule, or specified portions, variants or domains thereof. A suitable anti-IL-23 antibody, specified portion, or variant can also optionally affect at least one of IL-23 activity or function, such as but not limited to, RNA, DNA or protein synthesis, IL-23 release, IL-23 receptor signaling, membrane IL-23 cleavage, IL-23 activity, IL-23 production and/or synthesis.

The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof. Functional fragments include antigen-binding fragments that bind to a mammalian IL-23. For example, antibody fragments capable of binding to IL-23 or portions thereof, including, but not limited to, Fab (e.g., by papain digestion), Fab' (e.g., by pepsin digestion and partial reduction) and F(ab')2 (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the invention (see, e.g., Colligan, Immunology, supra).

Such fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a $F(ab')_2$ heavy chain portion can be designed to include DNA sequences encoding the $C_H1$ domain and/or hinge region of the heavy chain. The various portions of antibodies can be joined together chemically by conventional techniques or can be prepared as a contiguous protein using genetic engineering techniques.

As used herein, the term "human antibody" refers to an antibody in which substantially every part of the protein (e.g., CDR, framework, $C_L$, $C_H$ domains (e.g., $C_H1$, $C_H2$, $C_H3$), hinge, ($V_L$, $V_H$)) is substantially non-immunogenic in humans, with only minor sequence changes or variations. A "human antibody" may also be an antibody that is derived from or closely matches human germline immunoglobulin sequences. Human antibodies may include amino acid residues not encoded by germline immunoglobulin sequences (e.g., mutations introduced by random or site-specific mutagenesis in vitro or by somatic mutation in vivo). Often, this means that the human antibody is substantially non-immunogenic in humans. Human antibodies have been classified into groupings based on their amino acid sequence similarities. Accordingly, using a sequence similarity search, an antibody with a similar linear sequence can be chosen as a template to create a human antibody. Similarly, antibodies designated primate (monkey, baboon, chimpanzee, etc.), rodent (mouse, rat, rabbit, guinea pig, hamster, and the like) and other mammals designate such species, sub-genus, genus, sub-family, and family specific antibodies. Further, chimeric antibodies can include any combination of the above. Such changes or variations optionally and preferably retain or reduce the immunogenicity in humans or other species relative to non-modified antibodies. Thus, a human antibody is distinct from a chimeric or humanized antibody.

It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

Bispecific, heterospecific, heteroconjugate or similar antibodies can also be used that are monoclonal, preferably, human or humanized, antibodies that have binding specificities for at least two different antigens. In the present case, one of the binding specificities is for at least one IL-23 protein, the other one is for any other antigen. Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, Nature 305:537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed, e.g., in WO 93/08829, U.S. Pat. Nos. 6,210,668, 6,193,967, 6,132,992, 6,106,833, 6,060,285, 6,037,453, 6,010,902, 5,989,530, 5,959,084, 5,959,083, 5,932,448, 5,833,985, 5,821,333, 5,807,706, 5,643,759, 5,601,819, 5,582,996, 5,496,549, 4,676,980, WO 91/00360, WO 92/00373, EP 03089, Traunecker et al., EMBO J. 10:3655 (1991), Suresh et al., Methods in Enzymology 121:210 (1986), each entirely incorporated herein by reference.

Anti-IL-23 specific (also termed IL-23 specific antibodies) (or antibodies to IL-23) useful in the methods and compositions of the present invention can optionally be characterized by high affinity binding to IL-23 and, optionally and preferably, having low toxicity. In particular, an antibody, specified fragment or variant of the invention, where the individual components, such as the variable region, constant region and framework, individually and/or collectively, optionally and preferably possess low immunogenicity, is useful in the present invention. The antibodies that can be used in the invention are optionally characterized by their ability to treat patients for extended periods with measurable alleviation of symptoms and low and/or acceptable toxicity. Low or acceptable immunogenicity and/or high affinity, as well as other suitable properties, can contribute to the therapeutic results achieved. "Low immunogenicity" is defined herein as raising significant HAHA, HACA or HAMA responses in less than about 75%, or preferably less than about 50% of the patients treated and/or raising low titres in the patient treated (less than about 300, preferably less than about 100 measured with a double antigen enzyme immunoassay) (Elliott et al., *Lancet* 344: 1125-1127 (1994), entirely incorporated herein by reference). "Low immunogenicity" can also be defined as the incidence of titrable levels of antibodies to the anti-IL-23 antibody in patients treated with anti-IL-23 antibody as occurring in less than 25% of patients treated, preferably, in less than 10% of patients treated with the recommended dose for the recommended course of therapy during the treatment period.

The terms "clinically proven efficacy" and "clinically proven effective" as used herein in the context of a dose, dosage regimen, treatment or method refer to the clinically proven effectiveness of a particular dose, dosage or treatment regimen. Efficacy can be measured based on change in the course of the disease in response to an agent of the present invention based on the clinical trials conducted, e.g., Phase 3 clinical trials and earlier. For example, an anti-IL-23 antibody of the present invention (e.g., the anti-IL-23 antibody guselkumab) is administered to a patient in an amount and for a time sufficient to induce an improvement, preferably a sustained improvement, in at least one indicator that reflects the severity of the disorder that is being treated. Various indicators that reflect the extent of the subject's illness, disease or condition may be assessed for determining whether the amount and time of the treatment is sufficient. Such indicators include, for example, clinically recognized indicators of disease severity, symptoms, or manifestations of the disorder in question. The degree of improvement generally is determined by a physician, who may make this determination based on signs, symptoms, biopsies, or other test results, and who may also employ questionnaires that are administered to the subject, such as quality-of-life questionnaires developed for a given disease. For example, an anti-IL-23 antibody of the present invention can be administered to achieve an improvement in a patient's condition related to psoriatic arthritis. Improvement can be indicated by an improvement in an index of disease activity, by amelioration of clinical symptoms or by any other measure of disease activity.

In one embodiment, the efficacy of a treatment of psoriatic arthritis in a subject can be determined using the American College of Rheumatology (ACR) preliminary criteria for improvement in rheumatoid arthritis. ACR criteria measures improvement in tender or swollen joint counts and improvement in three of the following five parameters: acute phase reactant (such as sedimentation rate); patient assessment; physician assessment; pain scale; and disability/functional questionnaire. ACR criteria is indicated as ACR 20 (a 20 percent improvement in tender or swollen joint counts as well as 20 percent improvement in three of the other five criteria), ACR 50 (a 50 percent improvement in tender or swollen joint counts as well as 50 percent improvement in three of the other five criteria), and ACR 70 (a 70 percent improvement in tender or swollen joint counts as well as 70 percent improvement in three of the other five criteria) (see Felson D T, et al. Arthritis Rheum 1995; 38:727-35).

In another embodiment, the efficacy of a treatment of psoriatic arthritis in a subject is determined by the Psoriasis Area and Severity Index (PAST), which is an index of disease used to assess skin disease severity/extent, e.g., PASI75=75% improvement, PASI90=90% improvement and PASI100=substantially cleared of plaques. The measure of efficacy can also comprise one or more of the Health Assessment Questionnaire Disability Index (HAQ-DI), enthesitis/dactylitis improvements in patients with baseline enthesitis/dactylitis, changes in SF-36 mental and physical component summary (MCS and PCS) scores, and achievement of minimal disease activity (MDA) criteria score.

The term "clinically proven safe," as it relates to a dose, dosage regimen, treatment or method with an anti-IL-23 antibody of the present invention (e.g., the anti-IL-23 antibody guselkumab), refers to a relatively low or reduced frequency and/or low or reduced severity of treatment-emergent adverse events (referred to as AEs or TEAEs) from the clinical trials conducted, e.g., Phase 2 clinical trials and earlier, compared to the standard of care or to another comparator. An adverse event is an untoward medical occurrence in a patient administered a medicinal product. In particular, clinically proven safe as it relates to a dose, dosage regimen or treatment with an anti-IL-23 antibody of the present invention refers to a relatively low or reduced frequency and/or low or reduced severity of adverse events associated with administration of the antibody if attribution is considered to be possible, probable, or very likely due to the use of the anti-IL-23 antibody.

As used herein, unless otherwise noted, the term "clinically proven" (used independently or to modify the terms "safe" and/or "effective") shall mean that it has been proven by a clinical trial wherein the clinical trial has met the approval standards of U.S. Food and Drug Administration, EMEA or a corresponding national regulatory agency. For example, the clinical study may be an adequately sized, randomized, double-blinded study used to clinically prove the effects of the drug.

Utility

The isolated nucleic acids of the present invention can be used for production of at least one anti-IL-23 antibody or specified variant thereof, which can be used to measure or effect in a cell, tissue, organ or animal (including mammals and humans), to diagnose, monitor, modulate, treat, alleviate, help prevent the incidence of, or reduce the symptoms of psoriasis.

Such a method can comprise administering an effective amount of a composition or a pharmaceutical composition comprising at least one anti-IL-23 antibody to a cell, tissue, organ, animal or patient in need of such modulation, treatment, alleviation, prevention, or reduction in symptoms, effects or mechanisms. The effective amount can comprise an amount of about 0.001 to 500 mg/kg per single (e.g., bolus), multiple or continuous administration, or to achieve a serum concentration of 0.01-5000 μg/ml serum concentration per single, multiple, or continuous administration, or any effective range or value therein, as done and determined using known methods, as described herein or known in the relevant arts.

CITATIONS

All publications or patents cited herein, whether or not specifically designated, are entirely incorporated herein by reference as they show the state of the art at the time of the present invention and/or to provide description and enablement of the present invention. Publications refer to any scientific or patent publications, or any other information available in any media format, including all recorded, electronic or printed formats. The following references are entirely incorporated herein by reference: Ausubel, et al., ed., Current Protocols in Molecular Biology, John Wiley & Sons, Inc., NY, NY (1987-2001); Sambrook, et al., Molecular Cloning: A Laboratory Manual, $2^{nd}$ Edition, Cold Spring Harbor, N.Y. (1989); Harlow and Lane, antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, NY, (1997-2001).

Antibodies Useful for the Present Invention—Production and Generation

At least one anti-IL-23 antibody used in the method of the present invention can be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, NY (1987-2001); Sambrook, et al., Molecular Cloning: A Laboratory Manual, 2nd Edition, Cold Spring Harbor, N.Y. (1989); Harlow and Lane, antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, NY, (1997-2001), each entirely incorporated herein by reference.

Human antibodies that are specific for human IL-23 proteins or fragments thereof can be raised against an appropriate immunogenic antigen, such as an isolated IL-23 protein and/or a portion thereof (including synthetic molecules, such as synthetic peptides). Other specific or general mammalian antibodies can be similarly raised. Preparation of immunogenic antigens, and monoclonal antibody production can be performed using any suitable technique.

In one approach, a hybridoma is produced by fusing a suitable immortal cell line (e.g., a myeloma cell line, such as, but not limited to, Sp2/0, Sp2/0-AG14, NSO, NS1, NS2, AE-1, L.5, L243, P3X63Ag8.653, Sp2 SA3, Sp2 MAI, Sp2 SS1, Sp2 SA5, U937, MLA 144, ACT IV, MOLT4, DA-1, JURKAT, WEHI, K-562, COS, RAJI, NIH 3T3, HL-60, MLA 144, NAMALWA, NEURO 2A, or the like, or heteromylomas, fusion products thereof, or any cell or fusion cell derived therefrom, or any other suitable cell line as known in the art) (see, e.g., www.atcc.org, www.lifetech.com., and the like), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. See, e.g., Ausubel, supra, and Colligan, Immunology, supra, chapter 2, entirely incorporated herein by reference.

Antibody producing cells can also be obtained from the peripheral blood or, preferably, the spleen or lymph nodes, of humans or other suitable animals that have been immunized with the antigen of interest. Any other suitable host cell can also be used for expressing heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods. Cells which produce antibodies with the desired specificity can be selected by a suitable assay (e.g., ELISA).

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, or the like, display library; e.g., as available from Cambridge antibody Technologies, Cambridgeshire, UK; MorphoSys, Martinsreid/Planegg, DE; Biovation, Aberdeen, Scotland, UK; BioInvent, Lund, Sweden; Dyax Corp., Enzon, Affymax/Biosite; Xoma, Berkeley, Calif.; Ixsys. See, e.g., EP 368,684, PCT/GB91/01134; PCT/GB92/01755; PCT/GB92/002240; PCT/GB92/00883; PCT/GB93/00605; U.S. Ser. No. 08/350,260(May 12, 1994); PCT/GB94/01422; PCT/GB94/02662; PCT/GB97/01835; (CAT/MRC); WO90/14443; WO90/14424; WO90/14430; PCT/US94/1234; WO92/18619; WO96/07754; (Scripps); WO96/13583, WO97/08320 (MorphoSys); WO95/16027 (BioInvent); WO88/06630; WO90/3809 (Dyax); U.S. Pat. No. 4,704,692 (Enzon); PCT/US91/02989 (Affymax); WO89/06283; EP 371 998; EP 550 400; (Xoma); EP 229 046; PCT/US91/07149 (Ixsys); or stochastically generated peptides or proteins—U.S. Pat. Nos. 5,723,323, 5,763,192, 5,814,476, 5,817,483, 5,824,514, 5,976,862, WO 86/05803, EP 590 689 (Ixsys, predecessor of Applied Molecular Evolution (AME), each entirely incorporated herein by reference)) or that rely upon immunization of transgenic animals (e.g., SCID mice, Nguyen et al., Microbiol. Immunol. 41:901-907 (1997); Sandhu et al., Crit. Rev. Biotechnol. 16:95-118 (1996); Eren et al., Immunol. 93:154-161 (1998), each entirely incorporated by reference as well as related patents and applications) that are capable of producing a repertoire of human antibodies, as known in the art and/or as described herein. Such techniques, include, but are not limited to, ribosome display (Hanes et al., Proc. Natl. Acad. Sci. USA, 94:4937-4942 (May 1997); Hanes et al., Proc. Natl. Acad. Sci. USA, 95:14130-14135 (Nov. 1998)); single cell antibody producing technologies (e.g., selected lymphocyte antibody method ("SLAM") (U.S. Pat. No. 5,627,052, Wen et al., J. Immunol. 17:887-892 (1987); Babcook et al., Proc. Natl. Acad. Sci. USA 93:7843-7848 (1996)); gel microdroplet and flow cytometry (Powell et al., Biotechnol. 8:333-337 (1990); One Cell Systems, Cambridge, Mass.; Gray et al., J. Imm. Meth. 182:155-163 (1995); Kenny et al., Bio/Technol. 13:787-790 (1995)); B-cell selection (Steenbakkers et al., Molec. Biol. Reports 19:125-134 (1994); Jonak et al., Progress Biotech, Vol. 5, In Vitro Immunization in Hybridoma Technology, Borrebaeck, ed., Elsevier Science Publishers B.V., Amsterdam, Netherlands (1988)).

Methods for engineering or humanizing non-human or human antibodies can also be used and are well known in the art. Generally, a humanized or engineered antibody has one or more amino acid residues from a source that is non-human, e.g., but not limited to, mouse, rat, rabbit, non-human primate or other mammal. These non-human amino acid residues are replaced by residues often referred to as "import" residues, which are typically taken from an "import" variable, constant or other domain of a known human sequence.

Known human Ig sequences are disclosed, e.g., www.ncbi.nlm.nih.gov/entrez/query.fcgi; www.ncbi.nih.gov/igblast; www.atcc.org/phage/hdb.html; www.mrc-cpe.cam.ac.uk/ALIGNMENTS.php; www.kabatdatabase.com/top.html; ftp.ncbi.nih.gov/repository/kabat; www.sciquest.corn; www.abcam.com; www.antibodyresource.com/onlinecomp.html; www.public.iastate.edu/~pedro/research tools.html; www.whfreeman.com/immunology/CH05/kuby05.htm; www.hhmi.org/grants/lectures/1996/vlab; www.path.cam.ac.uk/~mrc7/mikeimages.html; mcb.harvard.edu/BioLinks/Immunology.html; www.immunologylink.corn; pathbox.wustl.edu/~hcenter/index.html; www.appliedbiosystems.corn; www.nal.usda.gov/awic/pubs/antibody; www.m.ehime-u.ac.jp/~yasuhito/Elisa.html; www.biodesign.corn; www.cancerresearchuk.org; www.biotech.ufl.edu; www.isac-net.org; baserv.uci.kun.nl/~jraats/linksl.html; www.recab.uni-hd.de/immuno.b-me.nwu.edu; www.mrc-cpe.cam.ac.uk; www.ibt.unam.mx/vir/V_mice.html; http://www.bioinforg.uk/abs; antibody.bath.ac.uk; www.unizh.ch; www.cryst.bbk.ac.uk/~ubcg07s; www.nimr.mrc.ac.uk/CC/ccaewg/ccaewg.html; www.path.cam.ac.uk/~mrc7/humanisation/TAHHP.html; www.ibt.unam.mx/vir/structure/stat_aim.html; www.biosci.missouri.edu/smithgp/index.html; www.jerini.de; Kabat et al., Sequences of Proteins of Immunological Interest, U.S. Dept. Health (1983), each entirely incorporated herein by reference.

Such imported sequences can be used to reduce immunogenicity or reduce, enhance or modify binding, affinity, on-rate, off-rate, avidity, specificity, half-life, or any other suitable characteristic, as known in the art. In general, the CDR residues are directly and most substantially involved in influencing antigen binding. Accordingly, part or all of the non-human or human CDR sequences are maintained while the non-human sequences of the variable and constant regions may be replaced with human or other amino acids.

Antibodies can also optionally be humanized or human antibodies engineered with retention of high affinity for the antigen and other favorable biological properties. To achieve this goal, humanized (or human) antibodies can be optionally prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, framework (FR) residues can be selected and combined from the consensus and import sequences so that the desired antibody characteristic, such as increased affinity for the target antigen(s), is achieved.

In addition, the human IL-23 specific antibody used in the method of the present invention may comprise a human germline light chain framework. In particular embodiments, the light chain germline sequence is selected from human VK sequences including, but not limited to, A1, A10, A11, A14, A17, A18, A19, A2, A20, A23, A26, A27, A3, A30, A5, A7, B2, B3, L1, L10, L11, L12, L14, L15, L16, L18, L19, L2, L20, L22, L23, L24, L25, L4/18a, L5, L6, L8, L9, O1, O11, O12, O14, O18, O2, O4, and O8. In certain embodiments, this light chain human germline framework is selected from V1-11, V1-13, V1-16, V1-17, V1-18, V1-19, V1-2, V1-20, V1-22, V1-3, V1-4, V1-5, V1-7, V1-9, V2-1, V2-11, V2-13, V2-14, V2-15, V2-17, V2-19, V2-6, V2-7, V2-8, V3-2, V3-3, V3-4, V4-1, V4-2, V4-3, V4-4, V4-6, V5-1, V5-2, V5-4, and V5-6.

In other embodiments, the human IL-23 specific antibody used in the method of the present invention may comprise a human germline heavy chain framework. In particular embodiments, this heavy chain human germline framework is selected from VH1-18, VH1-2, VH1-24, VH1-3, VH1-45, VH1-46, VH1-58, VH1-69, VH1-8, VH2-26, VH2-5, VH2-70, VH3-11, VH3-13, VH3-15, VH3-16, VH3-20, VH3-21, VH3-23, VH3-30, VH3-33, VH3-35, VH3-38, VH3-43, VH3-48, VH3-49, VH3-53, VH3-64, VH3-66, VH3-7, VH3-72, VH3-73, VH3-74, VH3-9, VH4-28, VH4-31, VH4-34, VH4-39, VH4-4, VH4-59, VH4-61, VH5-51, VH6-1, and VH7-81.

In particular embodiments, the light chain variable region and/or heavy chain variable region comprises a framework region or at least a portion of a framework region (e.g., containing 2 or 3 subregions, such as FR2 and FR3). In certain embodiments, at least FRL1, FRL2, FRL3, or FRL4 is fully human. In other embodiments, at least FRH1, FRH2, FRH3, or FRH4 is fully human. In some embodiments, at least FRL1, FRL2, FRL3, or FRL4 is a germline sequence (e.g., human germline) or comprises human consensus sequences for the particular framework (readily available at the sources of known human Ig sequences described above). In other embodiments, at least FRH1, FRH2, FRH3, or FRH4 is a germline sequence (e.g., human germline) or comprises human consensus sequences for the particular framework. In preferred embodiments, the framework region is a fully human framework region.

Humanization or engineering of antibodies of the present invention can be performed using any known method, such as but not limited to those described in, Winter (Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,723,323, 5,976,862, 5,824,514, 5,817,483, 5,814,476, 5,763,192, 5,723,323, 5,766886, 5714352, 6204023, 6180370, 5693762, 5530101, 5585089, 5225539; 4816567, PCT/: US98/16280, US96/18978, US91/09630, US91/05939, US94/01234, GB89/01334, GB91/01134, GB92/01755; WO90/14443, WO90/14424, WO90/14430, EP 229246, each entirely incorporated herein by reference, included references cited therein.

In certain embodiments, the antibody comprises an altered (e.g., mutated) Fc region. For example, in some embodiments, the Fc region has been altered to reduce or enhance the effector functions of the antibody. In some embodiments, the Fc region is an isotype selected from IgM, IgA, IgG, IgE, or other isotype. Alternatively, or additionally, it may be useful to combine amino acid modifications with one or more further amino acid modifications that alter C1q binding and/or the complement dependent cytotoxicity function of the Fc region of an IL-23 binding molecule. The starting polypeptide of particular interest may be one that binds to C1q and displays complement dependent cytotoxicity (CDC). Polypeptides with pre-existing C1q binding activity, optionally further having the ability to mediate CDC may be modified such that one or both of these activities are enhanced. Amino acid modifications that alter C1q and/or modify its complement dependent cytotoxicity function are described, for example, in WO0042072, which is hereby incorporated by reference.

As disclosed above, one can design an Fc region of the human IL-23 specific antibody of the present invention with altered effector function, e.g., by modifying C1q binding and/or FcγR binding and thereby changing complement dependent cytotoxicity (CDC) activity and/or antibody-dependent cell-mediated cytotoxicity (ADCC) activity. "Effector functions" are responsible for activating or diminishing a biological activity (e.g., in a subject). Examples of effector functions include, but are not limited to: C1q binding; CDC; Fc receptor binding; ADCC; phagocytosis; down regulation of cell surface receptors (e.g., B cell receptor; BCR), etc. Such effector functions may require the Fc region to be combined with a binding domain (e.g., an antibody variable domain) and can be assessed using various assays (e.g., Fc binding assays, ADCC assays, CDC assays, etc.).

For example, one can generate a variant Fc region of the human IL-23 (or anti-IL-23) antibody with improved C1q binding and improved FcγRIIIbinding (e.g., having both improved ADCC activity and improved CDC activity). Alternatively, if it is desired that effector function be reduced or ablated, a variant Fc region can be engineered with reduced CDC activity and/or reduced ADCC activity. In other embodiments, only one of these activities may be increased, and, optionally, also the other activity reduced (e.g., to generate an Fc region variant with improved ADCC activity, but reduced CDC activity and vice versa).

Fc mutations can also be introduced in engineer to alter their interaction with the neonatal Fc receptor (FcRn) and improve their pharmacokinetic properties. A collection of human Fc variants with improved binding to the FcRn have been described (Shields et al., (2001). High resolution mapping of the binding site on human IgG1 for FcγRI, FcγRII, FcγRIII, and FcRn and design of IgG1 variants with improved binding to the FcγR, J. Biol. Chem. 276:6591-6604).

Another type of amino acid substitution serves to alter the glycosylation pattern of the Fc region of the human IL-23 specific antibody. Glycosylation of an Fc region is typically either N-linked or O-linked. N-linked refers to the attachment of the carbohydrate moiety to the side chain of an asparagine residue. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. The recognition sequences for enzymatic attachment of the carbohydrate moiety to the asparagine side chain peptide sequences are asparagine-X-serine and asparagine-X-threonine, where X is any amino acid except proline. Thus, the presence of either of these peptide sequences in a polypeptide creates a potential glycosylation site.

The glycosylation pattern may be altered, for example, by deleting one or more glycosylation site(s) found in the polypeptide, and/or adding one or more glycosylation sites that are not present in the polypeptide. Addition of glycosylation sites to the Fc region of a human IL-23 specific antibody is conveniently accomplished by altering the amino acid sequence such that it contains one or more of the above-described tripeptide sequences (for N-linked glycosylation sites). An exemplary glycosylation variant has an amino acid substitution of residue Asn 297 of the heavy chain. The alteration may also be made by the addition of, or substitution by, one or more serine or threonine residues to the sequence of the original polypeptide (for O-linked glycosylation sites). Additionally, a change of Asn 297 to Ala can remove one of the glycosylation sites.

In certain embodiments, the human IL-23 specific antibody of the present invention is expressed in cells that express beta (1,4)-N-acetylglucosaminyltransferase III (GnT III), such that GnT III adds GlcNAc to the human IL-23 antibody. Methods for producing antibodies in such a fashion are provided in WO/9954342, WO/03011878, patent publication 20030003097A1, and Umana et al., Nature Biotechnology, 17:176-180, Feb. 1999; all of which are herein specifically incorporated by reference in their entireties.

The anti-IL-23 antibody can also be optionally generated by immunization of a transgenic animal (e.g., mouse, rat, hamster, non-human primate, and the like) capable of producing a repertoire of human antibodies, as described herein and/or as known in the art. Cells that produce a human anti-IL-23 antibody can be isolated from such animals and immortalized using suitable methods, such as the methods described herein.

Transgenic mice that can produce a repertoire of human antibodies that bind to human antigens can be produced by known methods (e.g., but not limited to, U.S. Pat. Nos. 5,770,428, 5,569,825, 5,545,806, 5,625,126, 5,625,825, 5,633,425, 5,661,016 and 5,789,650 issued to Lonberg et al.; Jakobovits et al. WO 98/50433, Jakobovits et al. WO 98/24893, Lonberg et al. WO 98/24884, Lonberg et al. WO 97/13852, Lonberg et al. WO 94/25585, Kucherlapate et al. WO 96/34096, Kucherlapate et al. EP 0463 151 B1, Kucherlapate et al. EP 0710 719 A1, Surani et al. U.S. Pat. No. 5,545,807, Bruggemann et al. WO 90/04036, Bruggemann et al. EP 0438 474 B1, Lonberg et al. EP 0814 259 A2, Lonberg et al. GB 2 272 440 A, Lonberg et al. Nature 368:856-859 (1994), Taylor et al., Int. Immunol. 6(4)579-591 (1994), Green et al, Nature Genetics 7:13-21 (1994), Mendez et al., Nature Genetics 15:146-156 (1997), Taylor et al., Nucleic Acids Research 20(23):6287-6295 (1992), Tuaillon et al., Proc Natl Acad Sci USA 90(8)3720-3724 (1993), Lonberg et al., Int Rev Immunol 13(1):65-93 (1995) and Fishwald et al., Nat Biotechnol 14(7):845-851 (1996), which are each entirely incorporated herein by reference). Generally, these mice comprise at least one transgene comprising DNA from at least one human immunoglobulin locus that is functionally rearranged, or which can undergo functional rearrangement. The endogenous immunoglobulin loci in such mice can be disrupted or deleted to eliminate the capacity of the animal to produce antibodies encoded by endogenous genes.

Screening antibodies for specific binding to similar proteins or fragments can be conveniently achieved using peptide display libraries. This method involves the screening of large collections of peptides for individual members having the desired function or structure. Antibody screening of peptide display libraries is well known in the art. The displayed peptide sequences can be from 3 to 5000 or more amino acids in length, frequently from 5-100 amino acids long, and often from about 8 to 25 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT Patent Publication Nos. 91/17271, 91/18980, 91/19818, and 93/08278.

Other systems for generating libraries of peptides have aspects of both in vitro chemical synthesis and recombinant methods. See, PCT Patent Publication Nos. 92/05258, 92/14843, and 96/19256. See also, U.S. Pat. Nos. 5,658,754; and 5,643,768. Peptide display libraries, vector, and screening kits are commercially available from such suppliers as Invitrogen (Carlsbad, Calif.), and Cambridge antibody Technologies (Cambridgeshire, UK). See, e.g., U.S. Pat. Nos. 4,704,692, 4,939,666, 4,946,778, 5,260,203, 5,455,030, 5,518,889, 5,534,621, 5,656,730, 5,763,733, 5,767,260, 5,856,456, assigned to Enzon; U.S. Pat. Nos. 5,223,409, 5,403,484, 5,571,698, 5,837,500, assigned to Dyax, 5427908, 5580717, assigned to Affymax; 5885793, assigned to Cambridge antibody Technologies; 5750373, assigned to Genentech, 5618920, 5595898, 5576195, 5698435, 5693493, 5698417, assigned to Xoma, Colligan, supra; Ausubel, supra; or Sambrook, supra, each of the above patents and publications entirely incorporated herein by reference.

Antibodies used in the method of the present invention can also be prepared using at least one anti-IL23 antibody encoding nucleic acid to provide transgenic animals or mammals, such as goats, cows, horses, sheep, rabbits, and the like, that produce such antibodies in their milk. Such animals can be provided using known methods. See, e.g., but not limited to, U.S. Pat. Nos. 5,827,690; 5,849,992; 4,873, 316; 5,849,992; 5,994,616; 5,565,362; 5,304,489, and the like, each of which is entirely incorporated herein by reference.

Antibodies used in the method of the present invention can additionally be prepared using at least one anti-IL23 antibody encoding nucleic acid to provide transgenic plants and cultured plant cells (e.g., but not limited to, tobacco and maize) that produce such antibodies, specified portions or variants in the plant parts or in cells cultured therefrom. As a non-limiting example, transgenic tobacco leaves expressing recombinant proteins have been successfully used to provide large amounts of recombinant proteins, e.g., using an inducible promoter. See, e.g., Cramer et al., Curr. Top. Microbol. Immunol. 240:95-118 (1999) and references cited therein. Also, transgenic maize has been used to express mammalian proteins at commercial production levels, with biological activities equivalent to those produced in other recombinant systems or purified from natural sources. See, e.g., Hood et al., Adv. Exp. Med. Biol. 464:127-147 (1999) and references cited therein. Antibodies have also been produced in large amounts from transgenic plant seeds including antibody fragments, such as single chain antibodies (scFv's), including tobacco seeds and potato tubers. See, e.g., Conrad et al., Plant Mol. Biol. 38:101-109 (1998) and references cited therein. Thus, antibodies of the present invention can also be produced using transgenic plants, according to known methods. See also, e.g., Fischer et al., Biotechnol. Appl. Biochem. 30:99-108 (Oct., 1999), Ma et al., Trends Biotechnol. 13:522-7 (1995); Ma et al., Plant Physiol. 109:341-6 (1995); Whitelam et al., Biochem. Soc. Trans. 22:940-944 (1994); and references cited therein. Each of the above references is entirely incorporated herein by reference.

The antibodies used in the method of the invention can bind human IL-23 with a wide range of affinities ($K_D$). In a preferred embodiment, a human mAb can optionally bind human IL-23 with high affinity. For example, a human mAb can bind human IL-23 with a $K_D$ equal to or less than about $10^{-7}$M, such as but not limited to, 0.1-9.9 (or any range or value therein)$\times 10^{-7}$, $10^{-8}$, $10^{-9}$, $10^{-10}$, $10^{-11}$, $10^{-12}$, $10^{-13}$ or any range or value therein.

The affinity or avidity of an antibody for an antigen can be determined experimentally using any suitable method. (See, for example, Berzofsky, et al., "Antibody-Antigen Interactions," In *Fundamental Immunology*, Paul, W. E., Ed., Raven Press: New York, N.Y. (1984); Kuby, Janis *Immunology*, W. H. Freeman and Company: New York, N.Y. (1992); and methods described herein). The measured affinity of a particular antibody-antigen interaction can vary if measured under different conditions (e.g., salt concentration, pH). Thus, measurements of affinity and other antigen-binding parameters (e.g., $K_D$, $K_a$, $K_d$) are preferably made with standardized solutions of antibody and antigen, and a standardized buffer, such as the buffer described herein.

Nucleic Acid Molecules

Using the information provided herein, for example, the nucleotide sequences encoding at least 70-100% of the contiguous amino acids of at least one of the light or heavy chain variable or CDR regions described herein, among other sequences disclosed herein, specified fragments, variants or consensus sequences thereof, or a deposited vector comprising at least one of these sequences, a nucleic acid molecule of the present invention encoding at least one anti-IL-23 antibody can be obtained using methods described herein or as known in the art.

Nucleic acid molecules of the present invention can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules used in the method of the present invention can include nucleic acid molecules comprising an open reading frame (ORF), optionally, with one or more introns, e.g., but not limited to, at least one specified portion of at least one CDR, such as CDR1, CDR2 and/or CDR3 of at least one heavy chain or light chain; nucleic acid molecules comprising the coding sequence for an anti-IL-23 antibody or variable region; and nucleic acid molecules which comprise a nucleotide sequence substantially different from those described above but which, due to the degeneracy of the genetic code, still encode at least one anti-IL-23 antibody as described herein and/or as known in the art. Of course, the genetic code is well known in the art. Thus, it would be routine for one skilled in the art to generate such degenerate nucleic acid variants that code for specific anti-IL-23 antibodies used in the method of the present invention. See, e.g., Ausubel, et al., supra, and such nucleic acid variants are included in the present invention. Non-limiting examples of isolated nucleic acid molecules include nucleic acids encoding HC CDR1, HC CDR2, HC CDR3, LC CDR1, LC CDR2, and LC CDR3, respectively.

As indicated herein, nucleic acid molecules which comprise a nucleic acid encoding an anti-IL-23 antibody can include, but are not limited to, those encoding the amino acid sequence of an antibody fragment, by itself; the coding sequence for the entire antibody or a portion thereof; the coding sequence for an antibody, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example, ribosome binding and stability of mRNA); an additional coding sequence that codes for additional amino acids, such as those that provide additional functionalities. Thus, the sequence encoding an antibody can be fused to a marker sequence, such as a sequence encoding a peptide that facilitates purification of the fused antibody comprising an antibody fragment or portion.

Polynucleotides Selectively Hybridizing to a Polynucleotide as Described Herein

The method of the present invention uses isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library.

Preferably, the cDNA library comprises at least 80% full-length sequences, preferably, at least 85% or 90% full-length sequences, and, more preferably, at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

Optionally, polynucleotides will encode at least a portion of an antibody. The polynucleotides embrace nucleic acid sequences that can be employed for selective hybridization to a polynucleotide encoding an antibody of the present invention. See, e.g., Ausubel, supra; Colligan, supra, each entirely incorporated herein by reference.

Construction of Nucleic Acids

The isolated nucleic acids can be made using (a) recombinant methods, (b) synthetic techniques, (c) purification techniques, and/or (d) combinations thereof, as well-known in the art.

The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention, excluding the coding sequence, is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers are well known in the art. (See, e.g., Ausubel, supra; or Sambrook, supra)

Recombinant Methods for Constructing Nucleic Acids

The isolated nucleic acid compositions, such as RNA, cDNA, genomic DNA, or any combination thereof, can be obtained from biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library. The isolation of RNA, and construction of cDNA and genomic libraries, are well known to those of ordinary skill in the art. (See, e.g., Ausubel, supra; or Sambrook, supra)

Nucleic Acid Screening and Isolation Methods

A cDNA or genomic library can be screened using a probe based upon the sequence of a polynucleotide used in the method of the present invention, such as those disclosed herein. Probes can be used to hybridize with genomic DNA or cDNA sequences to isolate homologous genes in the same or different organisms. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by one or more of temperature, ionic strength, pH and the presence of a partially denaturing solvent, such as formamide. For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%, or 70-100%, or any range or value therein. However, it should be understood that minor sequence variations in the probes and primers can be compensated for by reducing the stringency of the hybridization and/or wash medium.

Methods of amplification of RNA or DNA are well known in the art and can be used according to the present invention without undue experimentation, based on the teaching and guidance presented herein.

Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; 4,795,699 and 4,921,794 to Tabor, et al; U.S. Pat. No. 5,142,033 to Innis; U.S. Pat. No. 5,122,464 to Wilson, et al.; U.S. Pat. No. 5,091,310 to Innis; U.S. Pat. No. 5,066,584 to Gyllensten, et al; U.S. Pat. No. 4,889,818 to Gelfand, et al; U.S. Pat. No. 4,994,370 to Silver, et al; U.S. Pat. No. 4,766,067 to Biswas; U.S. Pat. No. 4,656,134 to Ringold) and RNA mediated amplification that uses anti-sense RNA to the target sequence as a template for double-stranded DNA synthesis (U.S. Pat. No. 5,130,238 to Malek, et al, with the tradename NASBA), the entire contents of which references are incorporated herein by reference. (See, e.g., Ausubel, supra; or Sambrook, supra.)

For instance, polymerase chain reaction (PCR) technology can be used to amplify the sequences of polynucleotides used in the method of the present invention and related genes directly from genomic DNA or cDNA libraries. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, supra, Sambrook, supra, and Ausubel, supra, as well as Mullis, et al., U.S. Pat. No. 4,683,202 (1987); and Innis, et al., PCR Protocols A Guide to Methods and Applications, Eds., Academic Press Inc., San Diego, Calif. (1990). Commercially available kits for genomic PCR amplification are known in the art. See, e.g., Advantage-GC Genomic PCR Kit (Clontech). Additionally, e.g., the T4 gene 32 protein (Boehringer Mannheim) can be used to improve yield of long PCR products.

Synthetic Methods for Constructing Nucleic Acids

The isolated nucleic acids used in the method of the present invention can also be prepared by direct chemical synthesis by known methods (see, e.g., Ausubel, et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences.

Recombinant Expression Cassettes

The present invention uses recombinant expression cassettes comprising a nucleic acid. A nucleic acid sequence, for example, a cDNA or a genomic sequence encoding an antibody used in the method of the present invention, can be used to construct a recombinant expression cassette that can be introduced into at least one desired host cell. A recombinant expression cassette will typically comprise a polynucleotide operably linked to transcriptional initiation regulatory sequences that will direct the transcription of the polynucleotide in the intended host cell. Both heterologous and non-heterologous (i.e., endogenous) promoters can be employed to direct expression of the nucleic acids.

In some embodiments, isolated nucleic acids that serve as promoter, enhancer, or other elements can be introduced in the appropriate position (upstream, downstream or in the intron) of a non-heterologous form of a polynucleotide of the present invention so as to up or down regulate expression of a polynucleotide. For example, endogenous promoters can be altered in vivo or in vitro by mutation, deletion and/or substitution.

Vectors and Host Cells

The present invention also relates to vectors that include isolated nucleic acid molecules, host cells that are genetically engineered with the recombinant vectors, and the production of at least one anti-IL-23 antibody by recombinant techniques, as is well known in the art. See, e.g., Sambrook, et al., supra; Ausubel, et al., supra, each entirely incorporated herein by reference.

The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but are not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), mycophenolic acid, or glutamine synthetase (GS, U.S. Pat. Nos. 5,122,464; 5,770,359; 5,827, 739) resistance for eukaryotic cell culture, and tetracycline or ampicillin resistance genes for culturing in E. coli and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. Such methods are described in the art, such as Sambrook, supra, Chapters 1~4 and 16-18; Ausubel, supra, Chapters 1, 9, 13, 15, 16.

At least one antibody used in the method of the present invention can be expressed in a modified form, such as a fusion protein, and can include not only secretion signals, but also additional heterologous functional regions. For instance, a region of additional amino acids, particularly charged amino acids, can be added to the N-terminus of an antibody to improve stability and persistence in the host cell, during purification, or during subsequent handling and storage. Also, peptide moieties can be added to an antibody of the present invention to facilitate purification. Such regions can be removed prior to final preparation of an antibody or at least one fragment thereof. Such methods are described in many standard laboratory manuals, such as Sambrook, supra, Chapters 17.29-17.42 and 18.1-18.74; Ausubel, supra, Chapters 16, 17 and 18.

Those of ordinary skill in the art are knowledgeable in the numerous expression systems available for expression of a nucleic acid encoding a protein used in the method of the present invention. Alternatively, nucleic acids can be expressed in a host cell by turning on (by manipulation) in a host cell that contains endogenous DNA encoding an antibody. Such methods are well known in the art, e.g., as described in U.S. Pat. Nos. 5,580,734, 5,641,670, 5,733,746, and 5,733,761, entirely incorporated herein by reference.

Illustrative of cell cultures useful for the production of the antibodies, specified portions or variants thereof, are mammalian cells. Mammalian cell systems often will be in the form of monolayers of cells although mammalian cell suspensions or bioreactors can also be used. A number of suitable host cell lines capable of expressing intact glycosylated proteins have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, Cos-7 cells, CHO cells, hep G2 cells, P3X63Ag8.653, SP2/0-Ag14, 293 cells, HeLa cells and the like, which are readily available from, for example, American Type Culture Collection, Manassas, Va. (www.atcc.org). Preferred host cells include cells of lymphoid origin, such as myeloma and lymphoma cells. Particularly preferred host cells are P3X63Ag8.653 cells (ATCC Accession Number CRL-1580) and SP2/0-Ag14 cells (ATCC Accession Number CRL-1851). In a particularly preferred embodiment, the recombinant cell is a P3X63Ab8.653 or a SP2/0-Ag14 cell.

Expression vectors for these cells can include one or more of the following expression control sequences, such as, but not limited to, an origin of replication; a promoter (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human immunoglobulin promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra. Other cells useful for production of nucleic acids or proteins of the present invention are known and/or available, for instance, from the American Type Culture Collection Catalogue of Cell Lines and Hybridomas (www.atcc.org) or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., J. Virol. 45:773-781 (1983)). Additionally, gene sequences to control replication in the host cell can be incorporated into the vector, as known in the art.

Purification of an Antibody

An anti-IL-23 antibody can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, NY, (1997-2001), e.g., Chapters 1, 4, 6, 8, 9, 10, each entirely incorporated herein by reference.

Antibodies used in the method of the present invention include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody can be glycosylated or can be non-glycosylated, with glycosylated preferred. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14, all entirely incorporated herein by reference.

Anti-IL-23 Antibodies.

An anti-IL-23 antibody, also referred to herein as "anti-IL-23 specific antibody," useful for a method according to embodiments of the present invention includes any protein or peptide containing molecule that comprises at least a portion of an immunoglobulin molecule, such as but not limited to, at least one ligand binding portion (LBP), such as but not limited to, a complementarity determining region (CDR) of a heavy or light chain or a ligand binding portion thereof, a heavy chain or light chain variable region, a framework region (e.g., FR1, FR2, FR3, FR4 or fragment thereof, further optionally comprising at least one substitution, insertion or deletion), a heavy chain or light chain constant region, (e.g., comprising at least one $C_H1$, hinge1, hinge2, hinge3, hinge4, $C_H2$, or $C_H3$ or fragment thereof, further optionally comprising at least one substitution, insertion or deletion), or any portion thereof, that can be incorporated into an antibody. An antibody can include or be derived from any mammal, such as but not limited to, a human, a mouse, a rabbit, a rat, a rodent, a primate, or any combination thereof, and the like.

The isolated antibodies used in a method of the present invention comprise the antibody amino acid sequences disclosed herein encoded by any suitable polynucleotide, or any isolated or prepared antibody. Preferably, the human antibody or antigen-binding fragment binds human IL-23 and, thereby, partially or substantially neutralizes at least one biological activity of the protein. An antibody, or specified portion or variant thereof, that partially or preferably substantially neutralizes at least one biological activity of at least one IL-23 protein or fragment can bind the protein or fragment and thereby inhibit activities mediated through the binding of IL-23 to the IL-23 receptor or through other IL-23-dependent or mediated mechanisms. As used herein, the term "neutralizing antibody" refers to an antibody that can inhibit an IL-23-dependent activity by about 20-120%, preferably by at least about 10, 20, 30, 40, 50, 55, 60, 65, 70, 75, 80, 85, 90, 91, 92, 93, 94, 95, 96, 97, 98, 99, 100% or more depending on the assay. The capacity of an anti-IL-23 antibody to inhibit an IL-23-dependent activity is preferably assessed by at least one suitable IL-23 protein or receptor assay, as described herein and/or as known in the art. A human antibody can be of any class (IgG, IgA, IgM, IgE, IgD, etc.) or isotype and can comprise a kappa or lambda light chain. In one embodiment, the human antibody comprises an IgG heavy chain or defined fragment, for example, at least one of isotypes, IgG1, IgG2, IgG3 or IgG4 (e.g., γ1, γ2, γ3, γ4). Antibodies of this type can be prepared by employing a transgenic mouse or other trangenic non-human mammal comprising at least one human light chain (e.g., IgG, IgA, and IgM) transgenes as described herein and/or as known in the art. In another embodiment, the anti-IL-23 human antibody comprises an IgG1 heavy chain and an IgG1 light chain.

An antibody binds at least one specified epitope specific to at least one IL-23 protein, subunit, fragment, portion or any combination thereof. The at least one epitope can comprise at least one antibody binding region that comprises at least one portion of the protein, which epitope is preferably comprised of at least one extracellular, soluble, hydrophillic, external or cytoplasmic portion of the protein.

Generally, the human antibody or antigen-binding fragment will comprise an antigen-binding region that comprises at least one human complementarity determining region (CDR1, CDR2 and CDR3) or variant of at least one heavy chain variable region and at least one human complementarity determining region (CDR1, CDR2 and CDR3) or variant of at least one light chain variable region. The CDR sequences may be derived from human germline sequences or closely match the germline sequences. For example, the CDRs from a synthetic library derived from the original non-human CDRs can be used. These CDRs may be formed by incorporation of conservative substitutions from the original non-human sequence. In another particular embodiment, the antibody or antigen-binding portion or variant can have an antigen-binding region that comprises at least a portion of at least one light chain CDR (i.e., CDR1, CDR2 and/or CDR3) having the amino acid sequence of the corresponding CDRs 1, 2 and/or 3.

Such antibodies can be prepared by chemically joining together the various portions (e.g., CDRs, framework) of the antibody using conventional techniques, by preparing and expressing a (i.e., one or more) nucleic acid molecule that encodes the antibody using conventional techniques of recombinant DNA technology or by using any other suitable method.

In one embodiment, an anti-IL-23 antibody useful for the present invention comprises a heavy chain variable region and a light chain variable region, the heavy chain variable region comprising a complementarity determining region heavy chain 1 (CDRH1) amino acid sequence of SEQ ID NO: 1, a CDRH2 of SEQ ID NO: 2, and a CDRH3 of SEQ ID NO: 3; and the light chain variable region comprising a complementarity determining region light chain 1 (CDRL1) amino acid sequence of SEQ ID NO: 4, a CDRL2 of SEQ ID NO: 5, and a CDRL3 of SEQ ID NO: 6.

A preferred anti-IL-23 antibody useful for the present invention comprises a heavy chain variable region having the amino acid sequence of SEQ ID NO: 7 and a light chain variable region having the amino acid sequence of SEQ ID NO: 8.

A more preferred anti-IL-23 antibody useful for the present invention is guselkumab (also referred to as CNTO1959, marketed as Tremfaya®).

Other anti-IL-23 antibodies useful for the present invention include, but are not limited to, those having sequences described in U.S. Pat. No. 7,935,344, the entire contents of which are incorporated herein by reference).

Antibody Compositions Comprising Further Therapeutically Active Ingredients

The antibody compositions used in the method of the invention can optionally further comprise an effective amount of at least one compound or protein selected from at least one of an anti-infective drug, a cardiovascular (CV) system drug, a central nervous system (CNS) drug, an autonomic nervous system (ANS) drug, a respiratory tract drug, a gastrointestinal (GI) tract drug, a hormonal drug, a drug for fluid or electrolyte balance, a hematologic drug, an antineoplastic, an immunomodulation drug, an ophthalmic, otic or nasal drug, a topical drug, a nutritional drug or the like. Such drugs are well known in the art, including formulations, indications, dosing and administration for each presented herein (see, e.g., Nursing 2001 Handbook of Drugs, 21$^{st}$ edition, Springhouse Corp., Springhouse, P A, 2001; Health Professional's Drug Guide 2001, ed., Shannon, Wilson, Stang, Prentice-Hall, Inc, Upper Saddle River, NJ; Pharmcotherapy Handbook, Wells et al., ed., Appleton & Lange, Stamford, Conn., each entirely incorporated herein by reference).

By way of example of the drugs that can be combined with the antibodies for the method of the present invention, the anti-infective drug can be at least one selected from amebicides or at least one antiprotozoals, anthelmintics, antifungals, antimalarials, antituberculotics or at least one antileprotics, aminoglycosides, penicillins, cephalosporins, tetracyclines, sulfonamides, fluoroquinolones, antivirals, macrolide anti-infectives, and miscellaneous anti-infectives. The hormonal drug can be at least one selected from corticosteroids, androgens or at least one anabolic steroid, estrogen or at least one progestin, gonadotropin, antidiabetic drug or at least one glucagon, thyroid hormone, thyroid hormone antagonist, pituitary hormone, and parathyroid-like drug. The at least one cephalosporin can be at least one selected from cefaclor, cefadroxil, cefazolin sodium, cefdinir, cefepime hydrochloride, cefixime, cefmetazole sodium, cefonicid sodium, cefoperazone sodium, cefotaxime sodium, cefotetan disodium, cefoxitin sodium, cefpodoxime proxetil, cefprozil, ceftazidime, ceftibuten, ceftizoxime sodium, ceftriaxone sodium, cefuroxime axetil, cefuroxime sodium, cephalexin hydrochloride, cephalexin monohydrate, cephradine, and loracarbef.

The at least one coricosteroid can be at least one selected from betamethasone, betamethasone acetate or betamethasone sodium phosphate, betamethasone sodium phosphate, cortisone acetate, dexamethasone, dexamethasone acetate, dexamethasone sodium phosphate, fludrocortisone acetate, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, prednisolone, prednisolone acetate, prednisolone sodium phosphate, prednisolone tebutate, prednisone, triamcinolone, triamcinolone acetonide, and triamcinolone diacetate. The at least one androgen or anabolic steroid can be at least one selected from danazol, fluoxymesterone, methyltestosterone, nandrolone decanoate, nandrolone phenpropionate, testosterone, testosterone cypionate, testosterone enanthate, testosterone propionate, and testosterone transdermal system.

The at least one immunosuppressant can be at least one selected from azathioprine, basiliximab, cyclosporine, daclizumab, lymphocyte immune globulin, muromonab-CD3, mycophenolate mofetil, mycophenolate mofetil hydrochloride, sirolimus, and tacrolimus.

The at least one local anti-infective can be at least one selected from acyclovir, amphotericin B, azelaic acid cream, bacitracin, butoconazole nitrate, clindamycin phosphate, clotrimazole, econazole nitrate, erythromycin, gentamicin sulfate, ketoconazole, mafenide acetate, metronidazole (topical), miconazole nitrate, mupirocin, naftifine hydrochloride, neomycin sulfate, nitrofurazone, nystatin, silver sulfadiazine, terbinafine hydrochloride, terconazole, tetracycline hydrochloride, tioconazole, and tolnaftate. The at least one scabicide or pediculicide can be at least one selected from crotamiton, lindane, permethrin, and pyrethrins. The at least one topical corticosteroid can be at least one selected from betamethasone dipropionate, betamethasone valerate, clobetasol propionate, desonide, desoximetasone, dexamethasone, dexamethasone sodium phosphate, diflorasone diacetate, fluocinolone acetonide, fluocinonide, flurandrenolide, fluticasone propionate, halcionide, hydrocortisone, hydrocortisone acetate, hydrocortisone butyrate, hydrocorisone valerate, mometasone furoate, and triamcinolone acetonide. (See, e.g., pp. 1098-1136 of Nursing 2001 Drug Handbook.) Anti-IL-23 antibody compositions can further comprise at least one of any suitable and effective amount of a composition or pharmaceutical composition comprising at least one anti-IL-23 antibody contacted or administered to a cell, tissue, organ, animal or patient in need of such modulation, treatment or therapy, optionally further comprising at least one selected from at least one TNF antagonist (e.g., but not limited to a TNF chemical or protein antagonist, TNF monoclonal or polyclonal antibody or fragment, a soluble TNF receptor (e.g., p55, p70 or p85) or fragment, fusion polypeptides thereof, or a small molecule TNF antagonist, e.g., TNF binding protein I or II (TBP-1 or TBP-II), nerelimonmab, infliximab, eternacept, CDP-571, CDP-870, afelimomab, lenercept, and the like), an antirheumatic (e.g., methotrexate, auranofin, aurothioglucose, azathioprine, etanercept, gold sodium thiomalate, hydroxychloroquine sulfate, leflunomide, sulfasalzine), an immunization, an immunoglobulin, an immunosuppressive (e.g., basiliximab, cyclosporine, daclizumab), a cytokine or a cytokine antagonist. Non-limiting examples of such cytokines include, but are not limited to, any of IL-1 to IL-23 et al. (e.g., IL-1, IL-2, etc.). Suitable dosages are well known in the art. See, e.g., Wells et al., eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

Anti-IL-23 antibody compounds, compositions or combinations used in the method of the present invention can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., *Remington's Pharmaceutical Sciences, $18^{th}$* Edition, Mack Publishing Co. (Easton, Pa.) 1990. Pharmaceutically acceptable carriers can be routinely selected that are suitable for the mode of administration, solubility and/or stability of the anti-IL-23 antibody, fragment or variant composition as well known in the art or as described herein.

Pharmaceutical excipients and additives useful in the present composition include, but are not limited to, proteins, peptides, amino acids, lipids, and carbohydrates (e.g., sugars, including monosaccharides, di-, tri-, tetra-, and oligo-saccharides; derivatized sugars, such as alditols, aldonic acids, esterified sugars and the like; and polysaccharides or sugar polymers), which can be present singly or in combination, comprising alone or in combination 1-99.99% by weight or volume. Exemplary protein excipients include serum albumin, such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Carbohydrate excipients suitable for use in the invention include, for example, monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

Anti-IL-23 antibody compositions can also include a buffer or a pH adjusting agent; typically, the buffer is a salt prepared from an organic acid or base. Representative buffers include organic acid salts, such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers for use in the present compositions are organic acid salts, such as citrate.

Additionally, anti-IL-23 antibody compositions can include polymeric excipients/additives, such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates, such as "TWEEN 20" and "TWEEN 80"), lipids (e.g., phospholipids, fatty acids), steroids (e.g., cholesterol), and chelating agents (e.g., EDTA).

These and additional known pharmaceutical excipients and/or additives suitable for use in the anti-IL-23 antibody, portion or variant compositions according to the invention are known in the art, e.g., as listed in "Remington: The Science & Practice of Pharmacy," $19^{th}$ ed., Williams & Williams, (1995), and in the "Physician's Desk Reference," $52^{nd}$ ed., Medical Economics, Montvale, N.J. (1998), the disclosures of which are entirely incorporated herein by reference. Preferred carrier or excipient materials are carbohydrates (e.g., saccharides and alditols) and buffers (e.g., citrate) or polymeric agents. An exemplary carrier molecule is the mucopolysaccharide, hyaluronic acid, which may be useful for intraarticular delivery.

Formulations

As noted above, the invention provides for stable formulations, which preferably comprise a phosphate buffer with saline or a chosen salt, as well as preserved solutions and formulations containing a preservative as well as multi-use preserved formulations suitable for pharmaceutical or veterinary use, comprising at least one anti-IL-23 antibody in a pharmaceutically acceptable formulation. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3, 0.4, 0.5, 0.9, 1.0%), 0.1-3% benzyl alcohol (e.g., 0.5, 0.9, 1.1, 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

As noted above, the method of the invention uses an article of manufacture, comprising packaging material and at least one vial comprising a solution of at least one anti-IL-23 specific antibody with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further uses an article of manufacture, comprising packaging material, a first vial comprising lyophilized anti-IL-23 specific antibody, and a second vial comprising an aqueous diluent of prescribed buffer or preservative, wherein said packaging material comprises a label that instructs a patient to reconstitute the anti-IL-23 specific antibody in the aqueous diluent to form a solution that can be held over a period of twenty-four hours or greater.

The anti-IL-23 specific antibody used in accordance with the present invention can be produced by recombinant means, including from mammalian cell or transgenic preparations, or can be purified from other biological sources, as described herein or as known in the art.

The range of the anti-IL-23 specific antibody includes amounts yielding upon reconstitution, if in a wet/dry system, concentrations from about 1.0 μg/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

Preferably, the aqueous diluent optionally further comprises a pharmaceutically acceptable preservative. Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the formulation is a concentration sufficient to yield an anti-microbial effect. Such concentrations are dependent on the preservative selected and are readily determined by the skilled artisan.

Other excipients, e.g., isotonicity agents, buffers, antioxidants, and preservative enhancers, can be optionally and preferably added to the diluent. An isotonicity agent, such as glycerin, is commonly used at known concentrations. A physiologically tolerated buffer is preferably added to provide improved pH control. The formulations can cover a wide range of pHs, such as from about pH 4 to about pH 10, and preferred ranges from about pH 5 to about pH 9, and a most preferred range of about 6.0 to about 8.0. Preferably, the formulations of the present invention have a pH between about 6.8 and about 7.8. Preferred buffers include phosphate buffers, most preferably, sodium phosphate, particularly, phosphate buffered saline (PBS).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) or non-ionic surfactants, such as polysorbate 20 or 80 or poloxamer 184 or 188, Pluronic® polyls, other block copolymers, and chelators, such as EDTA and EGTA, can optionally be added to the formulations or compositions to reduce aggregation. These additives are particularly useful if a pump or plastic container is used to administer the formulation. The presence of pharmaceutically acceptable surfactant mitigates the propensity for the protein to aggregate.

The formulations can be prepared by a process which comprises mixing at least one anti-IL-23 specific antibody and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing the at least one anti-IL-23 specific antibody and preservative in an aqueous diluent is carried out using conventional dissolution and mixing procedures. To prepare a suitable formulation, for example, a measured amount of at least one anti-IL-23 specific antibody in buffered solution is combined with the desired preservative in a buffered solution in quantities sufficient to provide the protein and preservative at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The formulations can be provided to patients as clear solutions or as dual vials comprising a vial of lyophilized anti-IL-23 specific antibody that is reconstituted with a second vial containing water, a preservative and/or excipients, preferably, a phosphate buffer and/or saline and a chosen salt, in an aqueous diluent. Either a single solution vial or dual vial requiring reconstitution can be reused multiple times and can suffice for a single or multiple cycles of patient treatment and thus can provide a more convenient treatment regimen than currently available.

The present articles of manufacture are useful for administration over a period ranging from immediate to twenty-four hours or greater. Accordingly, the presently claimed articles of manufacture offer significant advantages to the patient. Formulations of the invention can optionally be safely stored at temperatures of from about 2° C. to about 40° C. and retain the biologically activity of the protein for extended periods of time, thus allowing a package label indicating that the solution can be held and/or used over a period of 6, 12, 18, 24, 36, 48, 72, or 96 hours or greater. If preserved diluent is used, such label can include use up to 1-12 months, one-half, one and a half, and/or two years.

The solutions of anti-IL-23 specific antibody can be prepared by a process that comprises mixing at least one antibody in an aqueous diluent. Mixing is carried out using conventional dissolution and mixing procedures. To prepare a suitable diluent, for example, a measured amount of at least one antibody in water or buffer is combined in quantities sufficient to provide the protein and, optionally, a preservative or buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed products can be provided to patients as clear solutions or as dual vials comprising a vial of lyophilized at least one anti-IL-23 specific antibody that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available.

The claimed products can be provided indirectly to patients by providing to pharmacies, clinics, or other such institutions and facilities, clear solutions or dual vials comprising a vial of lyophilized at least one anti-IL-23 specific antibody that is reconstituted with a second vial containing the aqueous diluent. The clear solution in this case can be up to one liter or even larger in size, providing a large reservoir from which smaller portions of the at least one antibody solution can be retrieved one or multiple times for transfer into smaller vials and provided by the pharmacy or clinic to their customers and/or patients.

Recognized devices comprising single vial systems include pen-injector devices for delivery of a solution, such as BD Pens, BD Autojector®, Humaject®, NovoPen®, B-D®Pen, AutoPen®, and OptiPen®, GenotropinPen®, Genotronorm Pen®, Humatro Pen®, Reco-Pen®, Roferon Pen®, Biojector®, Iject®, J-tip Needle-Free Injector®, Intraject®, Medi-Ject®, Smartject® e.g., as made or developed by Becton Dickensen (Franklin Lakes, N.J., www.bectondickenson.com), Disetronic (Burgdorf, Switzerland, www.disetronic.com; Bioject, Portland, Oreg. (www.bioject.com); National Medical Products, Weston Medical (Peterborough, UK, www.weston-medical.com), Medi-Ject Corp (Minneapolis, Minn., www.mediject.com), and similary suitable devices. Recognized devices comprising a dual vial system include those pen-injector systems for reconstituting a lyophilized drug in a cartridge for delivery of the reconstituted solution, such as the HumatroPen®. Examples of other devices suitable include pre-filled syringes, auto-injectors, needle free injectors, and needle free IV infusion sets.

The products may include packaging material. The packaging material provides, in addition to the information required by the regulatory agencies, the conditions under which the product can be used. The packaging material of the present invention provides instructions to the patient, as applicable, to reconstitute the at least one anti-IL-23 antibody in the aqueous diluent to form a solution and to use the solution over a period of 2-24 hours or greater for the two vial, wet/dry, product. For the single vial, solution product, pre-filled syringe or auto-injector, the label indicates that such solution can be used over a period of 2-24 hours or greater. The products are useful for human pharmaceutical product use.

The formulations used in the method of the present invention can be prepared by a process that comprises mixing an anti-IL-23 antibody and a selected buffer, preferably, a phosphate buffer containing saline or a chosen salt. Mixing the anti-IL-23 antibody and buffer in an aqueous diluent is carried out using conventional dissolution and mixing procedures. To prepare a suitable formulation, for example, a measured amount of at least one antibody in water or buffer is combined with the desired buffering agent in water in quantities sufficient to provide the protein and buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The method of the invention provides pharmaceutical compositions comprising various formulations useful and acceptable for administration to a human or animal patient. Such pharmaceutical compositions are prepared using water at "standard state" as the diluent and routine methods well known to those of ordinary skill in the art. For example, buffering components such as histidine and histidine monohydrochloride hydrate, may be provided first followed by the addition of an appropriate, non-final volume of water diluent, sucrose and polysorbate 80 at "standard state." Isolated antibody may then be added. Last, the volume of the pharmaceutical composition is adjusted to the desired final volume under "standard state" conditions using water as the diluent. Those skilled in the art will recognize a number of other methods suitable for the preparation of the pharmaceutical compositions.

The pharmaceutical compositions may be aqueous solutions or suspensions comprising the indicated mass of each constituent per unit of water volume or having an indicated pH at "standard state." As used herein, the term "standard state" means a temperature of 25° C.+/−2° C. and a pressure of 1 atmosphere. The term "standard state" is not used in the art to refer to a single art recognized set of temperatures or pressure, but is instead a reference state that specifies temperatures and pressure to be used to describe a solution or suspension with a particular composition under the reference "standard state" conditions. This is because the volume of a solution is, in part, a function of temperature and pressure. Those skilled in the art will recognize that pharmaceutical compositions equivalent to those disclosed here can be produced at other temperatures and pressures. Whether such pharmaceutical compositions are equivalent to those disclosed here should be determined under the "standard state" conditions defined above (e.g. 25° C.+/−2° C. and a pressure of 1 atmosphere).

Importantly, such pharmaceutical compositions may contain component masses "about" a certain value (e.g. "about 0.53 mg L-histidine") per unit volume of the pharmaceutical composition or have pH values about a certain value. A component mass present in a pharmaceutical composition or pH value is "about" a given numerical value if the isolated antibody present in the pharmaceutical composition is able to bind a peptide chain while the isolated antibody is present in the pharmaceutical composition or after the isolated antibody has been removed from the pharmaceutical composition (e.g., by dilution). Stated differently, a value, such as a component mass value or pH value, is "about" a given numerical value when the binding activity of the isolated antibody is maintained and detectable after placing the isolated antibody in the pharmaceutical composition.

Competition binding analysis is performed to determine if the IL-23 specific mAbs bind to similar or different epitopes and/or compete with each other. Abs are individually coated on ELISA plates. Competing mAbs are added, followed by the addition of biotinylated hrIL-23. For positive control, the same mAb for coating may be used as the competing mAb ("self-competition"). IL-23 binding is detected using streptavidin. These results demonstrate whether the mAbs recognize similar or partially overlapping epitopes on IL-23.

One aspect of the method of the invention administers to a patient a pharmaceutical composition comprising In one embodiment of the pharmaceutical compositions, the isolated antibody concentration is from about 77 to about 104 mg per ml of the pharmaceutical composition. In another embodiment of the pharmaceutical compositions the pH is from about 5.5 to about 6.5.

The stable or preserved formulations can be provided to patients as clear solutions or as dual vials comprising a vial of lyophilized at least one anti-IL-23 antibody that is reconstituted with a second vial containing a preservative or buffer and excipients in an aqueous diluent. Either a single solution vial or dual vial requiring reconstitution can be reused multiple times and can suffice for a single or multiple cycles of patient treatment and thus provides a more convenient treatment regimen than currently available.

Other formulations or methods of stabilizing the anti-IL-23 antibody may result in other than a clear solution of lyophilized powder comprising the antibody. Among non-clear solutions are formulations comprising particulate suspensions, said particulates being a composition containing the anti-IL-23 antibody in a structure of variable dimension and known variously as a microsphere, microparticle, nanoparticle, nanosphere, or liposome. Such relatively homogenous, essentially spherical, particulate formulations containing an active agent can be formed by contacting an aqueous phase containing the active agent and a polymer and a nonaqueous phase followed by evaporation of the nonaqueous phase to cause the coalescence of particles from the aqueous phase as taught in U.S. Pat. No. 4,589,330. Porous microparticles can be prepared using a first phase containing active agent and a polymer dispersed in a continuous solvent and removing said solvent from the suspension by freeze-drying or dilution-extraction-precipitation as taught in U.S. Pat. No. 4,818,542. Preferred polymers for such preparations are natural or synthetic copolymers or polymers selected from the group consisting of gleatin agar, starch, arabinogalactan, albumin, collagen, polyglycolic acid, polylactic aced, glycolide-L(–) lactide poly(episilon-caprolactone, poly(epsilon-caprolactone-CO-lactic acid), poly(epsilon-caprolactone-CO-glycolic acid), poly(β-hydroxy butyric acid), polyethylene oxide, polyethylene, poly (alkyl-2-cyanoacrylate), poly(hydroxyethyl methacrylate), polyamides, poly(amino acids), poly(2-hydroxyethyl DL-aspartamide), poly(ester urea), poly(L-phenylalanine/ethylene glycol/1,6-diisocyanatohexane) and poly(methyl methacrylate). Particularly preferred polymers are polyesters, such as polyglycolic acid, polylactic aced, glycolide-L(–) lactide poly(episilon-caprolactone, poly(epsilon-caprolactone-CO-lactic acid), and poly(epsilon-caprolactone-CO-glycolic acid. Solvents useful for dissolving the polymer and/or the active include: water, hexafluoroisopropanol, methylenechloride, tetrahydrofuran, hexane, benzene, or hexafluoroacetone sesquihydrate. The process of dispersing the active containing phase with a second phase may include pressure forcing said first phase through an orifice in a nozzle to affect droplet formation.

Dry powder formulations may result from processes other than lyophilization, such as by spray drying or solvent extraction by evaporation or by precipitation of a crystalline composition followed by one or more steps to remove aqueous or nonaqueous solvent. Preparation of a spray-dried antibody preparation is taught in U.S. Pat. No. 6,019,968. The antibody-based dry powder compositions may be produced by spray drying solutions or slurries of the antibody and, optionally, excipients, in a solvent under conditions to provide a respirable dry powder. Solvents may include polar compounds, such as water and ethanol, which may be readily dried. Antibody stability may be enhanced by performing the spray drying procedures in the absence of oxygen, such as under a nitrogen blanket or by using nitrogen as the drying gas. Another relatively dry formulation is a dispersion of a plurality of perforated microstructures dispersed in a suspension medium that typically comprises a hydrofluoroalkane propellant as taught in WO 9916419. The stabilized dispersions may be administered to the lung of a patient using a metered dose inhaler. Equipment useful in the commercial manufacture of spray dried medicaments are manufactured by Buchi Ltd. or Niro Corp.

An anti-IL-23 antibody in either the stable or preserved formulations or solutions described herein, can be administered to a patient in accordance with the present invention via a variety of delivery methods including SC or IM injection; transdermal, pulmonary, transmucosal, implant, osmotic pump, cartridge, micro pump, or other means appreciated by the skilled artisan, as well-known in the art.

Therapeutic Applications

In one general aspect, the present application provides a method for modulating or treating psoriatic arthritis, in a cell, tissue, organ, animal, or patient, as known in the art or as described herein, using at least one IL-23 antibody of the present invention, e.g., administering or contacting the cell, tissue, organ, animal, or patient with a therapeutic effective amount of IL-23 specific antibody.

Any method of the present invention can comprise administering an effective amount of a composition or pharmaceutical composition comprising an anti-IL-23 antibody to a cell, tissue, organ, animal or patient in need of such modulation, treatment or therapy. Such a method can optionally further comprise co-administration or combination therapy for treating such diseases or disorders, wherein the administering of said at least one anti-IL-23 antibody, specified portion or variant thereof, further comprises administering, before concurrently, and/or after, at least one selected from at least one TNF antagonist (e.g., but not limited to, a TNF chemical or protein antagonist, TNF monoclonal or polyclonal antibody or fragment, a soluble TNF receptor (e.g., p55, p70 or p85) or fragment, fusion polypeptides thereof, or a small molecule TNF antagonist, e.g., TNF binding protein I or II (TBP-1 or TBP-II), nerelimonmab, infliximab, eternacept (Enbrel™), adalimulab (Humira™), CDP-571, CDP-870, afelimomab, lenercept, and the like), an antirheumatic (e.g., methotrexate, auranofin, aurothioglucose, azathioprine, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anesthetic, a neuromuscular blocker, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropoietin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Suitable dosages are well known in the art. See, e.g., Wells et al., eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, C A (2000); Nursing 2001 Handbook of Drugs, $21^{st}$ edition, Springhouse Corp., Springhouse, P A, 2001; Health Professional's Drug Guide 2001, ed., Shannon, Wilson, Stang, Prentice-Hall, Inc, Upper Saddle River, N.J., each of which references are entirely incorporated herein by reference.

Therapeutic Treatments

Typically, treatment of psoriatic arthritis is achieved by administering an effective amount or dosage of an anti-IL-23 antibody composition that total, on average, a range from at least about 0.01 to 500 milligrams of an anti-IL-23 antibody per kilogram of patient per dose, and, preferably, from at least about 0.1 to 100 milligrams antibody/kilogram of patient per single or multiple administration, depending upon the specific activity of the active agent contained in the composition. Alternatively, the effective serum concentration can comprise 0.1-5000 μg/ml serum concentration per single or multiple administrations. Suitable dosages are known to medical practitioners and will, of course, depend upon the particular disease state, specific activity of the composition being administered, and the particular patient undergoing treatment. In some instances, to achieve the desired therapeutic amount, it can be necessary to provide for repeated administration, i.e., repeated individual administrations of a particular monitored or metered dose, where the individual administrations are repeated until the desired daily dose or effect is achieved.

Preferred doses can optionally include 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100-500 mg/kg/administration, or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 µg/ml serum concentration per single or multiple administration, or any range, value or fraction thereof.

Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. Usually a dosage of active ingredient can be about 0.1 to 100 milligrams per kilogram of body weight. Ordinarily 0.1 to 50, and, preferably, 0.1 to 10 milligrams per kilogram per administration or in sustained release form is effective to obtain desired results.

As a non-limiting example, treatment of humans or animals can be provided as a one-time or periodic dosage of at least one antibody of the present invention 0.1 to 100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or, alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or, alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

Dosage forms (composition) suitable for internal administration generally contain from about 0.001 milligram to about 500 milligrams of active ingredient per unit or container. In these pharmaceutical compositions the active ingredient will ordinarily be present in an amount of about 0.5-99.999% by weight based on the total weight of the composition.

For parenteral administration, the antibody can be formulated as a solution, suspension, emulsion, particle, powder, or lyophilized powder in association, or separately provided, with a pharmaceutically acceptable parenteral vehicle. Examples of such vehicles are water, saline, Ringer's solution, dextrose solution, and 1-10% human serum albumin. Liposomes and nonaqueous vehicles, such as fixed oils, can also be used. The vehicle or lyophilized powder can contain additives that maintain isotonicity (e.g., sodium chloride, mannitol) and chemical stability (e.g., buffers and preservatives). The formulation is sterilized by known or suitable techniques.

Suitable pharmaceutical carriers are described in the most recent edition of Remington's Pharmaceutical Sciences, A. Osol, a standard reference text in this field.

Alternative Administration

Many known and developed modes can be used according to the present invention for administering pharmaceutically effective amounts of an anti-IL-23 antibody. While pulmonary administration is used in the following description, other modes of administration can be used according to the present invention with suitable results. IL-23 specific antibodies of the present invention can be delivered in a carrier, as a solution, emulsion, colloid, or suspension, or as a dry powder, using any of a variety of devices and methods suitable for administration by inhalation or other modes described here within or known in the art.

Parenteral Formulations and Administration

Formulations for parenteral administration can contain as common excipients sterile water or saline, polyalkylene glycols, such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent, such as aqueous solution, a sterile injectable solution or suspension in a solvent. As the usable vehicle or solvent, water, Ringer's solution, isotonic saline, etc. are allowed; as an ordinary solvent or suspending solvent, sterile involatile oil can be used. For these purposes, any kind of involatile oil and fatty acid can be used, including natural or synthetic or semisynthetic fatty oils or fatty acids; natural or synthetic or semi-synthtetic mono- or di- or tri-glycerides. Parental administration is known in the art and includes, but is not limited to, conventional means of injections, a gas pressured needle-less injection device as described in U.S. Pat. No. 5,851,198, and a laser perforator device as described in U.S. Pat. No. 5,839,446 entirely incorporated herein by reference.

Alternative Delivery

The invention further relates to the administration of an anti-IL-23 antibody by parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, bolus, vaginal, rectal, buccal, sublingual, intranasal, or transdermal means. An anti-IL-23 antibody composition can be prepared for use for parenteral (subcutaneous, intramuscular or intravenous) or any other administration particularly in the form of liquid solutions or suspensions; for use in vaginal or rectal administration particularly in semisolid forms, such as, but not limited to, creams and suppositories; for buccal, or sublingual administration, such as, but not limited to, in the form of tablets or capsules; or intranasally, such as, but not limited to, the form of powders, nasal drops or aerosols or certain agents; or transdermally, such as not limited to a gel, ointment, lotion, suspension or patch delivery system with chemical enhancers such as dimethyl sulfoxide to either modify the skin structure or to increase the drug concentration in the transdermal patch (Junginger, et al. In "Drug Permeation Enhancement;" Hsieh, D. S., Eds., pp. 59-90

(Marcel Dekker, Inc. New York 1994, entirely incorporated herein by reference), or with oxidizing agents that enable the application of formulations containing proteins and peptides onto the skin (WO 98/53847), or applications of electric fields to create transient transport pathways, such as elec- troporation, or to increase the mobility of charged drugs through the skin, such as iontophoresis, or application of ultrasound, such as sonophoresis (U.S. Pat. Nos. 4,309,989 and 4,767,402) (the above publications and patents being entirely incorporated herein by reference).

Having generally described the invention, the same will be more readily understood by reference to the following Examples, which are provided by way of illustration and are not intended as limiting. Further details of the invention are illustrated by the following non-limiting Examples. The disclosures of all citations in the specification are expressly incorporated herein by reference.

EMBODIMENTS

Embodiment 1 is a method of treating psoriatic arthritis (PsA) in a subject in need thereof, wherein the subject showed an inadequate response to treatment with an anti-TNF therapy (such as an anti-TNFα antibody or other therapy, the method comprising subtaneously administering to the subject a pharmaceutical composition comprising a safe and effective amount of an anti-IL-23 antibody and a pharmaceutically acceptable carrier, wherein the pharmaceutical composition is administered once every 4 four weeks (4w).

Embodiment 1a is the method of embodiment 1, wherein the anti-IL-23 antibody comprises a heavy chain variable region and a light chain variable region, the heavy chain variable region comprising a complementarity determining region heavy chain 1 (CDRH1) amino acid sequence of SEQ ID NO: 1, a CDRH2 of SEQ ID NO: 2, and a CDRH3 of SEQ ID NO: 3; and the light chain variable region com- prising a complementarity determining region light chain 1 (CDRL1) amino acid sequence of SEQ ID NO: 4, a CDRL2 of SEQ ID NO: 5, and a CDRL3 of SEQ ID NO: 6.

Embodiment 1b is the method of embodiment 1, wherein the antibody comprises the heavy chain variable region of the amino acid sequence of SEQ ID NO: 7, and the light chain variable region of the amino acid sequence of SEQ ID NO: 8.

Embodiment 2 is the method of any one of embodiments 1 to 1c, wherein the antibody is administered at a total dosage of 25 mg to 200 mg per administration, such as 25 mg, 50 mg, 75 mg, 100 mg, 125 mg, 150 mg, 175 mg, and 200 mg per administration, or any dosage in between.

Embodiment 2a is the method of embodiment 2, wherein the total dosage is about 50 to about 150 mg per adminis- tration.

Embodiment 2b is the method of embodiment 2, wherein the total dosage is about 100 mg per administration.

Embodiment 3 is the method of any one of embodiments 1 to 2b, wherein the subject has inadequate response to a standard therapy for PsA.

Embodiment 3a is the method of embodiment 3, wherein the standard therapy is at least one selected form the group consisting of non-biological disease-modifying antirheu- matic drugs (DMARDs), oral corticosteroid, apremilast, nonsteroidal anti-inflammatory drugs (NSAIDs).

Embodiment 3b is the method of embodiment 3, wherein the standard therapy is a DMARD selected from the group consisting of methotrexate (MTX) administered to the sub- ject at ≤25 mg/week, sulfasalazine (SSZ) administered to the subject at ≤3 g/day, hydroxychloroquine (HCQ) adminis- tered to the subject at ≤400 mg/day or leflunomide (LEF) administered to the subject at ≤20 mg/day.

Embodiment 3c is the method of embodiment 3, wherein the standard therapy is an oral corticosteroid administered to the subject at an amount equivalent to ≤10 mg/day of prednisone.

Embodiment 3d is the method of embodiment 3, wherein the standard therapy is a NSAID or other analgesic admin- istered to the subject at the marketed dose approved by a regulatory authority.

Embodiment 3e is the method of embodiment 3, wherein the standard therapy is apremilast administered to the sub- ject at the marketed dose approved by a regulatory authority.

Embodiment 3f is the method of any one of embodiments 3 to 3e, wherein the subject is biologic treatment naïve.

Embodiment 3g is the method of any one of embodiments 3 to 3e, wherein the subject has previously received at least one biologic treatment for PsA.

Embodiment 3h is the method of embodiment 3g, wherein the subject has inadequate response to the at least one biologic treatment.

Embodiment 3i is the method of embodiment 3g or 3h, wherein the biologic treatment is selected from the group consisting of guselkumab, ustekinumab, secukinumab (AIN457), anti-tumor necrosis factor alpha (TNFα) agents (such as adalimumab, etanercept, infliximab, golimumab subcutaneous [SC] or intravenous [IV], certolizumab pegol, or their respective biosimilars), tildrakizumab (MK3222), ixekizumab (LY2439821), brodalumab (AMG827), risanki- zumab (BI-655066), or other investigative biologic treat- ment for PsA or psoriasis.

Embodiment 3j is the method of embodiment 3i, wherein the subject is a non-responder to an anti-tumor necrosis factor alpha (TNFα) treatment.

Embodiment 3k is the method of any one of embodiments 1 to 3j, wherein the subject has at least 3% body surface area (BSA) of plaque psoriasis prior to the treatment.

Embodiment 3l is the method of any one of embodiments 1 to 3j, wherein the subject has at least one psoriatic plaque of ≥2 cm diameter or nail changes consistent with psoriasis or documented history of plaque psoriasis prior to the treatment.

Embodiment 3m is the method of any one of embodi- ments 1 to 3l, optionally further comprising administering to the subject a standard therapy for PsA.

Embodiment 3n is the method of any one of embodiments 1 to 3l, optionally further comprising administering to the subject a biologic treatment for PsA.

Embodiment 4 is the method of any one of embodiments 1 to 3n, wherein the subject is a responder to the treatment with the antibody and is identified as having a statistically significant improvement in disease activity, wherein disease activity is determined by one or more criteria selected from the group consisting of a 20% improvement in the American College of Rheumatology core set disease index (ACR20), a 50% improvement in the American College of Rheuma- tology core set disease index (ACR50), a 70% improvement in the American College of Rheumatology core set disease index (ACR70), Health Assessment Questionnaire Disabil- ity Index (HAQ-DI), Investigator's Global Assessment (IGA), Disease Activity Score 28 (DAS28) C-reactive pro- tein (CRP), resolution of enthesitis, resolution of dactylitis, Leeds enthesitis index (LEI), dactylitis assessment score, Short Form Health survey (SF-36) in the mental and physi- cal component summary (MCS and PCS), achievement of minimal disease activity (MDA), and achievement of very low disease activity (VLDA).

Embodiment 4a is the method of embodiment 4, wherein the improvement is measured 16, 20, 24, 28 or 48 weeks after initial treatment.

Embodiment 4b is the method of any one of embodiments 4-4a, wherein the improvement is measured 16 weeks after initial treatment.

Embodiment 4c is the method of any one of embodiments 4-4a, wherein the improvement is measured 24 weeks or 48 weeks after initial treatment.

Embodiment 5 is the method of any one of embodiments 4-4c, wherein the subject is a responder to the treatment with the antibody and is identified as having a statistically significant improvement in disease activity as determined by a 20% improvement in the American College of Rheumatology core set disease index (ACR20) by week 24 or week 48 of treatment with the antibody.

Embodiment 5a is the method of any one of embodiments 4-4c, wherein the subject is a responder to the treatment with the antibody and is identified as having a statistically significant improvement in disease activity as determined by a 20% improvement in the American College of Rheumatology core set disease index (ACR20) by week 16 of treatment with the antibody.

Embodiment 5b is the method of any one of embodiments 4-4c, wherein the subject is a responder to the treatment with the antibody and is identified as having a statistically significant improvement in disease activity as determined by a 50% improvement in the American College of Rheumatology core set disease index (ACR50) by week 24 or week 48 of treatment with the antibody.

Embodiment 5c is the method of any one of embodiments 4-4c, wherein the subject is a responder to the treatment with the antibody and is identified as having a statistically significant improvement in disease activity as determined by a 50% improvement in the American College of Rheumatology core set disease index (ACR50) by week 16 of treatment with the antibody.

Embodiment 5d is the method of any one of embodiments 4-4c, wherein the subject is a responder to the treatment with the antibody and is identified as having a statistically significant improvement in disease activity as determined by a 70% improvement in the American College of Rheumatology core set disease index (ACR70) by week 24 or week 48 of treatment with the antibody.

Embodiment 5e is the method of any one of embodiments 4-4c, wherein the subject is a responder to the treatment with the antibody and is identified as having a statistically significant improvement in disease activity as determined by the Health Assessment Questionnaire Disability Index (HAQ-DI) by week 24 or week 48 of treatment with the antibody.

Embodiment 5f in the method of any one of embodiments 4-4c, wherein the subject is a responder to the treatment with the antibody and is identified as having a statistically significant improvement in disease activity as determined by Disease Activity Score 28 (DAS28) C-reactive protein (CRP) by week 24 or week 48 of treatment with the antibody.

Embodiment 5g in the method of any one of embodiments 4-4c, wherein the subject is a responder to the treatment with the antibody and is identified as achieving Investigator's Global Assessment (IGA) of 0 (clear) or 1 (minimal) and/or ≥2 grade reduction of the IGA from baseline by week 24 of treatment with the antibody, wherein the subject has >=3% BSA psoriatic involvement and an IGA score of >=2 at the baseline.

Embodiment 5h in the method of any one of embodiments 4-4c, wherein the subject is a responder to the treatment with the antibody and is identified as having a statistically significant improvement in disease activity as determined by resolution of enthesitis by week 24 or week 48 of treatment with the antibody.

Embodiment 5i in the method of any one of embodiments 4-4c, wherein the subject is a responder to the treatment with the antibody and is identified as having a statistically significant improvement in disease activity as determined by resolution of dactylitis by week 24 or week 48 of treatment with the antibody.

Embodiment 5j in the method of any one of embodiments 4-4c, wherein the subject is a responder to the treatment with the antibody and is identified as having a statistically significant improvement in disease activity as determined by Leeds enthesitis index (LEI) by week 24 or week 48 of treatment with the antibody.

Embodiment 5k is the method of any one of embodiments 4-4c, wherein the subject is a responder to the treatment with the antibody and is identified as having statistically significant improvement in disease activity as determined by the dactylitis assessment score of 0-3 ((0=absent, 1=mild, 2=moderate, 3=severe) by week 24 or week 48 of treatment with the antibody.

Embodiment 5l is the method of any one of embodiments 4-4c, wherein the subject is a responder to the treatment with the antibody and is identified as having a statistically significant improvement in disease activity as determined by the Short-Form 36 (SF-36) health survey by week 24 or week 48 of treatment with the antibody.

Embodiment 5m is the method of any one of embodiments 4-4c, wherein the subject is a responder to the treatment with the antibody and is identified as having a statistically significant improvement in disease activity as determined by the mental and physical component summary (MCS and PCS) scores by week 24 or week 48 of treatment with the antibody.

Embodiment 5n is the method of any one of embodiments 4-4c, wherein the subject is a responder to the treatment with the antibody and is identified as having a statistically significant improvement in disease activity as determined by the minimal disease activity (MDA) criteria by week 24 or week 48 of treatment with the antibody.

Embodiment 5o is the method of any one of embodiments 4-4c, wherein the subject is a responder to the treatment with the antibody and is identified as having a statistically significant improvement in disease activity as determined by achievement of very low disease activity (VLDA).

Embodiment 6 is the method of any one of embodiments 4-5o, wherein the improvement is maintained for at least 12 weeks, 24 weeks, 36 weeks, 48 weeks, 60 weeks, 72 weeks, or 84 weeks, or any time in between.

Embodiment 7 is the method of any one of embodiments 1-6, wherein the anti-IL-23 antibody is guselkumab.

Embodiment 8 is the method of any one of embodiments 1-7, further comprising administering to the subject one or more additional drugs used to treat psoriasis arthritis.

Embodiment 8a is the method of embodiment 8, wherein the additional drug is selected from the group consisting of: immunosuppressive agents, non-steroidal anti-inflammatory drugs (NSAIDs), methotrexate (MTX), anti-B-cell surface marker antibodies, anti-CD20 antibodies, rituximab, TNF-inhibitors, corticosteroids, and co-stimulatory modifiers.

Embodiment 9 is a method of treating psoriatic arthritis (PsA) in a subject, the method comprising subtaneously administering to the subject a pharmaceutical composition comprising a safe and effective amount of an anti-IL-23 antibody and a pharmaceutically acceptable carrier, wherein the pharmaceutical composition is administered at an initial dose, a dose 4 weeks thereafter, and at a dosing interval of once every 8 weeks (q8w) thereafter, and wherein the subject has at least one psoriatic plaque of ≥2 cm diameter or nail changes consistent with psoriasis or documented history of plaque psoriasis before the treatment.

Embodiment 9a is the method of embodiment 9, wherein the anti-IL-23 antibody comprises a heavy chain variable region and a light chain variable region, the heavy chain variable region comprising a complementarity determining region heavy chain 1 (CDRH1) amino acid sequence of SEQ ID NO: 1, a CDRH2 of SEQ ID NO: 2, and a CDRH3 of SEQ ID NO: 3; and the light chain variable region comprising a complementarity determining region light chain 1 (CDRL1) amino acid sequence of SEQ ID NO: 4, a CDRL2 of SEQ ID NO: 5, and a CDRL3 of SEQ ID NO: 6.

Embodiment 9b is the method of embodiment 9, wherein the antibody comprises the heavy chain variable region of the amino acid sequence of SEQ ID NO: 7, and the light chain variable region of the amino acid sequence of SEQ ID NO: 8.

Embodiment 9c is the method of embodiment 9, wherein the anti-IL-23 antibody comprises the heavy chain amino acid sequence of SEQ ID NO: 9, and the light chain amino acid sequence of SEQ ID NO: 10.

Embodiment 10 is the method of any one of embodiments 9 to 9c, wherein the antibody is administered at a total dosage of 25 mg to 200 mg per administration, such as 25 mg, 50 mg, 75 mg, 100 mg, 125 mg, 150 mg, 175 mg, and 200 mg per administration, or any dosage in between.

Embodiment 10a is the method of embodiment 10, wherein the total dosage is about 50 to about 150 mg per administration.

Embodiment 10b is the method of embodiment 10, wherein the total dosage is about 100 mg per administration.

Embodiment 11 is the method of any one of embodiments 9 to 10b, wherein the subject has inadequate response to a standard therapy for PsA.

Embodiment 11a is the method of embodiment 11, wherein the standard therapy is at least one selected form the group consisting of non-biological disease-modifying anti-rheumatic drugs (DMARDs), oral corticosteroid, apremilast, nonsteroidal anti-inflammatory drugs (NSAIDs).

Embodiment 11b is the method of embodiment 11, wherein the standard therapy is a DMARD selected from the group consisting of methotrexate (MTX) administered to the subject at ≤25 mg/week, sulfasalazine (SSZ) administered to the subject at ≤3 g/day, hydroxychloroquine (HCQ) administered to the subject at ≤400 mg/day or leflunomide (LEF) administered to the subject at ≤20 mg/day.

Embodiment 11c is the method of embodiment 11, wherein the standard therapy is an oral corticosteroid administered to the subject at an amount equivalent to ≤10 mg/day of prednisone.

Embodiment 11d is the method of embodiment 11, wherein the standard therapy is a NSAID or other analgesic administered to the subject at the marketed dose approved by a regulatory authority.

Embodiment 11e is the method of embodiment 11, wherein the standard therapy is apremilast administered to the subject at the marketed dose approved by a regulatory authority.

Embodiment 11f is the method of any one of embodiments 11 to 11e, wherein the subject is biologic treatment naïve.

Embodiment 11g is the method of any one of embodiments 11 to 11e, wherein the subject has previously received at least one biologic treatment for PsA.

Embodiment 11h is the method of embodiment 11g, wherein the subject has inadequate response to the at least one biologic treatment.

Embodiment 11i is the method of embodiment 11g or 11h, wherein the biologic treatment is selected from the group consisting of guselkumab, ustekinumab, secukinumab (AIN457), anti-tumor necrosis factor alpha (TNFα) agents (such as adalimumab, etanercept, infliximab, golimumab subcutaneous [SC] or intravenous [IV], certolizumab pegol, or their respective biosimilars), tildrakizumab (MK3222), ixekizumab (LY2439821), brodalumab (AMG827), risankizumab (BI-655066), or other investigative biologic treatment for PsA or psoriasis.

Embodiment 11j is the method of embodiment 11i, wherein the subject is a non-responder to an anti-tumor necrosis factor alpha (TNFα) treatment.

Embodiment 11k is the method of any one of embodiments 9 to 11j, wherein the subject has at least 3% body surface area (BSA) of plaque psoriasis prior to the treatment.

Embodiment 11l is the method of any one of embodiments 9 to 11j, wherein the subject has at least one psoriatic plaque of ≥2 cm diameter or nail changes consistent with psoriasis or documented history of plaque psoriasis prior to the treatment.

Embodiment 11m is the method of any one of embodiments 9 to 11l, optionally further comprising administering to the subject a standard therapy for PsA.

Embodiment 11n is the method of any one of embodiments 9 to 11l, optionally further comprising administering to the subject a biologic treatment for PsA.

Embodiment 12 is the method of any one of embodiments 9 to 11n, wherein the subject is a responder to the treatment with the antibody and is identified as having a statistically significant improvement in disease activity, wherein disease activity is determined by one or more criteria selected from the group consisting of a 20% improvement in the American College of Rheumatology core set disease index (ACR20), a 50% improvement in the American College of Rheumatology core set disease index (ACR50), a 70% improvement in the American College of Rheumatology core set disease index (ACR70), Health Assessment Questionnaire Disability Index (HAQ-DI), Investigator's Global Assessment (IGA), Disease Activity Score 28 (DAS28) C-reactive protein (CRP), resolution of enthesitis, resolution of dactylitis, Leeds enthesitis index (LEI), dactylitis assessment score, Short Form Health survey (SF-36) in the mental and physical component summary (MCS and PCS), achievement of minimal disease activity (MDA), and achievement of very low disease activity (VLDA).

Embodiment 12a is the method of embodiment 12, wherein the improvement is measured 16, 20, 24 or 28 weeks after initial treatment.

Embodiment 12b is the method of any one of embodiments 12-12a, wherein the improvement is measured 16 weeks after initial treatment.

Embodiment 12c is the method of any one of embodiments 12-12a, wherein the improvement is measured 24 weeks after initial treatment.

Embodiment 13 is the method of any one of embodiments 12-12c, wherein the subject is a responder to the treatment with the antibody and is identified as having a statistically significant improvement in disease activity as determined by a 20% improvement in the American College of Rheumatology core set disease index (ACR20) by week 24 or week 48 of treatment with the antibody.

Embodiment 13a is the method of any one of embodiments 12-12c, wherein the subject is a responder to the treatment with the antibody and is identified as having a statistically significant improvement in disease activity as determined by a 20% improvement in the American College of Rheumatology core set disease index (ACR20) by week 16 of treatment with the antibody.

Embodiment 13b is the method of any one of embodiments 12-12c, wherein the subject is a responder to the treatment with the antibody and is identified as having a statistically significant improvement in disease activity as determined by the American College of Rheumatology 130% improvement criteria (ACRβ0) by week 24 or week 48 of treatment with the antibody.

Embodiment 13c is the method of any one of embodiments 12-12c, wherein the subject is a responder to the treatment with the antibody and is identified as having a statistically significant improvement in disease activity as determined by the American College of Rheumatology 130% improvement criteria (ACR130) by week 16 of treatment with the antibody.

Embodiment 13d is the method of any one of embodiments 12-12c, wherein the subject is a responder to the treatment with the antibody and is identified as having a statistically significant improvement in disease activity as determined by the A 70% improvement in the American College of Rheumatology core set disease index (ACR70) by week 24 or week 48 of treatment with the antibody.

Embodiment 13e is the method of any one of embodiments 12-12c, wherein the subject is a responder to the treatment with the antibody and is identified as having a statistically significant improvement in disease activity as determined by the Health Assessment Questionnaire Disability Index (HAQ-DI) by week 24 or week 48 of treatment with the antibody.

Embodiment 13f in the method of any one of embodiments 12-12c, wherein the subject is a responder to the treatment with the antibody and is identified as having a statistically significant improvement in disease activity as determined by Disease Activity Score 28 (DAS28) C-reactive protein (CRP) by week 24 or week 48 of treatment with the antibody.

Embodiment 13g in the method of any one of embodiments 12-12c, wherein the subject is a responder to the treatment with the antibody and is identified as achieving Investigator's Global Assessment (IGA) of 0 (clear) or 1 (minimal) and/or ≥2 grade reduction from baseline by week 24 of treatment with the antibody, wherein the subject has >=3% BSA psoriatic involvement and an IGA score of >=2 at the baseline.

Embodiment 13h in the method of any one of embodiments 12-12c, wherein the subject is a responder to the treatment with the antibody and is identified as having a statistically significant improvement in disease activity as determined by resolution of enthesitis by week 24 or week 48 of treatment with the antibody.

Embodiment 13i in the method of any one of embodiments 12-12c, wherein the subject is a responder to the treatment with the antibody and is identified as having a statistically significant improvement in disease activity as determined by resolution of dactylitis by week 24 or week 48 of treatment with the antibody.

Embodiment 13j in the method of any one of embodiments 12-12c, wherein the subject is a responder to the treatment with the antibody and is identified as having a statistically significant improvement in disease activity as determined by Leeds enthesitis index (LEI) by week 24 or week 48 of treatment with the antibody.

Embodiment 13k is the method of any one of embodiments 12-12c, wherein the subject is a responder to the treatment with the antibody and is identified as having statistically significant improvement in disease activity as determined by the dactylitis assessment score of 0-3 ((0=absent, 1=mild, 2=moderate, 3=severe) by week 24 of treatment with the antibody.

Embodiment 13l is the method of any one of embodiments 12-12c, wherein the subject is a responder to the treatment with the antibody and is identified as having a statistically significant improvement in disease activity as determined by the Short-Form 36 (SF-36) health survey by week 24 or week 48 of treatment with the antibody.

Embodiment 13m is the method of any one of embodiments 12-12c, wherein the subject is a responder to the treatment with the antibody and is identified as having a statistically significant improvement in disease activity as determined by the mental and physical component summary (MCS and PCS) scores by week 24 or week 48 of treatment with the antibody.

Embodiment 13n is the method of any one of embodiments 12-12c, wherein the subject is a responder to the treatment with the antibody and is identified as having a statistically significant improvement in disease activity as determined by the minimal disease activity (MDA) criteria by week 24 or week 48 of treatment with the antibody.

Embodiment 13o is the method of any one of embodiments 12-12c, wherein the subject is a responder to the treatment with the antibody and is identified as having a statistically significant improvement in disease activity as determined by achievement of very low disease activity (VLDA).

Embodiment 14 is the method of any one of embodiments 12-13o, wherein the improvement is maintained for at least 12 weeks, 24 weeks, 36 weeks, 48 weeks, 60 weeks, 72 weeks, or 84 weeks, or any time in between.

Embodiment 15 is the method of any one of embodiments 9-14, wherein the anti-IL-23 antibody is guselkumab.

Embodiment 16 is the method of any one of embodiments 9-15, further comprising administering to the subject one or more additional drugs used to treat psoriasis arthritis.

Embodiment 16a is the method of embodiment 16, wherein the additional drug is selected from the group consisting of: immunosuppressive agents, non-steroidal anti-inflammatory drugs (NSAIDs), methotrexate (MTX), anti-B-cell surface marker antibodies, anti-CD20 antibodies, rituximab, TNF-inhibitors, corticosteroids, and co-stimulatory modifiers.

EXAMPLES

List of Abbreviations and Definitions of Terms

ACR American college of rheumatology
AE Adverse event
ALT Alanine aminotransferase
AST Aspartate aminotransferase
BSA Body surface area
BMI Body mass index
CASPAR Classification criteria for psoriatic arthritis
CMH Cochran-Mantel-Haenszel 43 44

CRF Case report form(s)
CRP C-reactive protein
CSR Clinical study report
DAPSA Disease activity in psoriatic arthritis
DAS28 CRP Disease activity score 28-joint count with
C-reactive protein
DLQI Dermatology life quality index
DMARD Disease-modifying antirheumatic drug
DRC Data review committee
eC-SSRS Electronic Columbia-suicide severity rating scale
eDC Electronic data capture
FACIT Functional assessment of chronic illness therapy
GCP Good clinical practice
HAQ-DI Health assessment questionnaire-disability index
HCQ Hydroxychloroquine
HIV Human immunodeficiency virus
ICF Informed consent form
IEC Independent ethics committee
IGA Investigator's global assessment
IL-23 Interleukin 23
IV Intravenous(ly)
IWRS Interactive web response system
JAK Janus kinase
LEF Leflunomide
LEI Leeds enthesitis index
LS Least squares (mean)
MCS Mental component summary
MDA Minimal disease activity
MedDRA Medical dictionary for regulatory activities
MI Multiple imputation
MMRM Mixed model for repeated measures
MTX Methotrexate
NSAID Nonsteroidal anti-inflammatory drug
PsARC Psoriatic arthritis response criteria
PASDAS Psoriatic arthritis disease activity score
PASI Psoriatic area and severity index
PCS Physical component summary
PFS-U Prefilled syringe with UltraSafe PLUS™ Passive
Needle Guard
PRO Patient-reported outcome(s)
PsA Psoriatic arthritis
q8w Every 8 weeks
SAE Serious adverse event
SC Subcutaneous(ly)
SF-36 36-item short-form health survey
SPARCC Spondyloarthritis research consortium of Canada
SSZ Sulfasalazine
TB Tuberculosis
TEAE Treatment-emergent adverse events
TF Treatment failure
TNFα Tumor necrosis factor alpha
VAS Visual analog scale
VLDA Very low disease activity
WBC White blood cell Example 1: A Phase 3b, Multicenter, Randomized,
Double-Blind, Placebo-Controlled Study to
Evaluate the Efficacy and Safety of Guselkumab
Administered Subcutaneously in Participants with
Active Psoriatic Arthritis and an Inadequate
Response to Anti-Tumor Necrosis Factor
(COSMOS)

Objectives:
The primary objective of this study was to evaluate
guselkumab efficacy versus placebo in participants with
active PsA and an inadequate response to anti-TNFα therapy by assessing the reduction in signs and symptoms of joint
disease. The primary endpoint was the proportion of participants who achieve an American College of Rheumatology (ACR) 20 response at Week 24.
The secondary objectives were to assess the efficacy of
guselkumab versus placebo in improving physical function,
improving general and disease-specific health-related quality-of-life and patient-reported health outcomes, and
improving psoriatic skin lesions. The safety and tolerability
of guselkumab among participants who received at least one
dose of the intervention was also a key secondary objective
of the study.
Methodology:
This is a Phase 3b randomized, double-blind, placebo-controlled, multicenter, 2-arm study conducted to evaluate
guselkumab in participants with active PsA who had an
inadequate response or were intolerant to 1 or 2 anti-TNFα
treatments. The study comprised a placebo-controlled period
from Week 0 to Week 24, an active treatment phase from
Week 24 to Week 48 (with the last dose of study intervention
at Week 44), and a 12-week safety follow-up period from
Week 44 through Week 56. At the time of this report, the
study is ongoing; however, the placebo-controlled period
from Week 0 to Week 24 has completed and is reported.
Number of Participants (Planned and Analyzed):
The planned total sample size to achieve 90% power to
detect a statistically significant treatment difference on the
primary endpoint was approximately 245 participants (163
in the guselkumab group and 82 in the placebo group). At
Week 0, a total of 285 participants were randomized to
receive study intervention; 96 participants were randomized
to receive placebo and 189 participants were randomized to
receive guselkumab in a 2:1 ratio, using permuted block
randomization stratified at the study level by baseline non-biologic DMARD use (yes/no) and by prior exposure to 1 or
2 anti-TNFα agents.
Group I: Guselkumab SC 100 mg administered at Weeks
0 and 4 and then every 8 weeks (Weeks 12, 20, 28, 36)
through Week 44, with placebo SC administered at
Week 24 to maintain the blind.
Group II: Placebo SC administered at Weeks 0, 4, 12, and
20, crossing over at Week 24 to guselkumab SC 100 mg
administered at Weeks 24, 28, 36, and 44.
The planned treatment duration in the study is 44 weeks,
24 weeks in the double-blind treatment period and 20 weeks
in the active treatment phase.
Diagnosis and Main Criteria for Inclusion:
Eligible participants must have had ≥3 tender and >3
swollen joints and an inadequate response or intolerance to
anti-TNFα therapy, defined as the presence of active PsA (as
assessed by the investigator) despite previous treatment with
either 1 or 2 anti-TNFα agents. Stable doses of selected
non-biologic DMARDs (MTX, SSZ, HCQ, LEF), oral corticosteroids (up to 10 mg/d of prednisone or equivalent), and
NSAIDs/analgesics were permitted but not required.
Test Product Dose and Mode of Administration:
All study interventions (guselkumab and placebo) were
administered via SC injection. Participants in the placebo
arm received placebo at Weeks 0 and 4 and then every 8
weeks to Week 20, crossing over at Week 24 to receive SC
guselkumab 100 mg at Week 24, Week 28 and then every 8
weeks through Week 44. Participants in the guselkumab arm
received a guselkumab regimen of 100 mg at Weeks 0 and
4 and then every 8 weeks.
Early Escape:
At Week 16, participants with <5% improvement from
baseline in both tender and swollen joint counts qualified for Early Escape (EE). At any time after Early Escape, participants could initiate or increase the dose of one of the permitted concomitant medications up to the maximum allowed dose as specified in the protocol. Participants in the guselkumab group who qualified for Early Escape received placebo at Week 16 and guselkumab at Week 20, then guselkumab every 8 weeks with no change in the number and frequency of planned guselkumab doses. Participants in the placebo group who qualified for Early Escape would receive guselkumab at Weeks 16 and 20, then guselkumab every 8 weeks.

Duration of Treatment:

The planned treatment duration in the study is 44 weeks, 24 weeks in the double-blind treatment period and 20 weeks in the active treatment phase. The study will remain blinded to the initial treatment assignment till the final database lock. The efficacy and safety of guselkumab through to Week 24 are detailed in this clinical study report.

Criteria for Evaluation:

Evaluations for arthritis included joint assessments (swollen and tender joint counts), participant's assessment of pain, participant's global assessment of disease activity (arthritis), and physician's global assessment of disease activity on visual analogue scales (VAS). Dactylitis and enthesitis were also evaluated. Key efficacy measures of PsA response at Week 24 included ACR responses and HAQ-DI scores.

Given the diverse and highly individual nature of domain involvement in PsA (e.g., skin/nail disease, peripheral arthritis, dactylitis/enthesitis, axial disease), composite indices have been developed to more comprehensively assess disease activity and potentially identify agents with robust efficacy across all manifestations. The activity indices include the Psoriatic ArthritiS Disease Activity Score (PAS-DAS), GRAppa Composite scorE (GRACE), the Composite Psoriatic Disease Activity Index (CPDAI), Psoriatic Arthritis Response Criteria (PsARC), and Disease Activity index for PSoriatic Arthritis (DAPSA). Disease states can be used to describe overall disease status, e.g. DAPSA remission, Minimal Disease Activity (MDA) or Very Low Disease Activity (VLDA).

Psoriasis response was evaluated based on the Investigator's Global Assessment (IGA) of psoriasis, the Dermatology Life Quality Index (DLQI), and the Psoriasis Area and Severity Index (PAST). Other patient-reported outcomes were the SF-36 questionnaire, and the Functional Assessment of Chronic Illness Therapy (FACIT)-Fatigue, along with the participants' Global Assessments of joint, skin and pain burden.

Safety assessments included adverse events (AEs), serious adverse events (SAEs), injection site and allergic reactions, clinical laboratory parameters (hematology and chemistry; urine pregnancy test), electronic Columbia-Suicide Severity Rating Scale (eC-SSRS), physical examinations, vital signs, electrocardiogram (ECG; Week 0 only), and early detection of tuberculosis (TB).

Inclusion Criteria

Participants must have met the following key inclusion criteria to be enrolled in the study:

Be a man or a woman at least 18 years of age (or the legal age of consent in the jurisdiction in which the study is taking place).

Have a diagnosis of PsA for at least 6 months before the first administration of study intervention and meet ClASsification criteria for Psoriatic ARthritis (CASPAR) at screening.

Have active PsA, defined by A swollen joints and A tender joints at screening and baseline.

Have at least 1 of the PsA subsets: distal interphalangeal joint involvement, polyarticular arthritis with absence of rheumatoid nodules, arthritis mutilans, asymmetric peripheral arthritis, or spondylitis with peripheral arthritis.

Have active plaque psoriasis, with at least one psoriatic plaque of $\geq 2$ cm diameter or nail changes consistent with psoriasis or documented history of plaque psoriasis.

Have an inadequate response to anti-TNFα therapy, defined as presence of active PsA despite previous treatment with either 1 or 2 anti-TNFα agents and either of the following:

Lack of benefit of an anti-TNFα therapy after at least 12 weeks of etanercept, adalimumab, golimumab, or certolizumab pegol therapy (or biosimilars) and/or at least a 14-week dosage regimen of infliximab (or biosimilar).

Intolerance to the anti-TNFα therapy etanercept, adalimumab, golimumab, certolizumab pegol, or infliximab (or biosimilars).

If currently using non-biologic DMARDs (limited to MTX, SSZ, HCQ, or LEF) participants should have received treatment at least 3 months before first administration of study intervention; the dose must be stable for at least 4 weeks before first administration of study intervention and no serious toxic side effects should be attributable to the non-biologic DMARD. If currently not using MTX, SSZ, or HCQ, must not have been receiving for at least 4 weeks before first administration of study intervention. If currently not using LEF, must not have been receiving for at least 12 weeks before first administration of study intervention.

If using MTX, the route of administration and dose must be stable and the dose must have been $\leq 25$ mg/week; if receiving SSZ, the dose must have been $\leq 3$g/day; if receiving HCQ, the dose must have been $\leq 400$ mg/day; if receiving LEF, the dose must have been $\leq 20$ mg/day.

If currently using NSAIDs or other analgesics for PsA, participants must have been on a stable dose for at least 2 weeks before first administration of study intervention. If currently not using NSAIDs or other analgesics for PsA, must not have received NSAIDs or other analgesics for PsA within 2 weeks before first administration of study intervention.

If currently using oral corticosteroids for PsA, participants must have been on a stable dose equivalent to $\leq 10$ mg/day of prednisone for at least 2 weeks before first administration of study intervention. If currently not using oral corticosteroids, participants must not have received oral corticosteroids within 2 weeks before first administration of study intervention.

Exclusion Criteria

Participants who met any of the following key exclusion criteria were to be excluded from participating in the study:

Had other inflammatory diseases that might confound the evaluations of benefit of guselkumab therapy, including but not limited to RA, axial spondyloarthritis (this does not include a primary diagnosis of PsA with concomitant spondylitis), systemic lupus erythematosus, or Lyme disease.

Had ever received more than 2 different anti-TNFα agents.

Had received an anti-TNFα agent within the following timeframes prior to first study intervention administration:

Infliximab (or biosimilar), golimumab IV—within 8 weeks

Golimumab SC, adalimumab (or biosimilar), certolizumab pegol—within 6 weeks

Etanercept (or biosimilar)—within 4 weeks

Had previously been treated with guselkumab.

Had previously received any biologic treatment (other than anti-TNFα agents).

Had previously received tofacitinib, baricitinib, filgotinib, peficitinib (ASP015K), decernotinib (VX-509), or any other JAK inhibitor.

Had previously received any systemic immunosuppressants within 4 weeks of the first administration of study intervention.

Had received non-biologic DMARDs (other than MTX, SSZ, HCQ, LEF) within 4 weeks before the first administration of study intervention.

Was receiving 2 or more (specified) non-biologic DMARDs at baseline.

Had received apremilast within 4 weeks prior to the first administration of study intervention.

Had received phototherapy or any systemic medications/treatments that could affect psoriasis evaluations within 4 weeks of the first administration of study intervention.

Had used topical medications/treatments that could affect psoriasis evaluations within 2 weeks of the first administration of any study intervention.

Had received epidural, intra-articular, intramuscular, or IV corticosteroids during the 4 weeks before first administration of study intervention.

Had received lithium within 4 weeks of the first administration of any study intervention.

Had received an experimental antibody or biologic therapy (other than the anti-TNFα agents described in inclusion criteria) or received any other experimental therapy within 90 days or 5 half-lives (whichever is longer) before the first administration of study intervention or was currently enrolled in another study using an investigational agent or procedure.

Had a history or current signs or symptoms of severe, progressive, or uncontrolled renal, hepatic, cardiac, vascular, pulmonary, gastrointestinal, endocrine, neurologic, hematologic, rheumatologic (except PsA), psychiatric, genitourinary, or metabolic disturbances.

Had unstable suicidal ideation or suicidal behavior in the last 6 months and was confirmed to be at risk by the investigator based on an evaluation by a mental health professional.

Study Intervention Information

Guselkumab was supplied for this study as a sterile liquid for SC injection in a single-use prefilled syringe assembled with the UltraSafe PLUS™ Passive Needle Guard (PFS-U); the product does not contain preservatives. Each single-use PFS-U contained 100 mg guselkumab in a 1 mL solution. Placebo was supplied as a sterile liquid for SC injection in a PFS-U. Each single-use PFS-U contained 1 mL solution. Supplies of guselkumab and placebo were to be stored refrigerated from 2° C. to 8° C. and protected from exposure to light.

Randomization and Blinding

Randomization

Central randomization was implemented in this study. At Week 0, participants were randomized in a 2:1 ratio to receive guselkumab and placebo, respectively, based on a computer-generated randomization schedule. Randomization was balanced based on a permuted block randomization method and stratified by baseline non-biologic DMARD use (yes or no) and by prior exposure to anti-TNFα agents (yes or no). The interactive web response system (IWRS) assigned a unique intervention code, which dictated the intervention assignment and matching study intervention for the participant.

Blinding

Participants were assigned randomization numbers at the baseline visit, which were used to instruct the site in the dispensing of medication kits for each participant. The randomization codes were maintained within the Interactive Web Response System (IWRS). The investigator was not provided with the randomization codes. To maintain the study blind, the study intervention container had a multipart label that contained the appropriate regulatory requirements for clinical supplies while not identifying the study intervention contained therein.

The blind for treatment assignment was only to be broken if specific emergency treatment would have been influenced by knowledge of the participant's treatment assignment.

Sponsor personnel who were unblinded to patient-level data at the Week 24 database lock for data analyses and clinical study reporting were documented prior to that database lock. All site personnel and participants were to remain blinded to treatment assignments until the final database lock.

Dosage and Administration

All study interventions (guselkumab and placebo) were administered through subcutaneous (SC) injection. A guselkumab dose regimen of 100 mg at Weeks 0 and 4 and then every 8 weeks (q8w) was selected for this study, based on the evaluation of this dose regimen in the Phase 2 study in PsA (CNTO1959PSA2001) and Phase 3 studies in psoriasis.

In the CNTO1959PSA2001 study, robust efficacy and clinically meaningful improvement was observed with this dose regimen in all important domains of PsA including joint signs and symptoms, physical function, psoriasis, enthesitis, dactylitis, and quality of life in patients with active PsA and ≥3% BSA of psoriasis. Additionally, significant benefit was also observed with this dose regimen on plaque psoriasis in patients with moderate-to-severe psoriasis in the Phase 3 psoriasis studies. In the Phase 3 PsA studies, an additional dose regimen was included (every 4 weeks; q4w). However, this dose regimen was not expected to result in substantially higher levels of efficacy than would be achieved by q8w dosing during maintenance.

The safety of this q8w dose regimen has been established in a large psoriasis development program. Furthermore, the safety profile in the Phase 2 studies in patients with PsA and RA is consistent with that seen in the psoriasis program. The results of the Phase 3 PsA program were not available at the time of the design of the current study.

Participants in the placebo arm received placebo at Weeks 0 and 4 and then every 8 weeks to Week 20, crossing over at Week 24 to receive SC guselkumab 100 mg at Week 24, Week 28 and then every 8 weeks through Week 44. Study intervention was to be administered at the study site by a health care professional (HCP) at Week 0 and Week 4. Beginning at Week 12, at the discretion of the investigator and participant, and after appropriate and documented training, participants had the option to self-administer study agent at the investigative site under the supervision of an HCP or continue to have study agent injections performed by an HCP. To limit the impact of the COVID-19 pandemic, the protocol was amended to allow subcutaneous injections of study intervention to be self-administered outside a study site after Week 24, in cases where a site visit was not possible in view of national, regional or local restrictions. Since this was only relevant after Week 24, this could not have influenced the results reported in this document. All visits up to the Week 24 time point were conducted within the appropriate time frames as originally scheduled for the study (exceptions reported as major protocol deviations).

The following key efficacy evaluations were performed to assess the signs and symptoms of PsA in relation to the primary and secondary endpoints of the study.

Joint Assessments: Each of 68 joints were evaluated for tenderness, and each of 66 joints were evaluated for swelling (hips were excluded since not evaluable for swelling) by a designated independent joint assessor (IJA) who was not involved in any other study conduct except performing joint assessments as well as enthesitis and dactylitis assessments. A joint was only to be designated as "non-evaluable" by the IJA if it was physically impossible to assess the joint.

Patient's assessment of pain: Participants were asked to assess their average pain during the past week on a 100 mm visual analog scale (VAS), with the left end indicating "no pain" and the right end indicating "the worst possible pain."

Patient's global assessment of disease activity (arthritis and psoriasis): Participants were asked to rate how they felt during the past week regarding their psoriasis and arthritis on a 100 mm VAS, with the left end indicating "Excellent" and the right end indicating "Poor."

Patient's global assessment of disease activity (arthritis): Participants were asked to rate how they felt during the past week regarding their arthritis on a 100 mm VAS, with the left end indicating "Excellent" and the right end indicating "Poor."

Physician's global assessment of disease activity: The physician was asked to assess the patient's arthritis on a 100 mm VAS, with the left end indicating "No arthritis activity" and the right end indicating "Extremely active arthritis."

American College of Rheumatology (ACR) responses: ACR 20 was defined as ≥20% improvement from baseline in both swollen joint count (66 joints) and tender joint count (68 joints), and >20% improvement from baseline in 3 of the following 5 assessments: patient's assessment of pain on a VAS, global assessment of disease activity (arthritis, patient and physician VAS), physician's global assessment of disease activity (VAS), HAQ-DI, and CRP. ACR 50 and ACR 70 were similarly defined except improvement threshold from baseline is 50% and 70%, respectively.

Health Assessment Questionnaire-Disability Index (HAQ-DI): A 20-question instrument that assessed the degree of difficulty a person had in accomplishing tasks in 8 functional areas (dressing, arising, eating, walking, hygiene, reaching, gripping, and activities of daily living). Responses in each functional area were scored from 0, indicating no difficulty, to 3, indicating inability to perform a task in that area (ie, lower scores are indicative of better functioning). In PsA, a decrease in score of 0.35 has been determined to indicate a clinically meaningful improvement.

C-reactive protein (CRP): The serum concentration of CRP, a biomarker for overall inflammation burden, was measured by high-sensitivity method in the central laboratory.

Patient's assessment of skin disease activity: Participants were asked to rate how they felt during the past week regarding their psoriasis on a 100 mm VAS, with the left end indicating "Excellent" and the right end indicating "Poor."

Body surface area (BSA) of psoriasis: The BSA of psoriasis was measured at Week 0 using the palm method. The size of the body surface area with psoriatic lesions was estimated based on the number of palms of the participant, where each palm (from the basis of wrist to the proximal interphalangeal joints including thumb) is equivalent to 1% BSA.

Investigator's Global Assessment (IGA): The IGA documented the investigator's assessment of the participant's psoriasis at a given time-point. Overall lesions were graded for induration, erythema, and scaling using 0 (no evidence), 1 (minimal), 2 (mild), 3 (moderate) and 4 (severe) scale. The IGA score of psoriasis is based upon the average of induration, erythema and scaling scores. The patient's psoriasis was assessed as cleared (0), minimal (1), mild (2), moderate (3), or severe (4).

Psoriasis Area and Severity Index (PASI): A system used for assessing and grading the severity of psoriatic lesions and their response to therapy. In the PASI system, the body is divided into 4 regions: the head, trunk, upper extremities, and lower extremities. Each of these areas was assessed separately for the percentage of the area involved, which translated to a numeric score that ranged from 0 (indicated no involvement) to 6 (90% to 100% involvement), and for erythema, induration, and scaling, which are each rated on a scale of 0 to 4. The PASI produces a numeric score that can range from 0 (no psoriasis) to 72. A PASI 50 response is defined as ≥50% improvement in PASI score from baseline; PASI 75, PASI 90, and PASI 100 are similarly defined.

Dactylitis Assessment: The presence and severity of dactylitis was assessed in both hands and feet using a scoring system from 0 to 3 (0—no dactylitis, 1—mild dactylitis, 2—moderate dactylitis, and 3—severe dactylitis) for each digit. The results were summed to produce a final score ranging from 0 to 60.

Enthesitis Assessment: Enthesitis was assessed using the Leeds Enthesitis Index (LEI) and the Spondyloarthritis Research Consortium of Canada (SPARCC) enthesitis index.

The LEI, a tool specifically validated for PsA patients, counts the number of painful entheses among the following: left and right lateral epicondyle humerus, left and right medial femoral condyle, and left and right achilles tendon insertion. The LEI index ranges from 0 to 6.

The SPARCC enthesitis index was developed from a general spondyloarthritis (ie, not limited to PsA or AS) population and evaluates the number of painful entheses among the following: left and right supraspinatus insertion, left and right medial epicondyle humerus, left and right lateral epicondyle humerus, left and right greater trochanter, left and right quadriceps—to-patella, left and right patellar-to-tibia, left and right achilles tendon insertion, and left and right plantar fascia. The SPARCC enthesitis index ranges from 0 to 16.

Minimal Disease Activity: The PsA MDA criteria are a composite of 7 outcome measures used in PsA. Participants are classified as achieving MDA if they fulfill 5 of 7 outcome measures: tender joint count ≤1; swollen joint count ≤1; psoriasis activity and severity index ≤1; participant pain VAS score of ≤15; participant global disease activity VAS (arthritis and psoriasis) score of ≤20; HAQ-DI score ≤0.5; and tender entheseal points ≤1.

Psoriatic Arthritis Disease Activity Score: The PASDAS (range 0-10) is calculated using the following variables: participant global VAS (arthritis and psoriasis, to 0-100), physician global VAS (range 0-100), swollen joint count (0-66), tender joint count (0-68), CRP level (mg/L), enthesitis (measured by the LEI), dactylitis count (using 2 different counts: [1] scoring each digit from 0-3 and recoding to 0-1, where any score >0 equals 1, and [2] scoring each digit for tenderness 0-1), and, finally, the PCS scale of the SF 36 health survey.

Group for Research and Assessment of Psoriasis and Psoriatic Arthritis Composite Score: GRACE is a composite score of Group for Research and Assessment of Psoriasis and Psoriatic Arthritis (GRAPPA), derived as GRACE Index=(1−AMDF)×10, where AMDF is the Arithmetic Mean of the Desirability Function. The AMDF is calculated by transforming the following variables, using predefined algorithms and expressing the total score as a mean with a score range of 0-1, where 1 indicates a better state than 0: Tender joint count (0-68), swollen joint count (0-66), HAQ-DI score (0-3), participant's global assessment of disease activity (arthritis and psoriasis, 0 100 VAS), participant's assessment of skin disease activity (0-100 VAS), participant's global assessment of disease activity (arthritis, 0-100 VAS) PASI score (0-72) and Psoriatic Arthritis Quality of Life Index (PsAQOL) score.

Disease Activity Index Score 28: DAS28 CRP is a statistically derived index combining tender joints (28 joints), swollen joints (28 joints), CRP, and Participant's Global Assessment of Disease Activity (GH). The set of 28 joint count is based on evaluation of the shoulder, elbow, wrist, metacarpophalangeal (MCP) 1, MCP2, MCP3, MCP4, MCP5, proximal interphalangeal (PIP1), PIP2, PIP3, PIP4, PIP5 joints of both the upper right extremity and the upper left extremity as well as the knee joints of lower right and lower left extremities.

Disease Activity Index for Psoriatic Arthritis: The DAPSA score is calculated as the sum of the following components: tender joint count (0-68), swollen joint count (0-66), CRP level (mg/dL), participant assessment of pain (0-10 VAS), and participant global assessment of disease activity (arthritis, 0-10 VAS).

Modified Psoriatic Arthritis Responder Criteria: A participant is considered a responder if they have improvement in at least 2 of the following criteria, including at least 1 of the joint criteria, with no deterioration in the other criteria: ≥30% decrease in the swollen joint count (66 joints); ≥30% decrease in the tender joint count (68 joints); ≥20% improvement in the participant's overall assessment of disease (arthritis) on a VAS; and ≥20% improvement in the physician's overall assessment of disease on a VAS.

Modified Composite Psoriatic Disease Activity Index: The mCPDAI assesses 4 domains (joints, skin, enthesis, and dactylitis). The mCPDAI scores are calculated using the following assessments: joints (66 swollen and 68 tender joint counts), HAQ-DI, PASI, dactylitis, and enthesitis. Within each domain, a score (range 0-3) is assigned according to predefined cutoffs. The scores for each domain are then added together to give a final score range of 0 (none) to 12 (severe).

Bath Ankylosing Spondylitis Disease Activity Index: A participant self-assessment questionnaire originally developed for ankylosing spondylitis that consists of 6 questions relating to the 5 major symptoms of that disease. Only participants with spondylitis with peripheral arthritis as their primary arthritic presentation of PsA (as assessed by the investigator) have completed the BASDAI using 6 10-unit VAS measures to indicate the degree of their symptoms over the past week on the following criteria: fatigue, spinal pain, joint pain, enthesitis, qualitative morning stiffness, quantitative morning stiffness. Higher scores indicate greater disease severity and a score decrease of 50% or 2 points is considered clinically meaningful.

36-Item Short-form Health Survey (SF-36): The health status and quality of life was assessed using a multi-domain instrument with 36 items that was self-administered by study participants. It included 8 subscales that covered a range of functioning: physical functioning, physical role functioning, bodily pain, general mental health (psychological distress and well-being), emotional role functioning, social functioning, vitality (energy and fatigue), and general health perception. The scoring yields a Physical Component Summary (PCS), a Mental Component Summary (MCS), and subscale scores. Higher scores represented better outcomes, with an increase of 5 points considered to be clinically meaningful.

Functional Assessment of Chronic Illness Therapy (FACIT)-Fatigue: The FACIT-Fatigue questionnaire consists of 13 questions that assess a participant's level of fatigue and tiredness over the last 7 days. Each question is graded on a 5-point scale (0=not at all; 1=a little bit; 2=somewhat; 3=quite a bit; 4=very much). Scores range from 0 to 52, with lower scores reflecting more severe fatigue. In rheumatology, a change of 4 points is considered meaningful and has been used in the PsA population.

Biomarkers

Serum and fecal samples for the analysis of pharmacodynamic biomarkers were collected from all participants. The samples will be used to better understand the biology of PsA, to provide a biological assessment of the response of patients to treatment with guselkumab, to analyze differences between responders and non-responders, and to determine if the markers can be used to classify patients as potential responders prior to treatment.

Samples will moreover be used to analyze inflammation and spondyloarthropathy related proteins. Markers related to the biology of PsA, including (but not limited to) Th17, IL-17A, IL-17F, IL-21, IL-22 and IL-23, metabolomics and bone homeostasis pathways will be measured. Ribonucleic acid from whole blood samples will be used for gene expression analysis to determine the molecular profile of PsA and to assess changes in gene expression post guselkumab treatment.

Summary of Demographics at Baseline

A summary of demographic characteristics at baseline is presented in Table 1. The proportion of male participants was higher in the placebo group (54.2%, n=52) than in the guselkumab group (45.5%, n=86). The mean (SD) weight among participants in the placebo group (91.7 kg [22.58 kg]) was also higher than for the guselkumab group (83.6 kg [17.40 kg]), consistent with the higher proportion of males in this group. The baseline characteristics in the placebo and guselkumab groups were balanced in terms of age (mean [SD]=49.1 [12.14] years and 49.1 [12.31] years, respectively) and BMI (mean [SD]=30.7 [7.12] kg/m² and 29.0 [5.86] kg/m², respectively). The guselkumab group had a higher proportion of elderly participants (aged ≥65 years) than the placebo group (10.6%, n=20 versus 7.3%, n=7). Participants in both study groups were most frequently obese, the proportion of participants with BMI ≥30 kg/m² at baseline being 45.3% (n=43) and 39.2% (n=74) for the placebo and guselkumab groups, respectively.

TABLE 1

Summary of Demographics at Baseline; Full Analysis Set 1

| | Placebo | Guselkumab 100 mg q8w | Total |
|---|---|---|---|
| Analysis set: Full Analysis Set 1 | 96 | 189 | 285 |
| Age (years) | | | |
| N | 96 | 189 | 285 |
| Mean (SD) | 49.1 (12.14) | 49.1 (12.31) | 49.1 (12.23) |
| Median | 50.0 | 50.0 | 50.0 |
| Range | (23; 72) | (23; 79) | (23; 79) |
| IQ range | (40.0; 59.0) | (40.0; 59.0) | (40.0; 59.0) |
| <65 | 89 (92.7%) | 169 (89.4%) | 258 (90.5%) |
| >=65 | 7 (7.3%) | 20 (10.6%) | 27 (9.5%) |
| Sex | | | |
| N | 96 | 189 | 285 |
| Male | 52 (54.2%) | 86 (45.5%) | 138 (48.4%) |
| Female | 44 (45.8%) | 103 (54.5%) | 147 (51.6%) |
| Weight (kg) | | | |
| N | 96 | 189 | 285 |
| Mean (SD) | 91.7 (22.58) | 83.6 (17.40) | 86.3 (19.64) |
| Median | 90.3 | 84.3 | 86.3 |
| Range | (50; 182) | (45; 129) | (45; 182) |
| IQ range | (74.6; 102.2) | (70.0; 96.0) | (73.2; 98.5) |
| Body mass index (kg/m²) | | | |
| N | 95 | 189 | 284 |
| Mean (SD) | 30.7 (7.12) | 29.0 (5.86) | 29.5 (6.35) |
| Median | 29.0 | 28.5 | 28.9 |
| Range | (19; 55) | (16; 48) | (16; 55) |
| IQ range | (25.9; 34.1) | (24.8; 32.3) | (25.0; 32.9) |

TABLE 1-continued

Summary of Demographics at Baseline; Full Analysis Set 1

| | Placebo | Guselkumab 100 mg q8w | Total |
|---|---|---|---|
| Normal (<25) | 18 (18.9%) | 53 (28.0%) | 71 (25.0%) |
| Overweight (≥25 and <30) | 34 (35.8%) | 62 (32.8%) | 96 (33.8%) |
| Obese (≥30) | 43 (45.3%) | 74 (39.2%) | 117 (41.2%) |

Key:
IQ = interquartile

Summary of Psoriatic Arthritis Characteristics at Baseline

The occurrence of different subtypes of psoriatic arthritis was balanced across both groups. Polyarticular arthritis without rheumatoid nodules (41.7%, [n=40] and 39.4%, [n=74]) and asymmetric peripheral arthritis (37.5% [n=36] and 35.1% [n=66]) were the most frequently reported subtypes in the placebo and guselkumab groups, respectively. At baseline, participants in the placebo and guselkumab groups had been diagnosed with PsA for an average (SD) of 8.7 (7.20) years and 8.3 (7.77) years, respectively. Except for 1 participant in the guselkumab group, all participants randomized in the study were naïve to joint procedures.

The PsA disease characteristics for the ACR components at baseline are summarized in Table 2. The mean (SD) number of swollen and tender joints was higher in the guselkumab group (10.2 [6.75] and 21.0 [13.21], respectively) than in the placebo group (9.0 [5.69] and 18.2 [10.68], respectively). On a scale of 0 to 10, the mean (SD) VAS scores for patients' assessment of pain in the placebo and guselkumab groups were 6.03 (1.813) and 6.46 (1.873), respectively. In terms of disease activity rated on a scale of 1 to 10, the mean (SD) VAS scores for the physicians' global assessment were 6.42 (1.743) and 6.87 (1.511) in the placebo and guselkumab groups, respectively. The mean (SD) VAS scores for the patients' global assessment were 6.22 (1.739) and 6.52 (1.749) in the placebo and guselkumab groups, respectively. The mean (SD) HAQ-DI scores in the placebo and guselkumab groups were 1.2227 (0.59747) and 1.3305 (0.60157), respectively. The mean (SD) CRP levels for the placebo and guselkumab groups were 1.154 mg/dL (2.5358 mg/dL) and 1.225 mg/dL (1.9583 mg/dL), respectively.

TABLE 2

Summary of Psoriatic Arthritis Disease Characteristics for ACR Components at Baseline; Full Analysis Set 1

| | Placebo | Guselkumab 100 mg q8w | Total |
|---|---|---|---|
| Analysis set: Full Analysis Set 1 | 96 | 189 | 285 |
| Number of swollen joints (0-66) | | | |
| N | 96 | 189 | 285 |
| Mean (SD) | 9.0 (5.69) | 10.2 (6.75) | 9.8 (6.43) |
| Median | 8.0 | 8.0 | 8.0 |
| Range | (3; 38) | (3; 39) | (3; 39) |
| IQ range | (5.0; 11.0) | (6.0; 13.0) | (6.0; 12.0) |
| Number of tender joints (0-68) | | | |
| N | 96 | 189 | 285 |
| Mean (SD) | 18.2 (10.68) | 21.0 (13.21) | 20.1 (12.47) |
| Median | 16.0 | 18.0 | 17.0 |
| Range | (4; 58) | (3; 68) | (3; 68) |
| IQ range | (11.0; 23.5) | (12.0; 26.0) | (11.0; 25.0) |

TABLE 2-continued

Summary of Psoriatic Arthritis Disease Characteristics
for ACR Components at Baseline; Full Analysis Set 1

| | Placebo | Guselkumab 100 mg q8w | Total |
|---|---|---|---|
| Patient's assessment of pain (VAS; 0-10 cm) | | | |
| N | 96 | 189 | 285 |
| Mean (SD) | 6.03 (1.813) | 6.46 (1.873) | 6.32 (1.861) |
| Median | 6.10 | 6.60 | 6.50 |
| Range | (0.7; 9.1) | (1.0; 10.0) | (0.7; 10.0) |
| IQ range | (4.80; 7.35) | (5.30; 7.90) | (5.00; 7.70) |
| Patient's global assessment of disease activity (arthritis, VAS; 0-10 cm) | | | |
| N | 96 | 189 | 285 |
| Mean (SD) | 6.22 (1.739) | 6.52 (1.749) | 6.42 (1.748) |
| Median | 6.30 | 6.70 | 6.60 |
| Range | (1.0; 9.1) | (2.3; 10.0) | (1.0; 10.0) |
| IQ range | (5.10; 7.60) | (5.20; 7.70) | (5.20; 7.70) |
| Physician's global assessment of disease activity (VAS; 0-10 cm) | | | |
| N | 96 | 189 | 285 |
| Mean (SD) | 6.42 (1.743) | 6.87 (1.511) | 6.72 (1.604) |
| Median | 6.55 | 7.00 | 6.90 |
| Range | (0.6; 9.2) | (3.1; 9.8) | (0.6; 9.8) |
| IQ range | (5.20; 7.85) | (6.00; 8.00) | (5.70; 8.00) |
| HAQ disability index (0-3) | | | |
| N | 96 | 188 | 284 |
| Mean (SD) | 1.2227 (0.59747) | 1.3305 (0.60157) | 1.2940 (0.60131) |
| Median | 1.2500 | 1.3750 | 1.2500 |
| Range | (0.000; 3.000) | (0.000; 2.750) | (0.000; 3.000) |
| IQ range | (0.8750; 1.6875) | (0.8750; 1.8125) | (0.8750; 1.7500) |
| CRP (mg/dL) | | | |
| N | 96 | 188 | 284 |
| Mean (SD) | 1.154 (2.5358) | 1.225 (1.9583) | 1.201 (2.1665) |
| Median | 0.366 | 0.498 | 0.415 |
| Range | (0.03; 15.70) | (0.01; 11.40) | (0.01; 15.70) |
| IQ range | (0.146; 1.004) | (0.162; 1.235) | (0.149; 1.155) |

Key:
ACR = IQ = interquartile,
IQ = interquartile

A summary of PsA disease characteristics at baseline for signs and symptoms other than ACR components is presented in Table 3. The mean (SD) DAS28 CRP levels observed in the placebo and guselkumab groups were 4.57 (0.770) and 4.90 (1.002), respectively. Using the 28 rather than the 66/68 joint count, the mean (SD) number of swollen and tender joints were higher in the guselkumab group (5.9 [4.05] and 10.6 [6.46], respectively) than in the placebo group (4.7 [3.16] and 8.6 [5.34], respectively). Based on the LEI, 66.7% (n=64) of participants in the placebo group and 67.4% (n=126) in the guselkumab group suffered from enthesitis, scoring an average (SD) of 2.7 (1.45) and 2.9 (1.53), respectively, on the LEI enthesitis scale (ranging from 1 to 6). Based on the SPARCC enthesitis index, 76.0% (n=73) of participants in the placebo group and 70.6% (n=132) of participants in the guselkumab group suffered from enthesitis, scoring an average (SD) of 5.1 (3.31) and 5.5 (3.80), respectively on the SPARCC enthesitis index (ranging from 1 to 16). Dactylitis was reported by 37.5% (n=36) and 35.8% (n=67) of participants in the placebo and guselkumab groups, respectively. On a scale of 1 to 60, participants in the placebo and guselkumab groups scored an average (SD) of 7.4 (8.31) and 6.7 (6.47), respectively.

TABLE 3

Summary of Psoriatic Arthritis Disease Characteristics for Sign and Symptom
Measurements Other Than ACR Components at Baseline; Full Analysis Set 1

| | Placebo | Guselkumab 100 mg q8w | Total |
|---|---|---|---|
| Analysis set: Full Analysis Set 1 | 96 | 189 | 285 |
| DAS28 (CRP) | | | |
| N | 96 | 188 | 284 |
| Mean (SD) | 4.57 (0.770) | 4.90 (1.002) | 4.79 (0.942) |

US 12,655,206 B2

TABLE 3-continued

Summary of Psoriatic Arthritis Disease Characteristics for Sign and Symptom
Measurements Other Than ACR Components at Baseline; Full Analysis Set 1

| | Placebo | Guselkumab 100 mg q8w | Total |
|---|---|---|---|
| Median | 4.65 | 4.81 | 4.70 |
| Range | (2.1; 6.6) | (2.0; 7.4) | (2.0; 7.4) |
| IQ range | (4.10; 5.07) | (4.30; 5.53) | (4.22; 5.37) |
| Number of swollen joints (0-28) | | | |
| N | 96 | 189 | 285 |
| Mean (SD) | 4.7 (3.16) | 5.9 (4.05) | 5.5 (3.81) |
| Median | 4.0 | 5.0 | 5.0 |
| Range | (0; 17) | (0; 20) | (0; 20) |
| IQ range | (2.5; 6.0) | (3.0; 8.0) | (3.0; 7.0) |
| Number of tender joints (0-28) | | | |
| N | 96 | 189 | 285 |
| Mean (SD) | 8.6 (5.34) | 10.6 (6.46) | 9.9 (6.17) |
| Median | 7.0 | 9.0 | 9.0 |
| Range | (1; 27) | (0; 28) | (0; 28) |
| IQ range | (4.0; 12.0) | (6.0; 14.0) | (5.0; 13.0) |
| Enthesitis (based on LEI) | | | |
| N | 96 | 187 | 283 |
| Participants with enthesitis at baseline | 64 (66.7%) | 126 (67.4%) | 190 (67.1%) |
| Enthesitis score (based on LEI) (1-6) | | | |
| N | 64 | 126 | 190 |
| Mean (SD) | 2.7 (1.45) | 2.9 (1.53) | 2.8 (1.50) |
| Median | 2.0 | 3.0 | 2.0 |
| Range | (1; 6) | (1; 6) | (1; 6) |
| IQ range | (1.5; 4.0) | (2.0; 4.0) | (2.0; 4.0) |
| Enthesitis (based on SPARCC enthesitis index) | | | |
| N | 96 | 187 | 283 |
| Participants with enthesitis (SPARCC enthesitis index >0) | 73 (76.0%) | 132 (70.6%) | 205 (72.4%) |
| Enthesitis score (based on SPARCC enthesitis index) (1-16) | | | |
| N | 73 | 132 | 205 |
| Mean (SD) | 5.1 (3.31) | 5.5 (3.80) | 5.4 (3.63) |
| Median | 4.0 | 4.5 | 4.0 |
| Range | (1; 16) | (1; 16) | (1; 16) |
| IQ range | (3.0; 7.0) | (2.0; 8.0) | (3.0; 8.0) |
| Dactylitis | | | |
| N | 96 | 187 | 283 |
| Participants with dactylitis | 36 (37.5%) | 67 (35.8%) | 103 (36.4%) |
| Dactylitis score (1-60) | | | |
| N | 36 | 67 | 103 |
| Mean (SD) | 7.4 (8.31) | 6.7 (6.47) | 6.9 (7.13) |
| Median | 4.0 | 4.0 | 4.0 |
| Range | (1; 42) | (1; 32) | (1; 42) |
| IQ range | (2.0; 10.0) | (3.0; 8.0) | (2.0; 8.0) |

Key:
PsA = psoriatic arthritis,
IQ = interquartile,
LEI = Leeds Enthesitis Index,
DAS28 = Disease Activity Index Score 28 using CRP,
CRP = C-Reactive Protein,
SPARCC = Spondyloarthritis Research Consortium of Canada,
PASDAS = Psoriatic Arthritis Disease A Summary of Psoriasis Characteristics at Baseline A summary of psoriasis disease characteristics at baseline is presented in Table 4. A total of 61 (63.5%) participants in the placebo group and 120 (63.4%) participants in the guselkumab group reported psoriatic skin disease at baseline. Among these participants, scalp psoriasis (78.7% [n=48] and 82.5% [n=99], in the placebo and guselkumab groups, respectively) and nail psoriasis (78.7% [n=48] and 79.2% [n=95], in the placebo and guselkumab groups, respectively) were the most commonly reported psoriatic types at baseline. Hand and/or foot involvement was reported by 21.3% (n=13) and 23.3% (n=28) of participants in the placebo and guselkumab groups, respectively. At baseline, the extent of psoriasis (in terms of BSA) was most frequently <3% (34.4%, n=33) and ≥3% and <10% (27.1%, n=26) in the placebo group, and ≥20% (31.7%, n=60) and ≥3% and <10% (29.1%, n=55) in the guselkumab group. The PASI scores were most frequently <12 in both the placebo (67.7%, n=65) and guselkumab (63.3%, n=119) groups; mean (SD) PASI scores were 9.2 (9.41) in the placebo group and 11.7 (11.87) in the guselkumab group. The proportion of participants with IGA score ≥2 was 69.8% (n=67) and 78.8% (n=149) in the placebo and guselkumab groups, respectively. Patient global assessment of arthritis and psoriasis based on mean (SD) VAS scores in the placebo and guselkumab groups were 6.4 (1.75) and 6.8 (1.80), respectively. The mean (SD) VAS scores from the patient assessment of skin disease activity in the placebo and guselkumab groups were 5.6 (2.40) and 6.3 (2.35), respectively. Mean (SD) baseline DLQI scores in the placebo and guselkumab groups were 12.4 (7.34) and 13.5 (6.80), respectively, with a very large and extremely large effect of psoriasis on quality of life reported among participants in both groups (58.3% [n=56] and 63.6% [n=119], respectively.

TABLE 4

| Summary of Psoriasis Disease Characteristics at Baseline; Full Analysis Set 1 | | | |
|---|---|---|---|
| | Placebo | Guselkumab 100 mg q8w | Total |
| Analysis set: Full Analysis Set 1 | 96 | 189 | 285 |
| Psoriasis condition | | | |
| N | 61 | 120 | 181 |
| Scalp psoriasis | 48 (78.7%) | 99 (82.5%) | 147 (81.2%) |
| Nail psoriasis | 48 (78.7%) | 95 (79.2%) | 143 (79.0%) |
| Hand and/or foot psoriasis | 13 (21.3%) | 28 (23.3%) | 41 (22.7%) |
| Psoriatic BSA (%) | | | |
| N | 96 | 189 | 285 |
| Mean (SD) | 13.4 (17.72) | 17.9 (21.47) | 16.4 (20.37) |
| Median | 6.0 | 9.0 | 8.0 |
| Range | (0; 88) | (0; 90) | (0; 90) |
| IQ range | (1.5; 18.5) | (3.0; 25.0) | (2.0; 22.0) |
| <3% | 33 (34.4%) | 42 (22.2%) | 75 (26.3%) |
| ≥3% and <10% | 26 (27.1%) | 55 (29.1%) | 81 (28.4%) |
| ≥10% and <20% | 14 (14.6%) | 32 (16.9%) | 46 (16.1%) |
| ≥20% | 23 (24.0%) | 60 (31.7%) | 83 (29.1%) |
| PASI score (0-72) | | | |
| N | 96 | 188 | 284 |
| Mean (SD) | 9.2 (9.41) | 11.7 (11.87) | 10.9 (11.15) |
| Median | 6.3 | 8.2 | 8.0 |
| Range | (0; 35) | (0; 57) | (0; 57) |
| IQ range | (1.4; 15.2) | (3.1; 15.5) | (2.4; 15.4) |
| <12 | 65 (67.7%) | 119 (63.3%) | 184 (64.8%) |
| ≥12 and <20 | 19 (19.8%) | 33 (17.6%) | 52 (18.3%) |
| ≥20 | 12 (12.5%) | 36 (19.1%) | 48 (16.9%) |
| IGA score | | | |
| N | 96 | 189 | 285 |
| Cleared (0) | 7 (7.3%) | 12 (6.3%) | 19 (6.7%) |
| Minimal (1) | 22 (22.9%) | 28 (14.8%) | 50 (17.5%) |
| Mild (2) | 30 (31.3%) | 70 (37.0%) | 100 (35.1%) |
| Moderate (3) | 34 (35.4%) | 67 (35.4%) | 101 (35.4%) |
| Severe (4) | 3 (3.1%) | 12 (6.3%) | 15 (5.3%) |
| <2 | 29 (30.2%) | 40 (21.2%) | 69 (24.2%) |
| ≥2 | 67 (69.8%) | 149 (78.8%) | 216 (75.8%) |
| Patient's global assessment of disease activity (arthritis and psoriasis, VAS; 0-10 cm) | | | |
| N | 96 | 188 | 284 |
| Mean (SD) | 6.4 (1.75) | 6.8 (1.80) | 6.7 (1.79) |
| Median | 6.5 | 7.1 | 6.8 |
| Range | (2; 10) | (2; 10) | (2; 10) |
| IQ range | (5.2; 7.8) | (5.7; 8.0) | (5.6; 8.0) |
| Patient's assessment of skin disease activity (skin, VAS; 0-10 cm) | | | |
| N | 96 | 188 | 284 |
| Mean (SD) | 5.6 (2.40) | 6.3 (2.35) | 6.1 (2.39) |
| Median | 6.1 | 6.7 | 6.4 |
| Range | (0; 9) | (0; 10) | (0; 10) |
| IQ range | (3.8; 7.5) | (5.0; 8.2) | (4.7; 8.1) |
| DLQI score (0-30) | | | |
| N | 96 | 187 | 283 |
| Mean (SD) | 12.4 (7.34) | 13.5 (6.80) | 13.1 (7.00) |
| Median | 12.0 | 13.0 | 13.0 |
| Range | (0; 30) | (0; 29) | (0; 30) |

TABLE 4-continued

| | Placebo | Guselkumab 100 mg q8w | Total |
|---|---|---|---|
| Summary of Psoriasis Disease Characteristics at Baseline; Full Analysis Set 1 | | | |
| IQ range | (6.5; 16.0) | (9.0; 18.0) | (8.0; 18.0) |
| 0-1 (No effect) | 5 (5.2%) | 8 (4.3%) | 13 (4.6%) |
| 2-5 (Small effect) | 13 (13.5%) | 15 (8.0%) | 28 (9.9%) |
| 6-10 (Moderate effect) | 22 (22.9%) | 45 (24.1%) | 67 (23.7%) |
| 11-20 (Very large effect) | 42 (43.8%) | 87 (46.5%) | 129 (45.6%) |
| 21-30 (Extremely large effect) | 14 (14.6%) | 32 (17.1%) | 46 (16.3%) |

Key:
IQ = interquartile,
DLQI = Dermatology Life Quality Index,
PASI = Psoriasis Area and Severity Index,
VAS = visual analog scale Prior and Concomitant Medications/Therapies A summary of prior medications received by participants (recorded at baseline) is presented in Table 5. The types of prior therapies and medications received by participants in both study groups (recorded at baseline) was similar. Adalimumab (33.3% [n=32] and 30.2% [n=57]) and diclofenac (29.2% [n=28] and 22.2% [n=42]) were the most frequently used PsA-related medications in the placebo and guselkumab groups, respectively. Folic acid was the most frequently received prior medication that was not related to PsA or psoriasis (41.7% [n=40] and 32.3% [n=61] in the placebo and guselkumab groups, respectively).

TABLE 5

| Summary of Prior Medications and Therapies Received by ≥2% of Participants; Full Analysis Set 1 | | | |
|---|---|---|---|
| | Placebo | Guselkumab 100 mg q8w | Total |
| Analysis set: Full Analysis Set 1 | 96 | 189 | 285 |
| Psoriatic arthritis-related medications, other than methotrexate | | | |
| Aceclofenac | 6 (6.3%) | 12 (6.3%) | 18 (6.3%) |
| Adalimumab | 32 (33.3%) | 57 (30.2%) | 89 (31.2%) |
| Arcoxia | 4 (4.2%) | 10 (5.3%) | 14 (4.9%) |
| Betamethasone | 15 (15.6%) | 12 (6.3%) | 27 (9.5%) |
| Celecoxib | 3 (3.1%) | 7 (3.7%) | 10 (3.5%) |
| Certolizumab Pegol | 1 (1.0%) | 7 (3.7%) | 8 (2.8%) |
| Dexamethasone | 6 (6.3%) | 5 (2.6%) | 11 (3.9%) |
| Diclofenac | 28 (29.2%) | 42 (22.2%) | 70 (24.6%) |
| Etanercept | 16 (16.7%) | 36 (19.0%) | 52 (18.2%) |
| Etoricoxib | 10 (10.4%) | 9 (4.8%) | 19 (6.7%) |
| Folic Acid | 6 (6.3%) | 28 (14.8%) | 34 (11.9%) |
| Golimumab | 15 (15.6%) | 22 (11.6%) | 37 (13.0%) |
| Hydrocortisone | 2 (2.1%) | 0 | 2 (0.7%) |
| Hydroxychloroquine | 1 (1.0%) | 5 (2.6%) | 6 (2.1%) |
| Ibuprofen | 6 (6.3%) | 13 (6.9%) | 19 (6.7%) |
| Indomethacin [indometacin] | 4 (4.2%) | 2 (1.1%) | 6 (2.1%) |
| Infliximab | 7 (7.3%) | 17 (9.0%) | 24 (8.4%) |
| Leflunomide | 21 (21.9%) | 38 (20.1%) | 59 (20.7%) |
| Meloxicam | 25 (26.0%) | 35 (18.5%) | 60 (21.1%) |
| Methylprednisolone | 23 (24.0%) | 34 (18.0%) | 57 (20.0%) |
| Naproxen | 8 (8.3%) | 13 (6.9%) | 21 (7.4%) |
| Nimesulide | 9 (9.4%) | 23 (12.2%) | 32 (11.2%) |
| Other Drugs For Disorders Of The Musculo-Skeletal System | 1 (1.0%) | 0 | 1 (0.4%) |
| Paracetamol | 2 (2.1%) | 4 (2.1%) | 6 (2.1%) |
| Prednisolone | 12 (12.5%) | 20 (10.6%) | 32 (11.2%) |
| Prednisone | 4 (4.2%) | 7 (3.7%) | 11 (3.9%) |
| Reumoxicam | 2 (2.1%) | 2 (1.1%) | 4 (1.4%) |
| Skudexa | 2 (2.1%) | 0 | 2 (0.7%) |
| Sulfasalazine | 18 (18.8%) | 25 (13.2%) | 43 (15.1%) |
| Tramadol | 3 (3.1%) | 1 (0.5%) | 4 (1.4%) |
| Triamcinolone | 2 (2.1%) | 1 (0.5%) | 3 (1.1%) |
| Triamcinolone Hexacetonide | 0 | 1 (0.5%) | 1 (0.4%) |
| Psoriasis-related medications, other than methotrexate | | | |
| All Other Therapeutic Products | 5 (5.2%) | 5 (2.6%) | 10 (3.5%) |
| Betamethasone | 4 (4.2%) | 1 (0.5%) | 5 (1.8%) |
| Clobetasol | 2 (2.1%) | 0 | 2 (0.7%) |

TABLE 5-continued

Summary of Prior Medications and Therapies Received
by ≥2% of Participants; Full Analysis Set 1

| | Placebo | Guselkumab 100 mg q8w | Total |
|---|---|---|---|
| Daivobet [betamethasone Dipropionate; calcipotriol] | 2 (2.1%) | 3 (1.6%) | 5 (1.8%) |
| Momegalen | 2 (2.1%) | 0 | 2 (0.7%) |
| Salicylic Acid | 2 (2.1%) | 3 (1.6%) | 5 (1.8%) |
| Psoriatic arthritis and psoriasis-related medications, other than methotrexate | | | |
| Adalimumab | 16 (16.7%) | 33 (17.5%) | 49 (17.2%) |
| Certolizumab Pegol | 4 (4.2%) | 1 (0.5%) | 5 (1.8%) |
| Cyclosporine | 2 (2.1%) | 3 (1.6%) | 5 (1.8%) |
| Etanercept | 4 (4.2%) | 15 (7.9%) | 19 (6.7%) |
| Golimumab | 5 (5.2%) | 11 (5.8%) | 16 (5.6%) |
| Infliximab | 6 (6.3%) | 11 (5.8%) | 17 (6.0%) |
| Methylprednisolone | 2 (2.1%) | 3 (1.6%) | 5 (1.8%) |
| Nimesulide | 3 (3.1%) | 4 (2.1%) | 7 (2.5%) |
| Not Psoriatic Arthritis or Psoriasis-related | | | |
| Acetylsalicylic Acid | 2 (2.1%) | 4 (2.1%) | 6 (2.1%) |
| Acidum Folicum | 1 (1.0%) | 4 (2.1%) | 5 (1.8%) |
| Atorvastatin | 1 (1.0%) | 5 (2.6%) | 6 (2.1%) |
| Bisoprolol | 4 (4.2%) | 12 (6.3%) | 16 (5.6%) |
| Candesartan | 2 (2.1%) | 3 (1.6%) | 5 (1.8%) |
| Citalopram | 2 (2.1%) | 0 | 2 (0.7%) |
| Dekristol | 2 (2.1%) | 3 (1.6%) | 5 (1.8%) |
| Enalapril | 2 (2.1%) | 2 (1.1%) | 4 (1.4%) |
| Folic Acid | 40 (41.7%) | 61 (32.3%) | 101 (35.4%) |
| Indapamid | 3 (3.1%) | 2 (1.1%) | 5 (1.8%) |
| Isoniazid | 10 (10.4%) | 10 (5.3%) | 20 (7.0%) |
| Lisinopril | 1 (1.0%) | 4 (2.1%) | 5 (1.8%) |
| Losartan | 2 (2.1%) | 7 (3.7%) | 9 (3.2%) |
| Metformin | 4 (4.2%) | 14 (7.4%) | 18 (6.3%) |
| Omeprazol [omeprazole] | 2 (2.1%) | 8 (4.2%) | 10 (3.5%) |
| Omeprazole | 10 (10.4%) | 19 (10.1%) | 29 (10.2%) |
| Pantoprazol [pantoprazole] | 3 (3.1%) | 1 (0.5%) | 4 (1.4%) |
| Pantoprazole | 2 (2.1%) | 7 (3.7%) | 9 (3.2%) |
| Paracetamol | 2 (2.1%) | 2 (1.1%) | 4 (1.4%) |
| Perindopril | 4 (4.2%) | 5 (2.6%) | 9 (3.2%) |
| Polocard | 2 (2.1%) | 1 (0.5%) | 3 (1.1%) |
| Rosuvastatin | 0 | 6 (3.2%) | 6 (2.1%) |

Key:
PsA = psoriatic arthritis

A summary of prior non-biologic, DMARD, immunosuppresive, steroid, NSAID or apremilast treatments received by participants at baseline is presented in Table 6.

The majority of participants in the placebo and guselkumab groups had previously received non-biologic DMARDs, immunosuppressives, or apremilast (94.8% [n=91] and 93.7% [n=177], respectively). All the participants in both groups also reported the use of prior anti-TNFα medication, with the majority receiving 1 prior anti-TNF medication (88.5% [n=85] and 88.4 [n=167] in the placebo and guselkumab groups, respectively). Methotrexate was the most frequently received DMARD, received by 91.7% (n=88) and 90.5% (n=171) of the participants in the placebo and guselkumab groups, respectively. Only a small proportion of participants (<6%) in both groups reported prior immunosuppressive or apremilast therapy.

TABLE 6

Summary of Prior Treatments of Non-biologic DMARDs, Immunosuppressives,
Systemic Corticosteroids, NSAIDs, or Apremilast; Full Analysis Set

| | Placebo | Guselkumab 100 mg q8w | Total |
|---|---|---|---|
| Analysis set: Full Analysis Set 1 | 96 | 189 | 285 |
| Participants with any prior medication/therapy for PsA | 96 (100.0%) | 189 (100.0%) | 285 (100.0%) |
| Participants with any prior treatments of non-biologic DMARDs, immunosuppressives, or apremilast | 91 (94.8%) | 177 (93.7%) | 268 (94.0%) |
| 1 treatment | 53 (55.2%) | 112 (59.3%) | 165 (57.9%) |
| 2 treatments | 26 (27.1%) | 46 (24.3%) | 72 (25.3%) |
| ≥3 treatments | 12 (12.5%) | 19 (10.1%) | 31 (10.9%) |

TABLE 6-continued

Summary of Prior Treatments of Non-biologic DMARDs, Immunosuppressives,
Systemic Corticosteroids, NSAIDs, or Apremilast; Full Analysis Set

| | Placebo | Guselkumab 100 mg q8w | Total |
|---|---|---|---|
| Participants who took DMARDs | 91 (94.8%) | 177 (93.7%) | 268 (94.0%) |
| 1 DMARDs | 55 (57.3%) | 117 (61.9%) | 172 (60.4%) |
| 2 DMARDs | 27 (28.1%) | 43 (22.8%) | 70 (24.6%) |
| ≥3 DMARDs | 9 (9.4%) | 17 (9.0%) | 26 (9.1%) |
| Hydroxychloroquine | 1 (1.0%) | 6 (3.2%) | 7 (2.5%) |
| Leflunomide | 21 (21.9%) | 40 (21.2%) | 61 (21.4%) |
| Methotrexate | 88 (91.7%) | 171 (90.5%) | 259 (90.9%) |
| Sulfasalazine | 18 (18.8%) | 29 (15.3%) | 47 (16.5%) |
| Other DMARDs | 7 (7.3%) | 11 (5.8%) | 18 (6.3%) |
| Participants who took anti-TNFs | 96 (100.0%) | 189 (100.0%) | 285 (100.0%) |
| 1 Anti-TNF | 85 (88.5%) | 167 (88.4%) | 252 (88.4%) |
| 2 Anti-TNF | 11 (11.5%) | 22 (11.6%) | 33 (11.6%) |
| Participants who took any immunosuppressives | 5 (5.2%) | 7 (3.7%) | 12 (4.2%) |
| Azathioprine | 0 | 0 | 0 |
| Cyclosporine | 5 (5.2%) | 7 (3.7%) | 12 (4.2%) |
| Participants who took Apremilast | 2 (2.1%) | 4 (2.1%) | 6 (2.1%) |

Key:
DMARDs = disease-modifying antirheumatic drugs,
NSAIDs = nonsteroidal anti-inflammatory drugs,
PsA = psoriatic arthritis,
TNF = tumor necrosis factor A summary of frequently received post-baseline concomitant medication received by participants up to Week 24 is presented in Table 7. The use of concomitant medications up to Week 24 of the study was balanced in the placebo group (77.1% [n=74]) and guselkumab group (70.4% [n=133]). Immunosuppressants such as methotrexate were most frequently received by participants in both groups (53.1% [n=51] and 55.6% [n=105] in the placebo and guselkumab groups, respectively). Concomitant use of paracetamol (3.1% [n=3] and 5.8% [n=11]) and glucocorticoids (4.2% [n=4] and 5.3% [n=10]) was limited, yet constituted the other most commonly received concomitant medications in the placebo and guselkumab groups, respectively (Table 7).

TABLE 7

Summary of Concomitant Medications and Therapies
Post-baseline through Week 24 by ATC Class
and Medication; Full Analysis Set 1

| | Placebo | Guselkumab 100 mg q8w | Total |
|---|---|---|---|
| Analysis set: Full Analysis Set 1 | 96 | 189 | 285 |
| Participants with 1 or more concomitant medications | 74 (77.1%) | 133 (70.4%) | 207 (72.6%) |
| ATC class | | | |
| Standard medication name | | | |
| Other Immunosuppressants | 51 (53.1%) | 105 (55.6%) | 156 (54.7%) |
| Methotrexate | 51 (53.1%) | 105 (55.6%) | 156 (54.7%) |
| Anilides | 3 (3.1%) | 12 (6.3%) | 15 (5.3%) |
| Paracetamol | 3 (3.1%) | 11 (5.8%) | 14 (4.9%) |
| Glucocorticoids | 4 (4.2%) | 10 (5.3%) | 14 (4.9%) |
| Influenza Vaccines | 3 (3.1%) | 5 (2.6%) | 8 (2.8%) |

All participants randomized in the study had been previously treated with MTX, with most frequently reporting ≥3 years of exposure (51.1% [n=45] in the placebo group and 45.0% [n=77] in the guselkumab group). The maximum dose of MTX received in the last 3 months was similar for participants in both groups (mean [SD]=10.7 [8.12] and 10.5 [8.09] in the placebo and guselkumab groups, respectively). More than half of participants in both groups opted to continue MTX usage during the study (58.0% [n=51] and 61.4% [n=105] in the placebo and guselkumab groups, respectively.

Up to Week 24, joint procedures were reported for 2 (2.1%) participants in the placebo group and 1 (0.5%) participant in the guselkumab group. One (1.0%) participant in the placebo group and 4 (2.1%) participants in the guselkumab group received joint injections up to Week 24 of the study.

A summary of protocol deviations through Week 24 is presented in Table 8. Major protocol deviations through Week 24 of the study were reported for 34 (35.4%) participants in the placebo group and 45 (23.8%) participants in the guselkumab group. The main reason for protocol deviations was "received wrong treatment or incorrect dose" (16.7% [n=16] and 11.1% [n=21] in the placebo and guselkumab group, respectively); however, the majority of these were related to study interventions administered outside the visit window. A total of 8 (8.3%) participants in the placebo group and 12 (6.3%) participants in the guselkumab group were incorrectly routed to Early Escape, despite not fulfilling the Early Escape criteria. "Other" reasons for major protocol deviations were recorded for 14 (14.6%) and 27 (14.3%) participants in the placebo and guselkumab groups, respectively.

TABLE 8

| | Placebo | Guselkumab 100 mg q8w | Total |
|---|---|---|---|
| Number of Participants with Major Protocol Deviations through Week 24; Full Analysis Set 1 | | | |
| Analysis set: Full Analysis Set 1 | 96 | 189 | 285 |
| Participants with major protocol deviations | 34 (35.4%) | 45 (23.8%) | 79 (27.7%) |
| Entered but did not satisfy criteria | 5 (5.2%) | 1 (0.5%) | 6 (2.1%) |
| Received wrong treatment or incorrect dose | 16 (16.7%) | 21 (11.1%) | 37 (13.0%) |
| Received a disallowed concomitant treatment | 5 (5.2%) | 7 (3.7%) | 12 (4.2%) |
| Developed withdrawal criteria but not withdrawn | 0 | 0 | 0 |
| Other | 14 (14.6%) | 27 (14.3%) | 41 (14.4%) |

Treatment compliance rates were high for both study groups, with mean (SD) rates of 99.8% (2.04%) in the placebo group and 99.6% (4.06%) in the guselkumab group through Week 24. In the placebo group, the mean (SD) compliance rate for placebo injections was 99.7% (3.40%). A total of 45 participants in the placebo group were assigned Early Escape and received guselkumab injections prior to Week 24. Among these participants, the compliance rate for guselkumab injections was 100.0%. In the guselkumab group, the mean (SD) compliance rates for guselkumab injections was 99.6% (4.06%). A total of 39 participants in the guselkumab group were assigned Early Escape and received placebo injections at Week 16, with a compliance rate of 100.0%.

A summary of participants meeting the treatment failure criteria through Week 24 is presented in Table 9. At Week 24, 54.2% (n=52) and 27.0% (n=51) of participants in the placebo and guselkumab groups, respectively, met 1 or more treatment failure criteria. The largest proportion of participants in both study groups were categorized as treatment failures due to Early Escape at Week 16 (46.9% [n=45] and 20.6% [n=39] in the placebo and guselkumab groups, respectively). This also included the 20 participants (8 and 12 in the placebo and guselkumab group, respectively) who were incorrectly routed to Early Escape at Week 16, while not fulfilling the Early Escape criterion.

TABLE 9

| | Placebo | Guselkumab 100 mg q8w | Total |
|---|---|---|---|
| Number of Participants Who Met Treatment Failure Criteria through Week 24; Full Analysis Set 1 | | | |
| Analysis set: Full Analysis Set 1 | 96 | 189 | 285 |
| Participants who met 1 or more treatment failure criteria | 52 (54.2%) | 51 (27.0%) | 103 (36.1%) |
| Participants who discontinued study agent injections due to any reason(s) | 10 (10.4%) | 15 (7.9%) | 25 (8.8%) |
| Participants who discontinued study participation due to any reason(s) | 2 (2.1%) | 3 (1.6%) | 5 (1.8%) |
| Participants who initiated or increased the dose of non-biologic DMARD (MTX, SSZ, HCQ, LEF) or oral corticosteroids over baseline for PsA | 7 (7.3%) | 3 (1.6%) | 10 (3.5%) |
| MTX | 1 (1.0%) | 0 | 1 (0.4%) |
| SSZ, HCQ, or LEF | 1 (1.0%) | 1 (0.5%) | 2 (0.7%) |
| Oral corticosteroids | 3 (3.1%) | 2 (1.1%) | 5 (1.8%) |
| NSAIDs | 2 (2.1%) | 0 | 2 (0.7%) |
| Participants who initiated protocol prohibited medications/therapies for PsA | 4 (4.2%) | 3 (1.6%) | 7 (2.5%) |
| Participants who Early Escape | 45 (46.9%) | 39 (20.6%) | 84 (29.5%) |

Key:

DMARD = Disease-modifying antirheumatic drug

A summary of treatment exposure prior to Week 24 is presented in Table 10. Prior to the Week 24 visit, the majority (>92%) of participants in both groups had received ≥4 administrations of study intervention. Among these were the 84 participants who met the Early Escape criteria at Week 16; early escape participants in the placebo group (45 of 96 participants) had received guselkumab doses at Week 16 and Week 20, and those in the guselkumab group (39 of 189 participants) had received placebo at Week 16. Participants in the placebo (Early Escape) and guselkumab groups who received guselkumab up to Week 24 received an average (SD) of 2.0 (0.15) and 3.9 (0.44) SC doses of guselkumab, respectively. The total average (SD) dosage of guselkumab was 197.8 mg (14.91 mg) in the placebo Early Escape group and 389.4 mg (43.69 mg) in the guselkumab group. The mean (SD) duration of follow-up was similar for both groups (23.8 weeks [2.14 weeks] and 23.9 weeks [1.50 weeks] for the placebo and guselkumab groups, respectively).

TABLE 10

Summary of Treatment Exposure and Study Follow-up Prior to Week 24 Administration; Safety Analysis Set

| | Placebo | Guselkumab 100 mg q8w |
|---|---|---|
| Analysis set: Safety Analysis Set | 96 | 189 |
| Number of administrations | | |
| N | 96 | 189 |
| Mean (SD) | 4.3 (0.86) | 4.1 (0.63) |
| Median | 4.0 | 4.0 |
| Range | (1; 5) | (1; 5) |
| IQ range | (4.0; 5.0) | (4.0; 4.0) |
| ≥1 | 96 (100.0%) | 189 (100.0%) |
| ≥2 | 93 (96.9%) | 188 (99.5%) |
| ≥3 | 91 (94.8%) | 183 (96.8%) |
| ≥4 | 90 (93.8%) | 175 (92.6%) |
| ≥5 | 44 (45.8%) | 40 (21.2%) |
| =6 | 0 | 0 |
| Number of guselkumab administrations | | |
| N | 45 | 189 |
| Mean (SD) | 2.0 (0.15) | 3.9 (0.44) |
| Median | 2.0 | 4.0 |
| Range | (1; 2) | (1; 5) |
| IQ range | (2.0; 2.0) | (4.0; 4.0) |
| ≥1 | 45 (100.0%) | 189 (100.0%) |
| ≥2 | 44 (97.8%) | 188 (99.5%) |
| ≥3 | 0 | 183 (96.8%) |
| ≥4 | 0 | 175 (92.6%) |
| ≥5 | 0 | 1 (0.5%) |
| =6 | 0 | 0 |
| Total dose of guselkumab (mg) | | |
| N | 45 | 189 |
| Mean (SD) | 197.8 (14.91) | 389.4 (43.69) |
| Median | 200.0 | 400.0 |
| Range | (100; 200) | (100; 500) |
| IQ range | (200.0; 200.0) | (400.0; 400.0) |
| Duration of study follow-up (weeks)[a] | | |
| N | 96 | 188 |
| Mean (SD) | 23.8 (2.14) | 23.9 (1.50) |
| Median | 24.0 | 24.0 |
| Range | (4; 26) | (13; 27) |
| IQ range | (23.9; 24.3) | (23.9; 24.3) |

Key:
IQ = interquartile
[a]Duration of study follow-up (week) = date of last visit or last contact or last assessment, whichever is last, through Week 24 visit - reference date + 1)/7.

Statistical Methods:
Efficacy:

The primary analysis of efficacy included all randomized participants who received at least 1 dose (complete or partial) of study agent. In efficacy analyses, participants were analyzed per the randomized treatment group to which they were assigned regardless of the treatments they received. For binary response efficacy endpoints, treatment comparisons were performed using a Cochran-Mantel-Haenszel (CMH) test stratified by baseline use of non-biologic DMARD (yes, no) and prior exposure to 1 or 2 anti-TNFα agents. The magnitude of the treatment difference was estimated by the difference in response rates between the guselkumab and placebo groups with a 95% confidence interval (CI) and p-values, calculated based on Wald statistics.

For continuous endpoints, treatment comparisons were performed using a Mixed-Effect Model Repeated Measures (MMRM) model. The model included all available data from the 2 treatment groups through Week 24. The treatment difference between the guselkumab group and the placebo group was estimated by the difference in the LSmeans. The 95% CIs for the differences in LSmeans and p-values was calculated.

Unless otherwise specified, all treatment group comparisons will be performed at a 2-sided α level of 0.05.

To control the overall Type 1 error rate, the primary endpoint and secondary endpoints were tested in a fixed sequence. The first secondary endpoint (change from baseline in HAQ-DI score at Week 24) was tested only if the primary endpoint (proportion of participants who achieve an ACR 20 response at Week 24) was positive (p<0.05). Similarly, the second (proportion of participants who achieve an ACR 50 response at Week 24), third (change from baseline in SF-36 PCS score at Week 24), and fourth (proportion of participants who achieve PASI 100 response at Week 24 among those with ≥3% BSA and ≥2 IGA at baseline) secondary endpoints were tested only if the previous secondary endpoints were positive (p<0.05). In case one of the primary or secondary endpoints were tested negatively, and formal testing stopped, then 95% confidence intervals and nominal, unadjusted p-values were generated for the remaining endpoints in sequence.

Nominal p-values were reported for exploratory analyses.

Most efficacy analyses were based on the Composite Estimand, which assessed the treatment effects based on variable measurements as well as the intercurrent events defined in the Treatment Failure (TF) criteria. A participant was considered a TF from the earliest date that he/she met any of the following TF criteria onward through Week 24:

Discontinued study agent injections due to any reason.

Terminated study participation due to any reason.

Initiated or increased the dose of non-biologic DMARD (MTX, SSZ, HCQ, LEF) or oral corticosteroids over baseline for PsA.

Initiated protocol prohibited medications/therapies for PsA.

Met Early Escape criteria.

This Estimand acknowledges that meeting the TF criteria is an unfavorable outcome. Thus, for responder type of endpoints, TF implies non-response, and for continuous endpoints TF implies that there is no change from baseline.

Safety:

The safety analysis set included all participants who received at least 1 (complete or partial) dose of study agent. In safety analyses, participants were analyzed per the treatment they received regardless of the treatment group to which they were randomized. Treatment-emergent adverse events, laboratory analyte values, and vital sign measurements during the study were summarized. Treatment-emergent adverse events were coded in accordance with the Medical Dictionary for Regulatory Activities (MedDRA), Version 23.0.

Results:

Study Population:

Of the 285 participants randomized at Week 0 (96 in the placebo group and 189 in the guselkumab group), 5 participants (2 [2.1%] in the placebo group and 3 [1.6%] in the guselkumab group) had discontinued the study by Week 24. In the placebo group, 1 participant withdrew consent and 1 participant discontinued due to "other" reasons. In the guselkumab group, 2 participants withdrew consent and 1 was lost to follow-up.

The demographic characteristics of the participants in the placebo and guselkumab groups were balanced in terms of age (mean [SD]=49.1 [12.14] years and 49.1 [12.31] years, respectively) and BMI (mean [SD]=30.7 [7.12] kg/m2 and 29.0 [5.86] kg/m$^2$, respectively). Participants in both study groups were most frequently obese and had BMI ≥30 kg/m$^2$ at baseline (45.3% [n=43] and 39.2% [n=74] in the placebo and guselkumab groups, respectively). The guselkumab group had a higher proportion of elderly participants (aged ≥65 years) than the placebo group (10.6%, n=20 versus 7.3%, n=7). The proportion of male participants was higher in the placebo group (54.2%, n=52) than in the guselkumab group (45.5%, n=86).

PsA Characteristics at Baseline:

Polyarticular arthritis without rheumatoid nodules (41.7%, [n=40] and 39.4%, [n=74]) and asymmetric peripheral arthritis (37.5% [n=36] and 35.1% [n=66]) were the most frequently reported subtypes in the placebo and guselkumab groups, respectively. In terms of ACR components, the mean (SD) number of swollen and tender joints were 9.0 (5.69) and 18.2 (10.68) respectively, in the placebo group, and 10.2 (6.75) and 21.0 (13.21), respectively, in the guselkumab group. The mean (SD) HAQ-DI scores in the placebo and guselkumab groups were 1.2227 (0.59747) and 1.3305 (0.60157), respectively. Similar mean (SD) CRP levels were observed in the placebo and guselkumab groups (1.154 [2.5358] and 1.225 [1.9583], respectively).

Based on the LEI, 66.7% (n=64) of participants in the placebo group and 67.4% (n=126) in the guselkumab group suffered from enthesitis. Dactylitis was reported by 37.5% (n=36) and 35.8% (n=67) of participants in the placebo and guselkumab groups, respectively.

Psoriasis Characteristics at Baseline:

A total of 61 (63.5%) participants in the placebo group and 120 (63.4%) participants in the guselkumab group reported psoriatic skin disease at baseline. The extent of psoriasis in terms of BSA was most frequently <3% (34.4%, n=33) and ≥3% and <10% (27.1%, n=26) in the placebo group, and ≥20% (31.7%, n=60) and ≥3% and <10% (29.1%, n=55) in the guselkumab group. The mean (SD) PASI scores were 9.2 (9.41) and 11.7 (11.87) in the placebo and guselkumab groups, respectively. The proportion of participants with IGA score ≥2 was 69.8% and 78.8% in the placebo and guselkumab groups, respectively. Scalp psoriasis (78.7% [n=48] and 82.5% [n=99], in the placebo and guselkumab groups, respectively) and nail psoriasis (78.7% [n=48] and 79.2% [n=95], in the placebo and guselkumab groups, respectively) were the most commonly reported psoriatic types at baseline. Hand and/or foot involvement was reported by 21.3% (n=13) and 23.3% (n=28) of participants in the placebo and guselkumab groups, respectively. Baseline DLQI scores indicated a very large and extremely large effect of psoriasis on quality of life reported among participants in both groups (58.3% [n=56] and 63.6% [n=119] in the placebo and guselkumab groups, respectively).

Treatment Failure:

At Week 24, 54.2% (n=52) and 27.0% (n=51) of participants in the placebo and guselkumab groups, respectively, met 1 or more treatment failure criteria. The largest proportion of participants in both study groups were categorized as treatment failures due to Early Escape at Week 16 (46.9% [n=45] and 20.6% [n=39] in the placebo and guselkumab groups, respectively). This also included 20 participants (8 and 12 in the placebo and guselkumab group, respectively) who were incorrectly routed to Early Escape at Week 16 while not fulfilling the Early Escape criterion. Hence, the proportion of participants correctly routed to EE was 38.5% (n=37) and 14.3% (n=27) for the placebo and guselkumab groups respectively.

Extent of Exposure:

Prior to the Week 24 visit, the majority (>92%) of participants in both groups had received ≥4 administrations of study intervention. Participants in the placebo group (Early Escape) and guselkumab group who received SC guselkumab up to Week 24 received an average (SD) of 2.0 (0.15) and 3.9 (0.44) doses of guselkumab, respectively. This translated to a total average (SD) dose of 197.8 mg (14.91 mg) from 2 guselkumab injections in the placebo (Early Escape) group and 389.4 mg (43.69 mg) from 4 guselkumab injections in the guselkumab group.

Efficacy Results:

The Primary Analysis of efficacy was carried out using the Composite Estimand in the Full Analysis Set.

Primary Analysis: ACR 20 Response at Week 24:

ACR 20 response was defined as ≥20% improvement from baseline in both tender joint count (68 joints) and swollen joint count (66 joints), and ≥20% improvement from baseline in at least 3 out of the 5 additional ACR specified assessments. At Week 24, a significantly higher proportion of participants in the guselkumab group achieved ACR 20 response compared with the placebo group (44.4% [n=84] versus 19.8% [n=19]) based on the Composite Estimand; the percentage difference (95% CI) between the groups in favor of guselkumab was 24.6 (14.1, 35.2; p<0.001). See Tables 11 and 12 below.

TABLE 11

Number of Participants Achieving ACR 20 Response
at Week 24 (Primary Analysis) Based on the
Composite Estimand; Full Analysis Set 1

|  | Placebo | Guselkumab 100 mg q8w |
|---|---|---|
| Analysis set: Full Analysis Set 1 | 96 | 189 |
| Participants evaluable for ACR 20 Response at Week 24$^a$ | 96 | 189 |
| Participants with ACR 20 Response$^{b,h}$ | 19 (19.8%) | 84 (44.4%) |
| All Participants (including those with imputed data) | 96 | 189 |

TABLE 11-continued

| | Placebo | Guselkumab 100 mg q8w |
|---|---|---|
| Number of Participants Achieving ACR 20 Response at Week 24 (Primary Analysis) Based on the Composite Estimand; Full Analysis Set 1 | | |
| Participants with ACR 20 Response[b,c,h] | 19 (19.8%) | 84 (44.4%) |
| % Difference (95% CI)[d] | | 24.6 (14.1, 35.2) |
| p-value[e] | | <0.001 |

Key:
ACR = American College of Rheumatology,
CI = confidence interval,
CMH = Cochran-Mantel-Haenszel,
CRP = C-reactive protein,
DMARD = Disease-Modifying Antirheumatic Drug,
HAQ-DI = Health Assessment Questionnaire-Disability Index,
TNF = tumor necrosis factor
[a]Participants either have an observed ACR 20 response status or met a TF criterion.
[b]Defined as observed responders who had not met any TF criteria prior to this visit.
[c]Participants with missing data are assumed to be non-responders.
[d]The confidence intervals are based on the Wald statistic.
[e]The p-values are based on the CMH test, stratified by baseline use of non-biologic DMARD (yes, no) and prior exposure to anti-TNFα agents (1 or 2).
[h]ACR 20 response is defined as ≥20% improvement from baseline in both tender joint count (68 joints) and swollen joint count (66 joints), and ≥20% improvement from baseline in at least 3 of the following 5 assessments: patient's assessment of pain, patient's global assessment of disease activity, physician's global assessment of disease activity, HAQ-DI, and CRP.
Note:
Under the Composite strategy, treatment effects are assessed not only based on the variable measurements, but also on intercurrent events defined in TF criteria. The participant is considered a non-responder if the participant meets any TF criteria.

TABLE 12

Proportion of Participants Achieving ACR20 Responses at Week 24 by Analysis Set

| | Placebo (%) | Guselkumab (%) | % Difference (95% CI) | p-value |
|---|---|---|---|---|
| Primary Analysis | 19.8 | 44.4 | 24.6 (14.1, 35.2) | <0.001 |
| Per-protocol Analysis | 23.8 | 48.8 | 25.0 (13.1, 36.9) | <0.001 |
| Observed Week 24 data analysis regardless of meeting the TF criteria (Supplementary Analysis 1) | 43.4 | 54.4 | 10.9 (−1.3, 23.2) | 0.081 |
| Adjusted TF discontinuation criterion analysis (Supplementary Analysis 1a) | 20.8 | 46.0 | 25.2 (14.5, 35.9) | <0.001 |
| Analysis correcting the EE error by ignoring the EE TF Criterion (Supplementary Analysis 2) | 19.8 | 48.1 | 28.2 (17.7, 38.8) | <0.001 |
| Analysis correcting the EE error by Affected Data Replacement using MI (Supplementary Analysis 2a) | 19.8 | 44.4 | 25.8 (14.7, 36.9) | <0.001 |

Secondary Analyses:

Change in HAQ-DI from Baseline to Week 24:

The HAQ-DI measures the functional status of participants, being scored on a scale of 0 to 3 with lower scores indicating higher functionality. At Week 24, a significantly greater mean reduction from baseline was observed in the guselkumab group compared with the placebo group (LS mean (95% CI)=0.178 [−0.269, −0.086] versus −0.009 [−0.120, −0.102]). The mean difference (95% CI) between the groups in favor of guselkumab was −0.169 (−0.279, −0.059, p=0.003). See Tables 13 and 14.

TABLE 13

Summary of the Change from Baseline in HAQ-DI Score at Week 24 Based
on the Composite Estimand Using an MMRM Model; Full Analysis Set 1

| | Placebo | Guselkumab 100 mg q8w |
|---|---|---|
| Analysis set: Full Analysis Set 1 | 96 | 189 |
| Change from baseline in HAQ-DI[a,d] | | |
| Participants evaluable[b] | | |
| N | 96 | 189 |
| Mean (SD) | −0.052 (0.3553) | −0.249 (0.5218) |
| Median | 0.000 | −0.125 |
| Range | (−1.25; 1.38) | (−1.88; 1.75) |
| IQ range | (0.000; 0.000) | (−0.500; 0.000) |
| Model Based Estimates of the Mean Change[c] | | |
| LSMean (95% CI) | −0.009 (−0.120, 0.102) | −0.178 (−0.269, −0.086) |
| LSMean difference (95% CI) | | −0.169 (−0.279, −0.059) |
| p-value | | 0.003 |

Key:

HAQ-DI = Health Assessment Questionnaire-Disability Index,

CI = confidence interval,

IQ = interquartile,

MMRM = Mixed Model for Repeated Measures

[a]Defined as the change from baseline using observed data or 0 (no improvement) if a participant met TF criteria prior to Week 24.

[b]Participants either have an observed change from baseline at this visit or met TF criteria prior to this visit.

[c]LSMeans and p-values are based on a mixed model for repeated measures (MMRM) under the missing at random (MAR) assumption for missing data

[d]The HAQ score is the average of the computed categories scores (dressing, arising, eating, walking, hygiene, gripping and daily living). Lower scores are indicative of better functioning.

Note:

Under the Composite strategy, treatment effects are assessed not only based on the variable measurements, but also on intercurrent events defined in TF criteria. The participant is assigned a score of no improvement for continuous variables if the participant meets any TF criteria.

TABLE 14

Mean Change from Baseline in HAQ-DI Scores at Week 24 by Analysis Set

| | Placebo (LSMean) | Guselkumab (LSMean) | LSMean Difference (95% CI) | p-value |
|---|---|---|---|---|
| Primary Analysis | −0.009 | −0.178 | −0.169 (−0.279, −0.059) | 0.003 |
| Per-protocol Analysis | −0.039 | −0.203 | −0.165 (−0.289, −0.040) | 0.010 |
| Observed Week 24 data analysis regardless of meeting the TF criteria (Supplementary Analysis 1) | −0.142 | −0.248 | −0.106 (−0.229, 0.017) | 0.091 |
| Analysis correcting the EE error by ignoring the EE TF Criterion (Supplementary Analysis 2) | −0.026 | −0.222 | −0.196 (−0.307, −0.084) | <0.001 |
| Analysis correcting the EE error by Affected Data Replacement using MI (Supplementary Analysis 2a) | −0.046 | −0.206 | −0.160 (−0.276, −0.045) | 0.007 |

ACR 50 Response at Week 24:

ACR 50 response was defined as ≥50% improvement from baseline in the ACR response criteria. At Week 24, a significantly greater proportion of participants in the guselkumab group (19.6%, n=37) achieved ACR 50 response, compared with the placebo group (5.2%, n=5). The percentage difference (95% CI) between the groups in favor of guselkumab was 14.3 (7.2, 21.4; p=0.001). See Tables 15 and 16.

TABLE 15

Number of Participants Achieving ACR 50 Response at Week 24 Based on the Composite Estimand; Full Analysis Set 1

|  | Placebo | Guselkumab 100 mg q8w |
|---|---|---|
| Analysis set: Full Analysis Set 1 | 96 | 189 |
| Participants evaluable for ACR 50 Response at Week 24[a] | 96 | 189 |
| Participants with ACR 50 Response[b,h] | 5 (5.2%) | 37 (19.6%) |
| All Participants (including those with imputed data) | 96 | 189 |
| Participants with ACR 50 Response[b,c,h] | 5 (5.2%) | 37 (19.6%) |
| % Difference (95% CI)[d] |  | 14.3 (7.2, 21.4) |
| p-value[e] |  | 0.001 |

Key:
ACR = American College of Rheumatology,
CI = confidence interval,
CMH = Cochran-Mantel-Haenszel,
CRP = C-reactive protein,
DMARD = Disease-Modifying Antirheumatic Drug,
HAQ-DI = Health Assessment Questionnaire-Disability Index,
TNF = tumor necrosis factor
[a]Participants either have an observed ACR 50 response status or met a TF criterion.
[b]Defined as observed responders who had not met any TF criteria prior to this visit.
[c]Participants with missing data are assumed to be non-responders.
[d]The confidence intervals are based on the Wald statistic.
[e]The p-values are based on the CMH test, stratified by baseline use of non-biologic DMARD (yes, no) and prior exposure to anti-TNFα agents (1 or 2).
[h]ACR 50 response is defined as ≥50% improvement from baseline in both tender joint count (68 joints) and swollen joint count (66 joints), and ≥50% improvement from baseline in at least 3 of the 5 assessments: patient's assessment of pain, patient's global assessment of disease activity, physician's global assessment of disease activity, HAQ-DI, and CRP.
Note:
Under the Composite strategy, treatment effects are assessed not only based on the variable measurements, but also on intercurrent events defined in TF criteria. The participant is considered a non-responder if the participant meets any TF criteria.

TABLE 16

Proportion of Participants Achieving ACR 50 Responses at Week 24 by Analysis Set

|  | Placebo (%) | Guselkumab (%) | % Difference (95% CI) | p-value |
|---|---|---|---|---|
| Primary Analysis | 5.2 | 19.6 | 14.3 (7.2, 21.4) | 0.001 |
| Per-protocol Analysis | 6.3 | 21.5 | 15.3 (7.3, 23.3) | 0.002 |
| Observed Week 24 data analysis regardless of meeting the TF criteria (Supplementary Analysis 1) | 9.5 | 23.6 | 14.0 (5.6, 22.4) | 0.004 |
| Analysis correcting the EE error by ignoring the EE TF Criterion (Supplementary Analysis 2) | 5.2 | 21.2 | 15.8 (8.6, 23.0) | <0.001 |
| Analysis correcting the EE error by Affected Data Replacement using MI (Supplementary Analysis 2a) |  |  | 14.0 (5.6, 22.3) | 0.001 |

Change in SF-36 PCS from Baseline to Week 24:

At Week 24, a significantly greater improvement from baseline in the SF-36 PCS score was observed in the guselkumab group compared with the placebo group (LS mean [95% CI]=3.514 [2.314, 4.715] versus −0.387 [−1.841, 1.067], respectively). The LS mean difference between the groups in favor of guselkumab was 3.901 (95% CI=2.457, 5.346; p<0.001). See Tables 17 and 18.

TABLE 17

Summary of the Change from Baseline in SF-36 PCS Score at Week 24 Based
on the Composite Estimand Using an MMRM Model; Full Analysis Set 1

|  | Placebo | Guselkumab 100 mg q8w |
|---|---|---|
| Analysis set: Full Analysis Set 1 Change from baseline in PCS$^{a,d}$ Participants evaluable$^b$ | 96 | 189 |
| N | 96 | 188 |
| Mean (SD) | 0.813 (4.4025) | 4.823 (6.6107) |
| Median | 0.000 | 3.245 |
| Range | (−13.46; 13.83) | (−11.11; 31.33) |
| IQ range | (0.000; 0.570) | (0.000; 8.260) |
| Model Based Estimates of the Mean Change$^c$ |  |  |
| LSMean (95% CI) | −0.387 (−1.841, 1.067) | 3.514 (2.314, 4.715) |
| LSMean difference (95% CI) |  | 3.901 (2.457, 5.346) |
| p-value |  | <0.001 |

Key: CI = confidence interval, IQ = interquartile, PCS = physical component summary, SF-36 = Short-Form-36
(items), MMRM = Mixed Model for Repeated Measures.
$^a$Defined as the change from baseline using observed data or 0 (no improvement) if a participant met TF criteria prior
to Week 24..
$^b$Participants either have an observed change from baseline at this visit or met TF criteria prior to this visit.
$^c$LSMeans and p-values are based on a mixed model for repeated measures (MMRM) under the MAR assumption
for missing data.
$^d$The PCS is calculated based on the 8 scales of the SF-36 Health-Related Quality of Life instrument with 36
questions. Higher scores indicate better health.
Note:
Under the Composite strategy, treatment effects are assessed not only based on the variable measurements, but also
on intercurrent events defined in TF criteria. The participant is assigned a score of no improvement for continuous
variables if the participant meets any TF criteria.

TABLE 18

Summary of Mean Change from Baseline in SF-36 Scores at Week 24 by Analysis Set

|  | Placebo (LSMean) | Guselkumab (LSMean) | LSMean Difference (95% CI) | p-value |
|---|---|---|---|---|
| Primary Analysis | −0.387 | 3.514 | 3.901 (2.457, 5.346) | <0.001 |
| Per-protocol Analysis | −0.097 | 3.903 | 4.000 (2.395, 5.605) | <0.001 |
| Observed Week 24 data analysis regardless of meeting the TF criteria (Supplementary Analysis 1) | 2.835 | 5.278 | 2.443 (0.752, 4.134) | 0.005 |
| Analysis correcting the EE error by ignoring the EE TF Criterion (Supplementary Analysis 2) | −0.035 | 4.275 | 4.310 (2.834, 5.786) | <0.001 |
| Analysis correcting the EE error by Affected Data Replacement using MI (Supplementary Analysis 2a) | −0.192 | 3.911 | 4.103 (2.580, 5.626) | <0.001 |

PASI 100 Response at Week 24 Among Participants with
BSA ≥3% and IGA Score ≥2 at Baseline:

At Week 24, the proportion of those achieving a PASI 100
response was significantly higher in the guselkumab group
than in the placebo group (30.8% [n=41]) versus 3.8%
[n=2], respectively). The percentage difference (95% CI)
between the groups in favor of guselkumab was 27.4 (17.9,
36.8; p<0.001). See Tables 19 and 20.

TABLE 19

Number of Participants Achieving PASI 100 Response at Week 24 Based on the
Composite Estimand Among the Participants who had ≥3% BSA Psoriatic
Involvement and an IGA Score of ≥2 (Mild) at Baseline; Full Analysis Set 1

|  | Placebo | Guselkumab 100 mg q8w |
|---|---|---|
| Analysis set: Full Analysis Set 1 Among the Participants Who had ≥3% BSA of Psoriatic Involvement and an IGA Score ≥2 (mild) at Baseline | 53 | 133 |

TABLE 19-continued

Number of Participants Achieving PASI 100 Response at Week 24 Based on the
Composite Estimand Among the Participants who had ≥3% BSA Psoriatic
Involvement and an IGA Score of ≥2 (Mild) at Baseline; Full Analysis Set 1

|  | Placebo | Guselkumab 100 mg q8w |
| --- | --- | --- |
| Participants evaluable for PASI 100 response[a] | 53 | 133 |
| Participants with PASI 100 response[b,h] | 2 (3.8%) | 41 (30.8%) |
| All Participants (including those with imputed data) | 53 | 133 |
| Participants with PASI 100 response[b,c,h] | 2 (3.8%) | 41 (30.8%) |
| % Difference (95% CI)[d] |  | 27.4 (17.9, 36.8) |
| p-value[e] |  | <0.001 |

Key:
BSA = body surface area,
CI = confidence interval,
CMH = Cochran-Mantel-Haenszel,
CRP = C-reactive protein,
DMARD = Disease-Modifying Antirheumatic Drug,
PASI = Psoriasis Area and Severity Index,
TNF = tumor necrosis factor
[a]Participants either have an observed PASI 100 Response status or met a TF criterion.
[b]Defined as observed responders who had not met any TF criteria prior to Week 24.
[c]Participants with missing data are assumed to be non-responders.
[d] The confidence intervals are based on the Wald statistic.
[e]The p-values are based on the CMH test, stratified by baseline use of non-biologic DMARD (yes, no) and prior exposure to anti-TNFα agents (1 or 2).
[h]The PASI score is a composite of the state of erythema, induration and scaling over the body along with the area of the involvement of psoriatic lesions. The PASI score ranges from 0 to 72, with a higher score indicating more severe disease. PASI 100 response is defined as 100% improvement from baseline in PASI score.
Note:
Under the Composite strategy, treatment effects are assessed not only based on the variable measurements, but also on intercurrent events defined in TF criteria. The participant is considered a non-responder if the participant meets any TF criteria.

TABLE 20

Proportion of Participants Achieving PASI 100 Response at Week 24 Based on
the Composite Estimand Among the Participants who had ≥3% BSA Psoriatic
Involvement and an IGA Score of ≥2 (Mild) at Baseline; Full Analysis Set 1

|  | Placebo (%) | Placebo Guselkumab (%) | Guselkumab 100 mg q8w % Difference (95% CI) | p-value p-value |
| --- | --- | --- | --- | --- |
| Primary Analysis | 3.8 | 30.8 | 27.4 (17.9, 36.8) | <0.001 |
| Per-protocol Analysis | 4.8 | 34.7 | NE | <0.001 |
| Observed Week 24 data analysis regardless of meeting the TF criteria (Supplementary Analysis 1) | 15.1 | 39.8 | 25.1 (12.7, 37.5) | 0.001 |
| Analysis correcting the EE error by ignoring the EE TF Criterion (Supplementary Analysis 2) | 3.8 | 33.8 | 30.1 (20.5, 39.8) | <0.001 |
| Analysis correcting the EE error by Affected Data Replacement using MI (Supplementary Analysis 2a) | 3.8 | 30.8 | 29.0 (18.1, 39.8) | <0.001 |

Exploratory Analyses

Change from baseline in SF-36 MCS score at Week 24 was calculated based on 8 scales of the SF-36 instrument, where higher scores indicated better health. At Week 24, the LS mean (95% CI) change in SF-36 scores was numerically higher in the guselkumab group (2.095 [0.540, 3.650]) than in the placebo group (0.364 [−1.525, 2.252]). The mean difference (95% CI) between the groups was 1.731 (−0.144, 3.606). Although similar results were obtained from the analysis using all observed Week 24 data regardless of meeting the TF criteria, the mean difference (95% CI) (0.909 [−1.222, 3.040]) between the groups was lower compared with the results from the Primary Analysis. For the analysis correcting the EE error by ignoring the EE TF Criterion, the mean difference (95% CI) (2.075 [0.178, 3.972]) between the groups in favor of guselkumab was greater than the result obtained in the Primary Analysis At baseline, a total of 64 (66.7%) participants in the placebo group and 126 (67.4%) participants in the guselkumab group suffered from enthesitis, with a LEI score >0. Change from baseline in enthesitis is measured with the LEI at Week 24. The LEI is calculated based on 6 enthesitis sites, with a negative change from baseline indicating improvement. At Week 24, a greater improvement in enthesitis from baseline was observed in the guselkumab group compared with the placebo group (LS mean [95% CI]=−1.377 [−1.738, −1.015] versus −0.680 [−1.125, −0.235], respectively). The mean difference (95% CI) between the groups in favor of guselkumab was −0.697 (−1.145, −0.248). Similar results were obtained for the analysis using all observed Week 24 data regardless of meeting the TF criteria (Supplementary Analysis 1); however, the mean difference (95% CI) (−0.269 [−0.728, 0.189]) between the groups was lower than the results from the Primary Analysis).

Changes from baseline in enthesitis at Week 24 among the participants with SPARCC score >0 at baseline was measured. The SPARCC measure of enthesitis was based on applying pressure to the 16 entheses of interest and evaluating pain at the site, and a negative score indicated improvement. At Week 24, a greater improvement in enthesitis from baseline was observed in the guselkumab group compared with the placebo group (LS mean [95% CI]=−2.049 [−2.719, −1.380]) versus −1.150 [−1.978, −0.322], respectively). A mean difference (95% CI) of −0.899 (−1.735, −0.063) was observed between the groups in favor of guselkumab. Similar results were obtained for the analysis using all observed Week 24 data regardless of meeting the TF criteria; however, the mean difference (95% CI) (−0.496 [−1.403, 0.412]) between the groups was lower than the Primary Analysis.

A total of 36 (37.5%) participants in the placebo group and 67 (35.8%) participants in the guselkumab group were suffering from dactylitis at baseline. The change from baseline in dactylitis among participants with dactylitis at baseline was measured. Dactylitis was scored on a scale of 0 to 60, with a maximum score of 3 for each digit and a negative change from baseline scores indicating improvement. At Week 24, participants in the guselkumab group registered a numerically greater mean reduction from baseline in dactylitis score, compared with the placebo group (LS mean [95% CI]=−2.488 [−3.704, −1.273] versus −1.282 [−2.695, 0.131], respectively). A mean difference (95% CI) of −1.206 (−2.621, 0.208) was observed between the groups. Contrasting results were observed in the analysis using all observed Week 24 data regardless of meeting the TF criteria, where the mean improvement (95% CI) (0.323 [−1.087, 1.733]) in dactylitis in the guselkumab group was lower than the placebo group.

The change from baseline in FACIT-F scores at Week 24 was measured. FACIT-F scores ranged from 0-52, with higher scores indicating less fatigue. At Week 24, a greater mean increase in FACIT-F score was observed in the guselkumab group (4.607 [3.102, 6.113]), compared with the placebo group (1.050 [−0.780, 2.881]). The mean difference (95% CI) between the groups in favor of guselkumab was 3.557 (1.741, 5.373). The results from the analysis using all observed Week 24 data regardless of meeting the TF criteria were similar to the Primary Analysis. However, the mean difference (95% CI) between the groups (2.979 [0.859, 5.098]) in favor of guselkumab was smaller than for the Primary Analysis.

The change from baseline in swollen and tender joint count by visit up to Week 24 was measured. Tender and swollen joints were counted from a total of 68 and 66 evaluable joints, respectively. The change at each time-point was measured from a baseline of 0 (no improvement), with a positive value denoting an increase and a negative value denoting a decrease in swollen or tender joints. The improvement in tender and swollen joints following guselkumab treatment was apparent from Week 8, where a mean (95% CI) difference of −3.308 (−5.487, −1.129) and −1.847 (−3.074, −0.620), respectively, favoring guselkumab was observed between the groups. The divergence between the interventions at Week 8 increased over time, and a mean difference (95% CI) of −3.965 (−6.046, −1.884) and −2.433 (−3.638, −1.228) in favor of guselkumab was observed in tender and swollen joint counts, respectively, at Week 24.

The change from baseline in DAS28 CRP at Week 24 was measured. The DAS28 combines tender joint count (28 joints), swollen joint count (28 joints), CRP, and Patient's Global Assessment of Disease Activity, and a higher score indicates greater PsA severity. At Week 4, a greater reduction in the mean DAS28 score was observed in the guselkumab group compared with the placebo group. The mean difference (95% CI) between the groups in favor of guselkumab was −0.272 (−0.449, −0.095). The difference between the groups was maintained over time, increasing from Week 4 to Week 24; at Week 24, the mean difference (95% CI) between the groups in favor of guselkumab was −0.655 (−0.898, −0.412). A similar result was obtained for the analysis using all observed Week 24 data regardless of meeting the TF criteria; the mean difference (95% CI) between the groups at Week 4 was −0.259 (−0.439, −0.079). The difference between the groups increased over subsequent time-points, the mean difference (95% CI) between the groups at Week 24 being −0.474 (−0.728, −0.221).

The change in DAPSA scores from baseline was measured. The DAPSA score is a composite of tender and swollen joint counts, CRP, patient's assessment of pain and patient's global assessment of arthritis disease activity, and a higher DAPSA score indicates greater disease severity. At Week 24, a greater mean (95% CI) reduction in DAPSA scores from baseline was observed in the guselkumab group (−14.541 [−17.639, −11.443]) compared with the placebo group (−5.754 [−9.517, −1.991]). The mean difference (95% CI) between the groups in favor of guselkumab was −8.787 (−12.538, −5.036). The Observed Week 24 Data Analysis results were consistent with the results from the Primary Analysis, however the magnitude of difference (95% CI) (−5.764 [−9.595, −1.933]) between the groups was lower.

The proportion of participants who achieved a ≥20%, ≥50%, ≥70%, and ≥90% improvement from baseline in BASDAI score by visit through Week 24 was measured. The BASDAI is based on 6 questions relating to 5 major symptoms of ankylosing spondylitis through a patient's self-assessment. Higher scores indicate greater disease severity and a score decrease of 50% or 2 points is considered clinically meaningful. Among the subset of participants who suffered from spondylitis and peripheral joint involvement as their primary arthritic presentation in the placebo (26 [27.1%]) and guselkumab (47 [25.0%]) groups, similar proportions of participants in the placebo and guselkumab groups achieved ≥20% improvement (34.6% [n=9] and 31.9% [n=15], respectively) and ≥50% improvement (5 (19.2% [n=5] and 19.1% [n=9], respectively) in BASDAI scores at Week 24. A ≥70% and ≥90% improvement in scores was observed only in the guselkumab group (2.8% [n=6] and 2.1% [n=1], respectively).

Change from baseline in mCPDAI by visit through Week 24 was measured. The mCPDAI score is calculated from a combination of the tender and swollen joint counts, HAQ-DI, PASI, DLQI, dactylitis and enthesitis. The final score ranges from 0-12, with a higher score indicating greater disease severity. At Week 16 and Week 24, a greater mean (95% CI) reduction from baseline in the mCPDAI score was observed in the guselkumab group (−1.913 [−2.334, −1.493] and −1.853 [−2.318, −1.388], respectively) compared with the placebo group (−0.560 [−1.061, −0.058] and −0.426 [−0.981, 0.130], respectively). The mean differences (95% CI) between the groups in favor of guselkumab at Week 16 and Week 24 were −1.354 (−1.850, −0.858) and −1.428 (−1.974, −0.881), respectively. Similar results were obtained from the analysis using all observed Week 24 data regardless of meeting the TF criteria, however the magnitude of difference (95% CI) at Week 24 (−0.864 [−1.389, −0.339]) between the groups in favor of guselkumab was lower compared with the Primary Analysis.

The change from baseline in GRACE scores at Week 24, based on the Composite Estimand was measured. The GRACE index score is calculated from the arithmetic mean of the desirability function (AMDF). The AMDF is a function of the tender and swollen joint counts, HAQ-D score, patient's global assessment of disease activity (arthritis and psoriasis), patient's assessment of skin disease activity, patient's global assessment of disease activity (arthritis), PASI score, and psoriatic arthritis quality of life index score. A higher GRACE score indicates greater disease severity. At Week 16 and Week 24, a greater mean reduction (95% CI) from baseline in the GRACE score was observed in the guselkumab group (−1.451 [−1.749, −1.153] and −1.538 [−1.850, −1.225], respectively) compared with the placebo group (−0.363 [−0.720, −0.005] and −0.287 [−0.663, 0.088], respectively). This was indicative of reduced disease activity in the guselkumab group from baseline to Week 24. The mean differences (95% CI) between the groups in favor of guselkumab at Week 16 and Week 24 were −1.089 (−1.446, −0.731) and −1.251 (−1.626, −0.876), respectively. Similar results were obtained from the analysis using all observed Week 24 data regardless of meeting the TF criteria, however the magnitude of difference (95% CI) (−0.815 [−1.181, −0.450]) between the groups at Week 24 in favor of guselkumab was lower compared with the Primary Analysis.

Results of participants who achieve low disease activity (≤2.3) based on GRACE through Week 24 was measured. At Week 16 and Week 24, low disease activity was observed among a greater proportion of participants in the guselkumab group (15.3% [n=29] and 17.5% [n=33], respectively) compared with the placebo group (5.2% [n=5] and 3.1% [n=3], respectively). The percentage differences (95% CI) between the groups at Week 16 and Week 24 in favor of guselkumab were 10.1 (3.4, 16.8) and 14.3 (7.9, 20.6), respectively. At baseline, a total of 64 (66.7%) participants in the placebo group and 126 (67.4%) participants in the guselkumab group suffered from enthesitis, with a LEI score >0.

At Week 24, resolution of enthesitis was defined as no enthesitis in participants who had at least 1 (out of a total of 6) enthesitis site(s) at baseline. At Week 24, a higher proportion of participants in the guselkumab group (39.7% [n=50]) reported resolution of enthesitis, compared with the placebo group (18.8% [n=12]). The percentage difference (95% CI) at Week 24 between the groups in favor of guselkumab was 21.6 (8.8, 34.4). Similar results were obtained from the analysis using all observed Week 24 data regardless of meeting the TF criteria; however the percentage difference (95% CI) (11.0 [−3.7, 25.7]) between the groups in favor of guselkumab was lower than that obtained from the Primary Analysis.

The proportion of participants achieving resolution of enthesitis (LEI) by visit through Week 24 based on the Composite Estimand and for the analysis using all observed Week 24 data regardless of meeting the TF criterianalysis 1) among the participants with enthesitis (LEI) at baseline are presented in Attachment TEFENL05 and Attachment TEFENL06, respectively.

A total of 36 (37.5%) participants in the placebo group and 67 (35.8%) participants in the guselkumab group were suffering from dactylitis at baseline. The proportion of participants achieving resolution of dactylitis at Week 24 was measured. Dactylitis is scored on a scale of 0 to 60, with a maximum score of 3 for each digit (hand and feet).

Resolution of dactylitis was defined as a score of 0 for a participant who had a score above zero at baseline. At Week 24, a greater proportion of participants in the guselkumab group (44.8%, n=30) achieved resolution of dactylitis compared with the placebo group (25.0%, n=9). A percentage difference (95% CI) of 19.9 (2.7, 37.1) was observed between the groups in favor of guselkumab. The results from the analysis using all observed Week 24 data regardless of meeting the TF criteria were in contrast to the Primary Analysis; a numerically greater proportion of participants in the placebo group (63.9%, n=23) achieved resolution of dactylitis compared with the guselkumab group (59.7%, n=40). The percentage difference (95% CI) between the groups was −3.0 (−21.8, 15.8).

The proportion of participants achieving MDA and VLDA at Week 24 was measured. Minimal disease activity (MDA) is defined as achieving 5 of the following 7 criteria: tender joint count ≤1, swollen joint count ≤1, psoriasis activity and severity index ≤1, patient's assessment of pain ≤15, patient's global assessment of disease activity ≤20, HAQ-DI score ≤0.5, tender enthesis points ≤1. Very low disease activity (VLDA) was achieved if all 7 of the following criteria are met. At Week 24, a greater proportion of participants in guselkumab group (14.8%, n=28) achieved MDA response, compared with the placebo group (3.1%, n=3). The percentage difference (95% CI) between the groups in favor of guselkumab was 11.7 (5.6, 17.7). The result from the analysis using all observed Week 24 data regardless of meeting the TF criteria was consistent with the Primary Analysis; the percentage difference (95% CI) between the groups in favor of guselkumab was 11.6 (4.7, 18.5). At Week 24, 7 (3.7%) participants in the guselkumab group had achieved VLDA response, versus none in the placebo group. The results obtained from the analysis using all observed Week 24 data regardless of meeting the TF criteria were identical to the Primary Analysis.

At Week 16 and Week 24, a greater proportion of participants in the guselkumab group (10.6% [n=20] and 14.8% [n=28], respectively) achieved MDA response, compared with the placebo group (3.1%, n=3 at both time-points). The percentage differences (95% CI) between the groups in favor of guselkumab at Week 16 and Week 24 were 7.5 (1.9, 13.0) and 11.7 (5.6, 17.7), respectively. The result from the analysis using all observed Week 24 data regardless of meeting the TF criteria was consistent with the Primary Analysis; the percentage differences (95% CI) between the groups in favor of guselkumab at Week 16 and Week 24 were 7.5 (1.5, 13.5) and 11.6 (4.7, 18.5), respectively. At Week 16, 3 (1.6%) participants in the guselkumab group and 1 (1.0%) participant had achieved VLDA response. By Week 24, 7 (3.7%) participants in the guselkumab group had achieved VLDA response; no participants in the placebo group had achieved VLDA response by Week 24.

Safety Results:

Data sets for the analysis of safety through Week 24 were:

On Placebo: This included 96 participants who were randomized to the placebo group at Week 0. Of these, 51 received only placebo through Week 24, and 45 received placebo until they switched to guselkumab at Week 16. For this set only safety while on placebo is described.

Switched from Placebo to Guselkumab prior to Week 24: This included 45 participants who were randomized to the placebo group, but who met the early escape criteria and switched to guselkumab at Week 16. For this set, only safety events while on guselkumab were described.

Randomized to Guselkumab: This included 189 participants who were randomized to the guselkumab group at Week 0 and received only guselkumab through Week 24. Participants in this set who were assigned early escape placebo injection at Week 16 to maintain the blind were also considered part of this group.

Guselkumab Combined: This included 234 participants who had received at least 1 dose of guselkumab through Week 24, and included those randomized to receive guselkumab at Week 0 (189 participants), plus those from the placebo group who switched to guselkumab prior to Week 24 after early escape (45 participants).

Summary of AEs Through Week 24:

Through Week 24, 46 (47.9%) participants on placebo and 86 (36.8%) participants in the guselkumab combined group reported at least one TEAE, of whom 3 (3.1%) and 8 (3.4%), respectively, reported at least one serious adverse event (SAE), and 2 (2.1%) and 5 (2.1%), respectively, discontinued study intervention due to an AE. Of the participants who switched to guselkumab after early escape, 6 (13.3%) reported at least one TEAE, 1 (2.2%) reported at least one SAE, and none discontinued study intervention due to an AE. The vast majority (>95%) of participants in each group reported AEs of mild or moderate intensity only. No deaths were reported through Week 24.

Related TEAEs Through Week 24:

In the placebo group, infections and infestations (n=8, 8.3%) were the most frequently reported treatment-emergent AEs considered related to study intervention. In the guselkumab combined group, TEAEs considered reasonably related to study intervention were reported by 27 (11.5%) participants, 2 of whom had switched to guselkumab following early escape. The most frequently reported TEAEs with reasonable causality to guselkumab were infections and infestations (n=10, 4.3%), general disorders and administration site conditions (n=6, 2.6%), and abnormalities in laboratory investigations (n=6, 2.6%).

Serious Adverse Events Through Week 24:

Through Week 24, 3 (3.1%) participants on placebo and 8 (3.4%) participants in the guselkumab combined group, of whom 1 had switched to guselkumab after early escape, experienced at least one SAE.

Other Significant Adverse Events:

Through Week 24, 2 (2.1%) participants on placebo and 5 (2.1%) in the guselkumab combined group discontinued study intervention following one or more TEAEs.

Conclusion(s) Week 24:

Treatment with guselkumab 100 mg at Week 0 and Week 4 and then every 8 weeks in this study demonstrated the superiority of guselkumab over placebo with respect to the primary endpoint of ACR 20 response at Week 24. The superiority of guselkumab over placebo was established with respect to all 4 key secondary endpoints at Week 24, based on a predefined hierarchical testing procedure: HAQ-DI, ACR 50 response, SF-36 PCS, and PASI 100.

Overall, guselkumab demonstrated robust efficacy on signs and symptoms of the joints and skin psoriasis, improved physical function, and improvement in the physical component of health-related quality of life.

The guselkumab dosing regimen was safe and well-tolerated through Week 24 in this study. The safety profile of guselkumab through Week 24 in this population of psoriatic arthritis patients who were refractory to anti-TNF therapy is generally consistent with that demonstrated in the psoriasis or bio-naive psoriatic arthritis indication.

Week 48 Efficacy Results

Prior to Week 48, 11.6%, and 13.5% of subjects had discontinued study agent in the GUS and PBO groups, respectively. The most common reasons for discontinuation of study agent were Adverse events (31.8% vs 23.1, respectively), Lack/Loss of Efficacy (22.7% vs 23.1, respectively) and Withdrawal by Subject (22.7% vs 23.1, respectively). Of subjects who continued study agent after Week 24 (174 and 87, respectively, included in the FAS2), 4.0%, and 4.6% of subjects had discontinued study agent after Week 24 and prior to Week 48 in the GUS and PBO groups, respectively. Prior to Week 48, for 45.0%, and 45.8% of subjects with one or more major protocol deviation was reported in the GUS and PBO groups respectively, of which 24.7% and 20.5%, respectively, due to COVID-19. In total, 11 subjects were excluded from the Week 56 per-protocol analysis because a major protocol deviation affected the Week 48 efficacy analysis, based on medical review of the data.

ACR responses

The proportions of subjects achieving an ACR20/50/70 response over time from Week 4 through Week 48 are summarized below. As shown in Tables 21 and 22 below, of GUS randomized subjects, the overall observed proportion of subjects achieving ACR20 response, was 54.9% at Week 24 and further up to 72.3% at Week 48. Of subjects who were routed to Week 16 EE, 36.8% achieved ACR20 response at Week 24 and 58.3% at Week 48. Of those without Week 16 EE, ACR20 response was observed in 59.6% at Week 24 and in 76.2% of subjects at Week 48. Among GUS randomized subjects who achieved ACR20 at Week 24, and who continued the study up to Week 48, 91.2% maintained ACR20 at Week 48, irrespective of taking the EE route.

TABLE 21

Number of Subjects Achieving ACR 20 Response from Baseline by Visit through Week 48 Based on Observed Data for Subjects Randomized to Guselkumab; Full Analysis Set 1 (CNTO1959PSA3003)

| | Guselkumab 100 mg q8w No Early Escape at Week 16 | Guselkumab 100 mg q8w Early Escape at Week 16 | Total |
|---|---|---|---|
| Analysis set: Full Analysis Set 1 Week 4 | 150 | 39 | 189 |
| Subjects evaluable for ACR 20 response[a] | 150 | 39 | 189 |
| Subjects with ACR 20 response | 32 (21.3%) | 4 (10.3%) | 36 (19.0%) |

TABLE 21-continued

Number of Subjects Achieving ACR 20 Response from Baseline by Visit through Week 48 Based on
Observed Data for Subjects Randomized to Guselkumab; Full Analysis Set 1 (CNTO1959PSA3003)

| | Guselkumab 100 mg q8w No Early Escape at Week 16 | Guselkumab 100 mg q8w Early Escape at Week 16 | Total |
|---|---|---|---|
| Week 8 | | | |
| Subjects evaluable for ACR 20 response[a] | 149 | 39 | 188 |
| Subjects with ACR 20 response | 59 (39.6%) | 9 (23.1%) | 68 (36.2%) |
| Week 12 | | | |
| Subjects evaluable for ACR 20 response[a] | 146 | 39 | 185 |
| Subjects with ACR 20 response | 75 (51.4%) | 7 (17.9%) | 82 (44.3%) |
| Week 16 | | | |
| Subjects evaluable for ACR 20 response[a] | 146 | 39 | 185 |
| Subjects with ACR 20 response | 83 (56.8%) | 5 (12.8%) | 88 (47.6%) |
| Week 20 | | | |
| Subjects evaluable for ACR 20 response[a] | 144 | 39 | 183 |
| Subjects with ACR 20 response | 82 (56.9%) | 9 (23.1%) | 91 (49.7%) |
| Week 24 | | | |
| Subjects evaluable for ACR 20 response[a] | 146 | 38 | 184 |
| Subjects with ACR 20 response | 87 (59.6%) | 14 (36.8%) | 101 (54.9%) |
| Week 28 | | | |
| Subjects evaluable for ACR 20 response[a] | 137 | 36 | 173 |
| Subjects with ACR 20 response | 95 (69.3%) | 17 (47.2%) | 112 (64.7%) |
| Week 36 | | | |
| Subjects evaluable for ACR 20 response[a] | 130 | 35 | 165 |
| Subjects with ACR 20 response | 99 (76.2%) | 18 (51.4%) | 117 (70.9%) |
| Week 44 | | | |
| Subjects evaluable for ACR 20 response[a] | 131 | 33 | 164 |
| Subjects with ACR 20 response | 98 (74.8%) | 22 (66.7%) | 120 (73.2%) |
| Week 48 | | | |
| Subjects evaluable for ACR 20 response[a] | 130 | 36 | 166 |
| Subjects with ACR 20 response | 99 (76.2%) | 21 (58.3%) | 120 (72.3%) |

Key:
ACR = American College of Rheumatology,
CRP = C-reactive protein,
DMARD = Disease-Modifying Antirheumatic Drug,
HAQ-DI = Health Assessment Questionnaire Disability Index,
TNF = tumor necrosis factor
[a]ACR 20 response is defined as ≥20% improvement from baseline in both tender joint count (68 joints) and swollen joint count (66 joints), and ≥20% improvement from baseline in at least 3 of the 5 assessments: patient's assessment of pain, patient's global assessment of disease activity, physician's global assessment of disease activity, HAQ-DI, and CRP.

45

TABLE 22

Proportion of Subjects who maintain an ACR 20 response at Week 48 among
Subjects who achieved an ACR 20 response at Week 24 for Subjects Randomized
to Guselkumab; Full Analysis Set 2 (CNTO1959PSA3003)

| | Guselkumab 100 mg q8w No Early Escape at Week 16 | Guselkumab 100 mg q8w Early Escape at Week 16 | Total |
|---|---|---|---|
| Analysis set: Full Analysis Set 2 | 84 | 14 | 98 |
| Week 24 | | | |
| Subjects evaluable for ACR 20 response[a] | 84 | 14 | 98 |
| Subjects with ACR 20 response | 84 (100.0%) | 14 (100.0%) | 98 (100.0%) |
| Week 28 | | | |
| Subjects evaluable for ACR 20 response[a] | 84 | 14 | 98 |
| Subjects with ACR 20 response | 77 (91.7%) | 14 (100.0%) | 91 (92.9%) |

TABLE 22-continued

Proportion of Subjects who maintain an ACR 20 response at Week 48 among
Subjects who achieved an ACR 20 response at Week 24 for Subjects Randomized
to Guselkumab; Full Analysis Set 2 (CNTO1959PSA3003)

| | Guselkumab 100 mg q8w No Early Escape at Week 16 | Guselkumab 100 mg q8w Early Escape at Week 16 | Total |
|---|---|---|---|
| Week 36 | | | |
| Subjects evaluable for ACR 20 response[a] | 83 | 14 | 97 |
| Subjects with ACR 20 response | 77 (92.8%) | 13 (92.9%) | 90 (92.8%) |
| Week 44 | | | |
| Subjects evaluable for ACR 20 response[a] | 82 | 13 | 95 |
| Subjects with ACR 20 response | 72 (87.8%) | 13 (100.0%) | 85 (89.5%) |
| Week 48 | | | |
| Subjects evaluable for ACR 20 response[a] | 77 | 14 | 91 |
| Subjects with ACR 20 response | 70 (90.9%) | 13 (92.9%) | 83 (91.2%) |

Key: ACR = American College of Rheumatology, CRP = C-reactive protein, DMARD = Disease-Modifying
Antirheumatic Drug, HAQ-DI = Health Assessment Questionnaire Disability Index, TNF = tumor necrosis
factor
[a]ACR 20 response is defined as ≥20% improvement from baseline in both tender joint count (68 joints) and
swollen joint count (66 joints), and ≥20% improvement from baseline in at least 3 of the 5 assessments: patient's
assessment of pain, patient's global assessment of disease activity, physician's global assessment of disease
activity, HAQ-DI, and CRP. The full analysis set 2 includes all randomized subjects who were still on study
treatment at Week 24

As shown in Tables 23 and 24 below, in GUS randomized subjects, for subjects who were routed and those who were not routed to Week 16 EE, at Week 24, 13.2% and 26.7% ACR50 response was observed, respectively. At Week 48, this increased to 41.7% and 50.4%, respectively. Overall, 48.5% achieved ACR50 response at Week 48. Among GUS randomized subjects who achieved ACR50 at Week 24, and who continued the study up to Week 48, 94.6% maintained ACR50 at Week 48, irrespective of taking the EE route.

TABLE 23

Number of Subjects Achieving ACR 50 Response from Baseline by
Visit through Week 48 Based on Observed Data for Subjects Randomized
to Guselkumab; Full Analysis Set 1 (CNTO1959PSA3003)

| | Guselkumab 100 mg q8w No Early Escape at Week 16 | Guselkumab 100 mg q8w Early Escape at Week 16 | Total |
|---|---|---|---|
| Analysis set: Full Analysis Set 1 | 150 | 39 | 189 |
| Week 4 | | | |
| Subjects evaluable for ACR 50 response[a] | 150 | 39 | 189 |
| Subjects with ACR 50 response | 1 (0.7%) | 0 | 1 (0.5%) |
| Week 8 | | | |
| Subjects evaluable for ACR 50 response[a] | 149 | 39 | 188 |
| Subjects with ACR 50 response | 16 (10.7%) | 0 | 16 (8.5%) |
| Week 12 | | | |
| Subjects evaluable for ACR 50 response[a] | 146 | 39 | 185 |
| Subjects with ACR 50 response | 28 (19.2%) | 1 (2.6%) | 29 (15.7%) |
| Week 16 | | | |
| Subjects evaluable for ACR 50 response[a] | 146 | 39 | 185 |
| Subjects with ACR 50 response | 30 (20.5%) | 0 | 30 (16.2%) |
| Week 20 | | | |
| Subjects evaluable for ACR 50 response[a] | 144 | 39 | 183 |
| Subjects with ACR 50 response | 38 (26.4%) | 3 (7.7%) | 41 (22.4%) |

TABLE 23-continued

Number of Subjects Achieving ACR 50 Response from Baseline by
Visit through Week 48 Based on Observed Data for Subjects Randomized
to Guselkumab; Full Analysis Set 1 (CNTO1959PSA3003)

| | Guselkumab 100 mg q8w No Early Escape at Week 16 | Guselkumab 100 mg q8w Early Escape at Week 16 | Total |
|---|---|---|---|
| Week 24 | | | |
| Subjects evaluable for ACR 50 response[a] | 146 | 38 | 184 |
| Subjects with ACR 50 response | 39 (26.7%) | 5 (13.2%) | 44 (23.9%) |
| Week 28 | | | |
| Subjects evaluable for ACR 50 response[a] | 137 | 36 | 173 |
| Subjects with ACR 50 response | 39 (28.5%) | 7 (19.4%) | 46 (26.6%) |
| Week 36 | | | |
| Subjects evaluable for ACR 50 response[a] | 132 | 35 | 167 |
| Subjects with ACR 50 response | 54 (40.9%) | 2 (5.7%) | 56 (33.5%) |
| Week 44 | | | |
| Subjects evaluable for ACR 50 response[a] | 130 | 34 | 164 |
| Subjects with ACR 50 response | 63 (48.5%) | 13 (38.2%) | 76 (46.3%) |
| Week 48 | | | |
| Subjects evaluable for ACR 50 response[a] | 131 | 36 | 167 |
| Subjects with ACR 50 response | 66 (50.4%) | 15 (41.7%) | 81 (48.5%) |

Key: ACR = American College of Rheumatology, CRP = C-reactive protein, DMARD = Disease-Modifying Antirheumatic Drug, HAQ-DI = Health Assessment Questionnaire Disability Index, TNF = tumor necrosis factor
[a]ACR 50 response is defined as ≥50% improvement from baseline in both tender joint count (68 joints) and swollen joint count (66 joints), and ≥50% improvement from baseline in at least 3 of the 5 assessments: patient's assessment of pain, patient's global assessment of disease activity, physician's global assessment of disease activity, HAQ-DI, and CRP.

TABLE 24

Proportion of Subjects who maintain an ACR 50 response at Week 48 among
Subjects who achieved an ACR 50 response at Week 24 for Subjects Randomized
to Guselkumab; Full Analysis Set 2 (CNTO1959PSA3003)

| | Guselkumab 100 mg q8w No Early Escape at Week 16 | Guselkumab 100 mg q8w Early Escape at Week 16 | Total |
|---|---|---|---|
| Analysis set: Full Analysis Set 2 | 37 | 5 | 42 |
| Week 24 | | | |
| Subjects evaluable for ACR 50 response[a] | 37 | 5 | 42 |
| Subjects with ACR 50 response | 37 (100.0%) | 5 (100.0%) | 42 (100.0%) |
| Week 28 | | | |
| Subjects evaluable for ACR 50 response[a] | 37 | 5 | 42 |
| Subjects with ACR 50 response | 24 (64.9%) | 4 (80.0%) | 28 (66.7%) |
| Week 36 | | | |
| Subjects evaluable for ACR 50 response[a] | 37 | 5 | 42 |
| Subjects with ACR 50 response | 31 (83.8%) | 2 (40.0%) | 33 (78.6%) |
| Week 44 | | | |
| Subjects evaluable for ACR 50 response[a] | 35 | 5 | 40 |
| Subjects with ACR 50 response | 31 (88.6%) | 3 (60.0%) | 34 (85.0%) |

TABLE 24-continued

Proportion of Subjects who maintain an ACR 50 response at Week 48 among
Subjects who achieved an ACR 50 response at Week 24 for Subjects Randomized
to Guselkumab; Full Analysis Set 2 (CNTO1959PSA3003)

|  | Guselkumab 100 mg q8w No Early Escape at Week 16 | Guselkumab 100 mg q8w Early Escape at Week 16 | Total |
|---|---|---|---|
|  | Week 48 | | |
| Subjects evaluable for ACR 50 response[a] | 32 | 5 | 37 |
| Subjects with ACR 50 response | 30 (93.8%) | 5 (100.0%) | 35 (94.6%) |

Key: ACR = American College of Rheumatology, CRP = C-reactive protein, DMARD = Disease-Modifying
Antirheumatic Drug, HAQ-DI = Health Assessment Questionnaire Disability Index, TNF = tumor necrosis
factor
[a]ACR 50 response is defined as ≥50% improvement from baseline in both tender joint count (68 joints) and
swollen joint count (66 joints), and ≥50% improvement from baseline in at least 3 of the 5 assessments: patient's
assessment of pain, patient's global assessment of disease activity, physician's global assessment of disease
activity, HAQ-DI, and CRP. The full analysis set 2 includes all randomized subjects who were still on study
treatment at Week 24

As shown in Tables 25 and 26 below, of GUS randomized subjects, for subjects routed to Week 16 EE and those without EE, at Week 24, 2.6% and 10.3% ACR70 response was observed, respectively. At Week 48, the ACR70 response rate increased to 22.2% and 30.1%, respectively. Overall, 28.4% achieved ACR70 response at Week 48. Among GUS randomized subjects who achieved ACR70 at Week 24, and who continued the study up to Week 48, 81.3% achieved ACR70 at Week 48.

TABLE 25

Number of Subjects Achieving ACR 70 Response from Baseline by
Visit through Week 48 Based on Observed Data for Subjects Randomized
to Guselkumab; Full Analysis Set 1 (CNTO1959PSA3003)

|  | Guselkumab 100 mg q8w No Early Escape at Week 16 | Guselkumab 100 mg q8w Early Escape at Week 16 | Total |
|---|---|---|---|
| Analysis set: Full Analysis Set 1 | 150 | 39 | 189 |
|  | Week 4 | | |
| Subjects evaluable for ACR 70 response[a] | 150 | 39 | 189 |
| Subjects with ACR 70 response | 0 | 0 | 0 |
|  | Week 8 | | |
| Subjects evaluable for ACR 70 response[a] | 149 | 39 | 188 |
| Subjects with ACR 70 response | 1 (0.7%) | 0 | 1 (0.5%) |
|  | Week 12 | | |
| Subjects evaluable for ACR 70 response[a] | 146 | 39 | 185 |
| Subjects with ACR 70 response | 7 (4.8%) | 1 (2.6%) | 8 (4.3%) |
|  | Week 16 | | |
| Subjects evaluable for ACR 70 response[a] | 146 | 39 | 185 |
| Subjects with ACR 70 response | 12 (8.2%) | 0 | 12 (6.5%) |
|  | Week 20 | | |
| Subjects evaluable for ACR 70 response[a] | 144 | 39 | 183 |
| Subjects with ACR 70 response | 13 (9.0%) | 1 (2.6%) | 14 (7.7%) |
|  | Week 24 | | |
| Subjects evaluable for ACR 70 response[a] | 146 | 38 | 184 |
| Subjects with ACR 70 response | 15 (10.3%) | 1 (2.6%) | 16 (8.7%) |
|  | Week 28 | | |
| Subjects evaluable for ACR 70 response[a] | 137 | 36 | 173 |
| Subjects with ACR 70 response | 14 (10.2%) | 4 (11.1%) | 18 (10.4%) |

TABLE 25-continued

Number of Subjects Achieving ACR 70 Response from Baseline by
Visit through Week 48 Based on Observed Data for Subjects Randomized
to Guselkumab; Full Analysis Set 1 (CNTO1959PSA3003)

| | Guselkumab 100 mg q8w No Early Escape at Week 16 | Guselkumab 100 mg q8w Early Escape at Week 16 | Total |
|---|---|---|---|
| Week 36 | | | |
| Subjects evaluable for ACR 70 response[a] | 134 | 35 | 169 |
| Subjects with ACR 70 response | 26 (19.4%) | 1 (2.9%) | 27 (16.0%) |
| Week 44 | | | |
| Subjects evaluable for ACR 70 response[a] | 132 | 34 | 166 |
| Subjects with ACR 70 response | 30 (22.7%) | 5 (14.7%) | 35 (21.1%) |
| Week 48 | | | |
| Subjects evaluable for ACR 70 response[a] | 133 | 36 | 169 |
| Subjects with ACR 70 response | 40 (30.1%) | 8 (22.2%) | 48 (28.4%) |

Key: ACR = American College of Rheumatology, CRP = C-reactive protein, DMARD = Disease-Modifying
Antirheumatic Drug, HAQ-DI = Health Assessment Questionnaire Disability Index, TNF = tumor necrosis
factor
[a]ACR 70 response is defined as ≥70% improvement from baseline in both tender joint count (68 joints) and
swollen joint count (66 joints), and ≥70% improvement from baseline in at least 3 of the 5 assessments:
patient's assessment of pain, patient's global assessment of disease activity, physician's global assessment
of disease activity, HAQ-DI, and CRP.

TABLE 26

Proportion of Subjects who maintain an ACR 70 response at Week 48 among
Subjects who achieved an ACR 70 response at Week 24 for Subjects Randomized
to Guselkumab; Full Analysis Set 2 (CNTO1959PSA3003)

| | Guselkumab 100 mg q8w No Early Escape at Week 16 | Guselkumab 100 mg q8w Early Escape at Week 16 | Total |
|---|---|---|---|
| Analysis set: Full Analysis Set 2 | 15 | 1 | 16 |
| Week 24 | | | |
| Subjects evaluable for ACR 70 response[a] | 15 | 1 | 16 |
| Subjects with ACR 70 response | 15 (100.0%) | 1 (100.0%) | 16 (100.0%) |
| Week 28 | | | |
| Subjects evaluable for ACR 70 response[a] | 15 | 1 | 16 |
| Subjects with ACR 70 response | 10 (66.7%) | 0 | 10 (62.5%) |
| Week 36 | | | |
| Subjects evaluable for ACR 70 response[a] | 15 | 1 | 16 |
| Subjects with ACR 70 response | 11 (73.3%) | 0 | 11 (68.8%) |
| Week 44 | | | |
| Subjects evaluable for ACR 70 response[a] | 14 | 1 | 15 |
| Subjects with ACR 70 response | 12 (85.7%) | 0 | 12 (80.0%) |
| Week 48 | | | |
| Subjects evaluable for ACR 70 response[a] | 15 | 1 | 16 |
| Subjects with ACR 70 response | 13 (86.7%) | 0 | 13 (81.3%) |

Key: ACR = American College of Rheumatology, CRP = C-reactive protein, DMARD = Disease-Modifying
Antirheumatic Drug, HAQ-DI = Health Assessment Questionnaire Disability Index, TNF = tumor necrosis
factor
[a]ACR 70 response is defined as ≥70% improvement from baseline in both tender joint count (68 joints) and
swollen joint count (66 joints), and ≥70% improvement front baseline in at least 3 of the 5 assessments: patient's
assessment of pain, patient's global assessment of disease activity, physician's global assessment of disease
activity, HAQ-DI, and CRP. The full analysis set 2 includes all randomized subjects who were still on study
treatment at Week 24

HAQ-DI

As shown in Table 27 below, starting from a mean HAQ-DI of 1.33 at baseline, GUS randomized subjects improved on average by 0.29 points at Week 24 and by 0.47 points at Week 48. Subjects who were routed to Week 16 EE, compared to those without EE, had a slightly higher baseline: 1.42 compared to 1.31. Although GUS-randomized subjects who were routed to EE improved less at Week 24 was less at −0.18 compared to −0.32 compared to GUS subjects without EE, improvement between these groups at Week 48 was similar: −0.43 compared to −0.48, respectively.

TABLE 27

Summary of the Observed Value and Change from Baseline in HAQ-DI Score by Visit through Week 48 for Subjects Randomized to Guselkumab; Full Analysis Set 1 (CNTO1959PSA3003)

| | Guselkumab 100 mg q8w No Early Escape at Week 16 | Guselkumab 100 mg q8w Early Escape at Week 16 | Total |
|---|---|---|---|
| Analysis set: Full Analysis Set 1 | 150 | 39 | 189 |
| Week 0 | | | |
| N | 150 | 39 | 189 |
| Mean (SD) | 1.31 (0.629) | 1.42 (0.485) | 1.33 (0.603) |
| Median | 1.38 | 1.38 | 1.38 |
| Range | (0.0; 2.8) | (0.6; 2.8) | (0.0; 2.8) |
| IQ range | (0.88; 1.88) | (1.00; 1.75) | (0.88; 1.88) |
| Week 4 | | | |
| N | 150 | 39 | 189 |
| Mean (SD) | 1.18 (0.621) | 1.32 (0.510) | 1.21 (0.601) |
| Median | 1.13 | 1.25 | 1.13 |
| Range | (0.0; 2.9) | (0.4; 2.8) | (0.0; 2.9) |
| IQ range | (0.75; 1.75) | (1.00; 1.63) | (0.88; 1.75) |
| Change from baseline | | | |
| N | 150 | 38 | 188 |
| Mean (SD) | −0.13 (0.461) | −0.10 (0.357) | −0.12 (0.441) |
| Median | −0.13 | −0.06 | −0.13 |
| Range | (−1.4; 1.9) | (−0.8; 1.1) | (−1.4; 1.9) |
| IQ range | (−0.38; 0.13) | (−0.38; 0.13) | (−0.38; 0.13) |
| Week 8 | | | |
| N | 149 | 39 | 188 |
| Mean (SD) | 1.11 (0.602) | 1.20 (0.517) | 1.13 (0.585) |
| Median | 1.13 | 1.13 | 1.13 |
| Range | (0.0; 2.5) | (0.3; 2.5) | (0.0; 2.5) |
| IQ range | (0.63; 1.50) | (0.88; 1.50) | (0.75; 1.50) |
| Change from baseline | | | |
| N | 149 | 38 | 187 |
| Mean (SD) | −0.20 (0.522) | −0.22 (0.458) | −0.20 (0.509) |
| Median | −0.25 | −0.13 | −0.25 |
| Range | (−1.8; 1.6) | (−1.4; 0.6) | (−1.8; 1.6) |
| IQ range | (−0.50; 0.13) | (−0.63; 0.13) | (−0.50; 0.13) |
| Week 12 | | | |
| N | 146 | 39 | 185 |
| Mean (SD) | 1.02 (0.621) | 1.33 (0.574) | 1.09 (0.622) |
| Median | 1.00 | 1.25 | 1.13 |
| Range | (0.0; 2.6) | (0.0; 2.8) | (0.0; 2.8) |
| IQ range | (0.50; 1.50) | (1.00; 1.63) | (0.63; 1.50) |
| Change from baseline | | | |
| N | 146 | 38 | 184 |
| Mean (SD) | −0.30 (0.578) | −0.09 (0.424) | −0.25 (0.555) |
| Median | −0.25 | −0.06 | −0.25 |
| Range | (−2.0; 1.5) | (−1.0; 1.0) | (−2.0; 1.5) |
| IQ range | (−0.63; 0.00) | (−0.38; 0.13) | (−0.50; 0.13) |

TABLE 27-continued

Summary of the Observed Value and Change from Baseline in HAQ-DI Score by Visit through Week 48 for Subjects Randomized to Guselkumab; Full Analysis Set 1 (CNTO1959PSA3003)

| | Guselkumab 100 mg q8w No Early Escape at Week 16 | Guselkumab 100 mg q8w Early Escape at Week 16 | Total |
|---|---|---|---|
| Week 16 | | | |
| N | 146 | 39 | 185 |
| Mean (SD) | 0.99 (0.626) | 1.38 (0.592) | 1.07 (0.637) |
| Median | 1.00 | 1.38 | 1.00 |
| Range | (0.0; 2.6) | (0.0; 2.4) | (0.0; 2.6) |
| IQ range | (0.63; 1.38) | (1.00; 1.75) | (0.63; 1.50) |
| Change from baseline | | | |
| N | 146 | 38 | 184 |
| Mean (SD) | −0.33 (0.574) | −0.04 (0.447) | −0.27 (0.561) |
| Median | −0.31 | 0.00 | −0.25 |
| Range | (−1.9; 1.9) | (−1.1; 1.0) | (−1.9; 1.9) |
| IQ range | (−0.63; 0.00) | (−0.38; 0.25) | (−0.50; 0.00) |
| Week 20 | | | |
| N | 144 | 39 | 183 |
| Mean (SD) | 1.02 (0.639) | 1.27 (0.577) | 1.07 (0.633) |
| Median | 1.00 | 1.25 | 1.13 |
| Range | (0.0; 2.5) | (0.0; 2.3) | (0.0; 2.5) |
| IQ range | (0.50; 1.50) | (0.75; 1.75) | (0.63; 1.63) |
| Change from baseline | | | |
| N | 144 | 38 | 182 |
| Mean (SD) | −0.31 (0.557) | −0.15 (0.468) | −0.28 (0.542) |
| Median | −0.25 | −0.13 | −0.25 |
| Range | (−2.0; 1.9) | (−1.4; 0.8) | (−2.0; 1.9) |
| IQ range | (−0.63; 0.00) | (−0.38; 0.13) | (−0.63; 0.00) |
| Week 24 | | | |
| N | 146 | 38 | 184 |
| Mean (SD) | 0.99 (0.648) | 1.26 (0.536) | 1.05 (0.635) |
| Median | 1.00 | 1.25 | 1.00 |
| Range | (0.0; 2.6) | (0.3; 2.3) | (0.0; 2.6) |
| IQ range | (0.50; 1.50) | (0.88; 1.63) | (0.50; 1.50) |
| Change from baseline | | | |
| N | 146 | 37 | 183 |
| Mean (SD) | −0.32 (0.580) | −0.18 (0.426) | −0.29 (0.554) |
| Median | −0.25 | −0.13 | −0.25 |
| Range | (−1.9; 1.8) | (−1.1; 0.9) | (−1.9; 1.8) |
| IQ range | (−0.63; 0.00) | (−0.50; 0.13) | (−0.63; 0.00) |
| Week 28 | | | |
| N | 137 | 36 | 173 |
| Mean (SD) | 0.98 (0.638) | 1.15 (0.612) | 1.01 (0.634) |
| Median | 1.00 | 1.13 | 1.00 |
| Range | (0.0; 2.8) | (0.0; 2.4) | (0.0; 2.8) |
| IQ range | (0.50; 1.38) | (0.69; 1.69) | (0.50; 1.38) |
| Change from baseline | | | |
| N | 137 | 35 | 172 |
| Mean (SD) | −0.36 (0.585) | −0.31 (0.465) | −0.35 (0.561) |
| Median | −0.25 | −0.13 | −0.25 |
| Range | (−2.3; 1.3) | (−1.3; 0.5) | (−2.3; 1.3) |
| IQ range | (−0.63; 0.00) | (−0.63; 0.00) | (−0.63; 0.00) |
| Week 36 | | | |
| N | 134 | 35 | 169 |
| Mean (SD) | 0.86 (0.610) | 1.19 (0.602) | 0.93 (0.621) |
| Median | 0.88 | 1.25 | 0.88 |
| Range | (0.0; 2.5) | (0.1; 2.4) | (0.0; 2.5) |
| IQ range | (0.38; 1.25) | (0.75; 1.75) | (0.38; 1.38) |
| Change from baseline | | | |
| N | 134 | 34 | 168 |
| Mean (SD) | −0.45 (0.577) | −0.27 (0.488) | −0.41 (0.563) |
| Median | −0.38 | −0.19 | −0.38 |
| Range | (−2.3; 1.0) | (−1.3; 0.6) | (−2.3; 1.0) |
| IQ range | (−0.75; −0.13) | (−0.63; 0.13) | (−0.75; 0.00) |

TABLE 27-continued

Summary of the Observed Value and Change from Baseline in
HAQ-DI Score by Visit through Week 48 for Subjects Randomized
to Guselkumab; Full Analysis Set 1 (CNTO1959PSA3003)

| | Guselkumab 100 mg q8w No Early Escape at Week 16 | Guselkumab 100 mg q8w Early Escape at Week 16 | Total |
|---|---|---|---|
| | | Week 44 | |
| N | 132 | 35 | 167 |
| Mean (SD) | 0.84 (0.614) | 1.07 (0.637) | 0.89 (0.624) |
| Median | 0.81 | 1.13 | 0.88 |
| Range | (0.0; 2.3) | (0.0; 2.3) | (0.0; 2.3) |
| IQ range | (0.38; 1.25) | (0.50; 1.63) | (0.38; 1.25) |
| | | Change from baseline | |
| N | 132 | 34 | 166 |
| Mean (SD) | −0.48 (0.624) | −0.40 (0.521) | −0.46 (0.604) |
| Median | −0.38 | −0.31 | −0.38 |
| Range | (−2.3; 1.1) | (−1.4; 0.5) | (−2.3; 1.1) |
| IQ range | (−0.88; −0.13) | (−0.88; 0.00) | (−0.88; 0.00) |
| | | Week 48 | |
| N | 136 | 36 | 172 |
| Mean (SD) | 0.86 (0.639) | 1.04 (0.712) | 0.89 (0.657) |
| Median | 0.88 | 1.06 | 0.88 |
| Range | (0.0; 2.5) | (0.0; 2.4) | (0.0; 2.5) |
| IQ range | (0.25; 1.38) | (0.44; 1.44) | (0.25; 1.38) |
| | | Change from baseline | |
| N | 136 | 35 | 171 |
| Mean (SD) | −0.48 (0.604) | −0.43 (0.584) | −0.47 (0.598) |
| Median | −0.38 | −0.25 | −0.38 |
| Range | (−2.3; 1.0) | (−1.5; 0.5) | (−2.3; 1.0) |
| IQ range | (−0.88; −0.13) | (−1.00; 0.00) | (−0.88; 0.00) |

Key: HAQ-DI = Health Assessment Questionnaire Disability Index, IQ = inter-quartile.
[a] The HAQ score is the average of the computed categories scores (dressing, arising, eating, walking, hygiene, gripping and daily living). Lower scores are indicative of better functioning.

SF36-PCS

As shown in Table 28 below, starting from a mean SF36-PCS score of 33.0 at baseline, GUS randomized subjects improved on average by 5.83 points at Week 24 and by 8.44 points at Week 48. Subjects who were routed to EE, compared to those without EE, had a slightly lower baseline: 31.8 compared to 33.3. The average improvements at Week 24 were 5.11 and 6.02, and, at Week 48, 7.83 and 8.60, respectively.

TABLE 28

Summary of the Observed Value and Change from Baseline in
SF-36 PCS Score by Visit Through Week 48 for Subjects Randomized
to Guselkumab; Full Analysis Set 1 (CNTO1959PSA3003)

| | Guselkumab 100 mg q8w No Early Escape at Week 16 | Guselkumab 100 mg q8w Early Escape at Week 16 | Total |
|---|---|---|---|
| Analysis set: Full Analysis Set 1 | 150 | 39 | 189 |
| | | Week 0 | |
| N | 150 | 39 | 189 |
| Mean (SD) | (6.89) | 31.8 (7.32) | 33.0 (6.99) |
| Median | 33.5 | 31.4 | 33.1 |
| Range | (16; 51) | (11; 45) | (11; 51) |
| IQ range | (28.3; 37.5) | (26.8; 36.9) | (28.2; 37.4) |

TABLE 28-continued

Summary of the Observed Value and Change from Baseline in
SF-36 PCS Score by Visit Through Week 48 for Subjects Randomized
to Guselkumab; Full Analysis Set 1 (CNTO1959PSA3003)

| | Guselkumab 100 mg q8w No Early Escape at Week 16 | Guselkumab 100 mg q8w Early Escape at Week 16 | Total |
|---|---|---|---|
| | | Week 8 | |
| N | 149 | 39 | 188 |
| Mean (SD) | 37.07 (8.399) | 33.56 (7.676) | 36.34 (8.357) |
| Median | 37.48 | 35.70 | 36.96 |
| Range | (13.0; 58.5) | (15.7; 45.6) | (13.0; 58.5) |
| IQ range | (30.87; 42.67) | (27.88; 38.96) | (30.40; 41.83) |
| | | Change from baseline | |
| N | 149 | 38 | 187 |
| Mean (SD) | 3.68 (6.867) | 1.91 (6.738) | 3.32 (6.860) |
| Median | 3.59 | 2.11 | 3.39 |
| Range | (−17.2; 21.4) | (−20.3; 21.7) | (−20.3; 21.7) |
| IQ range | (−0.64; 7.84) | (−0.83; 5.04) | (−0.83; 7.29) |
| | | Week 16 | |
| N | 146 | 39 | 185 |
| Mean (SD) | 38.88 (8.556) | 33.66 (9.015) | 37.78 (8.889) |
| Median | 39.35 | 32.78 | 38.19 |
| Range | (16.7; 59.9) | (15.6; 54.7) | (15.6; 59.9) |
| IQ range | (31.73; 45.77) | (27.67; 39.87) | (31.22; 44.00) |
| | | Change from baseline | |
| N | 146 | 38 | 184 |
| Mean (SD) | 5.49 (7.299) | 2.05 (7.706) | 4.78 (7.494) |
| Median | 5.34 | 1.80 | 4.71 |
| Range | (−17.3; 32.8) | (−13.0; 20.3) | (−17.3; 32.8) |
| IQ range | (1.36; 9.05) | (−3.26; 6.70) | (0.46; 9.02) |
| | | Week 24 | |
| N | 146 | 38 | 184 |
| Mean (SD) | 39.48 (8.870) | 36.53 (7.591) | 38.87 (8.685) |
| Median | 40.17 | 35.66 | 39.56 |
| Range | (14.8; 59.5) | (24.3; 58.3) | (14.8; 59.5) |
| IQ range | (32.99; 46.12) | (29.79; 42.46) | (32.37; 44.93) |
| | | Change from baseline | |
| N | 146 | 37 | 183 |
| Mean (SD) | 6.02 (7.224) | 5.11 (7.023) | 5.83 (7.174) |
| Median | 5.72 | 3.47 | 5.25 |
| Range | (−13.2; 31.3) | (−5.0; 23.8) | (−13.2; 31.3) |
| IQ range | (1.60; 10.31) | (0.35; 9.01) | (1.20; 9.90) |
| | | Week 36 | |
| N | 133 | 35 | 168 |
| Mean (SD) | 41.56 (8.729) | 36.57 (9.249) | 40.52 (9.042) |
| Median | 42.18 | 38.19 | 40.65 |
| Range | (21.2; 60.9) | (16.7; 57.5) | (16.7; 60.9) |
| IQ range | (35.17; 47.49) | (31.22; 41.73) | (33.96; 46.02) |
| | | Change from baseline | |
| N | 133 | 34 | 167 |
| Mean (SD) | 8.12 (7.377) | 5.71 (8.125) | 7.63 (7.573) |
| Median | 7.17 | 4.91 | 6.94 |
| Range | (−14.7; 29.8) | (−7.4; 24.2) | (−14.7; 29.8) |
| IQ range | (2.60; 11.86) | (−0.71; 11.35) | (2.33; 11.86) |
| | | Week 48 | |
| N | 136 | 36 | 172 |
| Mean (SD) | 41.69 (8.371) | 39.09 (9.303) | 41.15 (8.612) |
| Median | 41.92 | 38.38 | 41.30 |
| Range | (21.2; 60.4) | (22.5; 60.7) | (21.2; 60.7) |
| IQ range | (35.33; 47.36) | (32.75; 44.76) | (34.42; 47.06) |

TABLE 28-continued

Summary of the Observed Value and Change from Baseline in
SF-36 PCS Score by Visit Through Week 48 for Subjects Randomized
to Guselkumab; Full Analysis Set 1 (CNTO1959PSA3003)

| | Guselkumab 100 mg q8w No Early Escape at Week 16 | Guselkumab 100 mg q8w Early Escape at Week 16 | Total |
|---|---|---|---|
| | Change from baseline | | |
| N | 136 | 35 | 171 |
| Mean (SD) | 8.60 (7.230) | 7.83 (7.497) | 8.44 (7.270) |
| Median | 6.98 | 7.61 | 7.07 |
| Range | (−9.0; 27.1) | (−6.2; 22.7) | (−9.0; 27.1) |
| IQ range | (4.11; 13.67) | (1.76; 13.70) | (3.64; 13.70) |

Key: IQ = inter-quartile, PCS = physical component summary, SF-36 = Short Form-36 (items).
[a] The PCS is calculated based on the 8 scales of the SF-36 Health Related Quality of Life instrument with 36 questions. Higher scores indicate better health.

PASI Responses

PASI100, PASI90 and PASI75 response were assessed among subjects who had ≥3% Body Surface Area (BSA) Psoriatic Involvement and an Investigator's Global Assessment (IGA) Score of ≥2 (Mild) at baseline (enrolment) (respectively 55% and 70% of the overall PBO and GUS population).

As shown in Table 29 below, of GUS randomized subjects, the overall observed proportion of subjects achieving PASI100 response, was 41.1% at Week 24 and increased to 66.1% at Week 48. Of GUS subjects who were routed to Week 16 EE, 53.6% achieved PASI100 response at Week 48 whereas of those without EE 69.9% reached PASI100 response at Week 48. Overall Week 48 response was 84.3% for PASI90 and 93.4% for PASI75.

TABLE 29

Number of Subjects Achieving PASI100 Response, PASI ≥90 Response, PASI ≥75 Response
by Visit Through Week 48 Among the Subjects who had ≥3% Body Surface Area (BSA)
Psoriatic Involvement and an Investigator's Global Assessment (IGA) Score of ≥2 (Mild)
at baseline for Subjects Randomized to Guselkumab; Full Analysis Set 1 (CNTO1959PSA3003)

| | Guselkumab 100 mg q8w No Early Escape at Week 16 | Guselkumab 100 mg q8w Early Escape at Week 16 | Total |
|---|---|---|---|
| Analysis set: Full Analysis Set 1 Among the Subjects Who had ≥3% Body Surface Area (BSA) of Psoriatic Involvement and an IGA Score ≥2 (mild) at Baseline | 103 | 30 | 133 |
| Week 16 | | | |
| Subjects evaluable for PASI100 response[a] | 100 | 30 | 130 |
| Subjects with PASI100 response | 40 (40.0%) | 5 (16.7%) | 45 (34.6%) |
| Week 24 | | | |
| Subjects evaluable for PASI100 response[a] | 100 | 29 | 129 |
| Subjects with PASI100 response | 42 (42.0%) | 11 (37.9%) | 53 (41.1%) |
| Week 48 | | | |
| Subjects evaluable for PASI100 response[a] | 93 | 28 | 121 |
| Subjects with PASI100 response | 65 (69.9%) | 15 (53.6%) | 80 (66.1%) |
| Week 16 | | | |
| Subjects evaluable for PASI90 response[a] | 100 | 30 | 130 |
| Subjects with PASI90 response | 54 (54.0%) | 9 (30.0%) | 63 (48.5%) |
| Week 24 | | | |
| Subjects evaluable for PASI90 response[a] | 100 | 29 | 129 |
| Subjects with PASI90 response | 70 (70.0%) | 14 (48.3%) | 84 (65.1%) |
| Week 48 | | | |
| Subjects evaluable for PASI90 response[a] | 93 | 28 | 121 |
| Subjects with PASI90 response | 80 (86.0%) | 22 (78.6%) | 102 (84.3%) |
| Week 16 | | | |
| Subjects evaluable for PASI75 response[a] | 100 | 30 | 130 |
| Subjects with PASI75 response | 76 (76.0%) | 12 (40.0%) | 88 (67.7%) |
| Week 24 | | | |
| Subjects evaluable for PASI75 response[a] | 100 | 29 | 129 |
| Subjects with PASI75 response | 81 (81.0%) | 17 (58.6%) | 98 (76.0%) |

TABLE 29-continued

Number of Subjects Achieving PASI100 Response, PASI ≥90 Response, PASI ≥75 Response by Visit Through Week 48 Among the Subjects who had ≥3% Body Surface Area (BSA) Psoriatic Involvement and an Investigator's Global Assessment (IGA) Score of ≥2 (Mild) at baseline for Subjects Randomized to Guselkumab; Full Analysis Set 1 (CNTO1959PSA3003)

| | Guselkumab 100 mg q8w No Early Escape at Week 16 | Guselkumab 100 mg q8w Early Escape at Week 16 | Total |
|---|---|---|---|
| Week 48 | | | |
| Subjects evaluable for PASI75 response[a] | 93 | 28 | 121 |
| Subjects with PASI75 response | 89 (95.7%) | 24 (85.7%) | 113 (93.4%) |

Key: BSA = body surface area, CRP = C-reactive protein, IGA = Investigator's Global Assessment, DMARD = Disease-Modifying Antirheumatic Drug, PASI = Psoriasis Area and Severity Index, TNF = tumor necrosis factor
[a]The PASI score is a composite of the state of erythema, induration and scaling over the body along with the area of the involvement of psoriatic lesions. The PASI score ranges from 0 to 72, with a higher score indicating more severe disease. PASI 100 response is defined as 100% improvement from baseline in PASI score.

Tender Joint Counts

As shown in Table 30 below, for GUS randomized subjects, at baseline the average number of tender joints was 21.0 with an average improvement of −10.1 at Week 24 and −12.9 at Week 48. Subjects who were routed to Week 16 EE, compared to those without EE, had on average more tender joints at baseline: 22.9 compared to 20.5. The average improvements at Week 24 were −6.3 and −11.1, and, at Week 48, −12.0 and −13.2, for patients with or without EE, respectively.

TABLE 30

Summary of the Observed Value and Change from Baseline in Tender Joint Count by Visit Through Week 48 for Subjects Randomized to Guselkumab; Full Analysis Set 1 (CNTO1959PSA3003)

| | Guselkumab 100 mg q8w No Early Escape at Week 16 | Guselkumab 100 mg q8w Early Escape at Week 16 | Total |
|---|---|---|---|
| Analysis set: Full Analysis Set 1 | 150 | 39 | 189 |
| Week 0 | | | |
| N | 150 | 39 | 189 |
| Mean (SD) | 20.5 (12.82) | 22.9 (14.73) | 21.0 (13.23) |
| Median | 17.0 | 20.0 | 18.0 |
| Range | (3; 66) | (4; 68) | (3; 68) |
| IQ range | (12.0; 26.0) | (13.0; 28.0) | (12.0; 26.0) |
| Week 4 | | | |
| N | 150 | 38 | 188 |
| Mean (SD) | 15.5 (11.84) | 20.1 (15.25) | 16.4 (12.69) |
| Median | 12.0 | 15.0 | 13.0 |
| Range | (1; 57) | (3; 68) | (1; 68) |
| IQ range | (7.0; 21.0) | (9.0; 25.0) | (7.0; 22.0) |
| Change from baseline | | | |
| N | 150 | 38 | 188 |
| Mean (SD) | −5.0 (7.77) | −2.7 (4.24) | −4.5 (7.24) |
| Median | −3.0 | −2.0 | −3.0 |
| Range | (−44; 11) | (−16; 3) | (−44; 11) |
| IQ range | (−9.0; 0.0) | (−5.0; 0.0) | (−8.0; 0.0) |
| Week 8 | | | |
| N | 149 | 39 | 188 |
| Mean (SD) | 12.6 (11.33) | 19.9 (13.81) | 14.1 (12.21) |
| Median | 9.0 | 15.0 | 10.0 |
| Range | (0; 57) | (3; 59) | (0; 59) |
| IQ range | (4.0; 16.0) | (10.0; 24.0) | (5.0; 19.5) |

TABLE 30-continued

Summary of the Observed Value and Change from Baseline in Tender Joint Count by Visit Through Week 48 for Subjects Randomized to Guselkumab; Full Analysis Set 1 (CNTO1959PSA3003)

| | Guselkumab 100 mg q8w No Early Escape at Week 16 | Guselkumab 100 mg q8w Early Escape at Week 16 | Total |
|---|---|---|---|
| Change from baseline | | | |
| N | 149 | 39 | 188 |
| Mean (SD) | −7.6 (8.88) | −3.0 (11.51) | −6.7 (9.63) |
| Median | −6.0 | 0.0 | −5.0 |
| Range | (−46; 20) | (−44; 28) | (−46; 28) |
| IQ range | (−11.0; −2.0) | (−9.0; 1.0) | (−11.0; −0.5) |
| Week 12 | | | |
| N | 146 | 39 | 185 |
| Mean (SD) | 11.1 (11.52) | 22.8 (15.89) | 13.5 (13.42) |
| Median | 8.0 | 19.0 | 10.0 |
| Range | (0; 62) | (3; 66) | (0; 66) |
| IQ range | (3.0; 15.0) | (11.0; 28.0) | (4.0; 18.0) |
| Change from baseline | | | |
| N | 146 | 39 | 185 |
| Mean (SD) | −9.2 (9.33) | −0.1 (11.28) | −7.3 (10.43) |
| Median | −7.5 | 0.0 | −6.0 |
| Range | (−48; 17) | (−42; 30) | (−48; 30) |
| IQ range | (−14.0; −3.0) | (−6.0; 5.0) | (−12.0; −2.0) |
| Week 16 | | | |
| N | 146 | 39 | 185 |
| Mean (SD) | 10.5 (11.03) | 25.7 (16.23) | 13.7 (13.73) |
| Median | 7.5 | 21.0 | 9.0 |
| Range | (0; 63) | (4; 68) | (0; 68) |
| IQ range | (3.0; 14.4) | (14.0; 36.0) | (4.0; 19.0) |
| Change from baseline | | | |
| N | 146 | 39 | 185 |
| Mean (SD) | −9.7 (9.41) | 2.7 (13.66) | −7.1 (11.59) |
| Median | −9.0 | 2.0 | −7.0 |
| Range | (−53; 12) | (−31; 31) | (−53; 31) |
| IQ range | (−14.0; −3.0) | (−1.0; 11.0) | (−13.0; −1.0) |
| Week 20 | | | |
| N | 144 | 39 | 183 |
| Mean (SD) | 10.0 (11.51) | 18.9 (16.48) | 11.9 (13.20) |
| Median | 7.0 | 15.0 | 8.0 |
| Range | (0; 66) | (0; 68) | (0; 68) |
| IQ range | (3.0; 12.5) | (7.0; 27.0) | (3.0; 16.0) |

TABLE 30-continued

Summary of the Observed Value and Change from Baseline in Tender
Joint Count by Visit Through Week 48 for Subjects Randomized
to Guselkumab; Full Analysis Set 1 (CNTO1959PSA3003)

| | Guselkumab 100 mg q8w No Early Escape at Week 16 | Guselkumab 100 mg q8w Early Escape at Week 16 | Total |
|---|---|---|---|
| Change from baseline | | | |
| N | 144 | 39 | 183 |
| Mean (SD) | −10.3 (9.54) | −4.0 (13.97) | −9.0 (10.91) |
| Median | −9.0 | −2.9 | −7.0 |
| Range | (−45; 14) | (−43; 38) | (−45; 38) |
| IQ range | (−16.0; −4.0) | (−10.0; 1.0) | (−15.0; −3.0) |
| Week 24 | | | |
| N | 146 | 38 | 184 |
| Mean (SD) | 9.1 (10.50) | 17.0 (14.41) | 10.7 (11.82) |
| Median | 6.0 | 12.0 | 7.0 |
| Range | (0; 67) | (2; 57) | (0; 67) |
| IQ range | (2.0; 11.0) | (7.0; 21.0) | (3.0; 15.0) |
| Change from baseline | | | |
| N | 146 | 38 | 184 |
| Mean (SD) | −11.1 (10.02) | −6.3 (13.64) | −10.1 (11.00) |
| Median | −9.0 | −6.5 | −9.0 |
| Range | (−49; 12) | (−43; 41) | (−49; 41) |
| IQ range | (−16.0; −4.0) | (−12.0; 1.0) | (−16.0; −3.4) |
| Week 28 | | | |
| N | 137 | 35 | 172 |
| Mean (SD) | 8.4 (10.02) | 13.5 (13.25) | 9.4 (10.92) |
| Median | 4.0 | 10.0 | 6.0 |
| Range | (0; 54) | (0; 64) | (0; 64) |
| IQ range | (2.0; 11.0) | (5.0; 17.0) | (2.0; 13.0) |
| Change from baseline | | | |
| N | 137 | 35 | 172 |
| Mean (SD) | −11.7 (9.78) | −10.5 (12.37) | −11.5 (10.33) |
| Median | −10.0 | −10.0 | −10.0 |
| Range | (−49; 18) | (−43; 28) | (−49; 28) |
| IQ range | (−17.0; −5.0) | (−18.0; −4.0) | (−17.0; −5.0) |
| Week 36 | | | |
| N | 130 | 34 | 164 |
| Mean (SD) | 7.3 (10.71) | 14.1 (14.46) | 8.7 (11.86) |
| Median | 4.0 | 10.0 | 5.0 |
| Range | (0; 68) | (0; 64) | (0; 68) |
| IQ range | (1.0; 9.0) | (5.2; 17.0) | (2.0; 10.0) |
| Change from baseline | | | |
| N | 130 | 34 | 164 |
| Mean (SD) | −12.3 (10.02) | −10.4 (11.09) | −11.9 (10.25) |
| Median | −11.0 | −9.0 | −11.0 |
| Range | (−51; 40) | (−43; 19) | (−51; 40) |
| IQ range | (−17.0; −6.0) | (−16.0; −6.0) | (−16.5; −6.0) |
| Week 44 | | | |
| N | 130 | 33 | 163 |
| Mean (SD) | 6.5 (9.60) | 11.5 (13.83) | 7.5 (10.74) |
| Median | 3.0 | 8.0 | 3.0 |
| Range | (0; 66) | (0; 63) | (0; 66) |
| IQ range | (1.0; 9.0) | (3.0; 13.0) | (1.0; 10.0) |
| Change from baseline | | | |
| N | 130 | 33 | 163 |
| Mean (SD) | −13.3 (9.62) | −13.3 (11.60) | −13.3 (10.01) |
| Median | −13.0 | −13.0 | −13.0 |
| Range | (−49; 22) | (−44; 3) | (−49; 22) |
| IQ range | (−18.0; −8.0) | (−18.0; −6.0) | (−18.0; −7.0) |
| Week 48 | | | |
| N | 131 | 36 | 167 |
| Mean (SD) | 7.2 (10.96) | 12.2 (15.17) | 8.3 (12.11) |
| Median | 3.0 | 6.0 | 4.0 |
| Range | (0; 58) | (0; 68) | (0; 68) |
| IQ range | (1.0; 8.0) | (3.5; 14.5) | (1.0; 10.0) |

TABLE 30-continued

Summary of the Observed Value and Change from Baseline in Tender
Joint Count by Visit Through Week 48 for Subjects Randomized
to Guselkumab; Full Analysis Set 1 (CNTO1959PSA3003)

| | Guselkumab 100 mg q8w No Early Escape at Week 16 | Guselkumab 100 mg q8w Early Escape at Week 16 | Total |
|---|---|---|---|
| Change from baseline | | | |
| N | 131 | 36 | 167 |
| Mean (SD) | −13.2 (10.42) | −12.0 (13.33) | −12.9 (11.08) |
| Median | −13.0 | −13.0 | −13.0 |
| Range | (−49; 39) | (−45; 20) | (−49; 39) |
| IQ range | (−18.0; −7.0) | (−19.0; −3.0) | (−18.0; −7.0) |

Key: IQ = inter-quartile.
[a] Tender joint count is the total number of tender joints among the 68 joints evaluated for tenderness.

Swollen Joint Counts

As shown in Table 31 below, for GUS randomized subjects, at baseline, the average number of swollen joints was 10.2 with an average improvement of −6.7 at Week 24 and −8.5 at Week 48. Subjects who were routed to Week 16 EE, compared to those without EE, had on average more swollen joints at baseline: 12.4 compared to 9.7. The average improvements at Week 24 were −6.0 and −6.9, and, at Week 48, −9.8 and −8.2, respectively.

TABLE 31

Summary of the Observed Value and Change from Baseline in Swollen
Joint Count by Visit Through Week 48 for Subjects Randomized
to Guselkumab; Full Analysis Set 1 (CNTO1959PSA3003)

| | Guselkumab 100 mg q8w No Early Escape at Week 16 | Guselkumab 100 mg q8w Early Escape at Week 16 | Total |
|---|---|---|---|
| Analysis set: Full Analysis Set 1 | 150 | 39 | 189 |
| Week 0 | | | |
| N | 150 | 39 | 189 |
| Mean (SD) | 9.7 (6.23) | 12.4 (8.25) | 10.2 (6.76) |
| Median | 8.0 | 10.0 | 8.0 |
| Range | (3; 39) | (3; 38) | (3; 39) |
| IQ range | (6.0; 11.0) | (6.0; 17.0) | (6.0; 13.0) |
| Week 4 | | | |
| N | 150 | 38 | 188 |
| Mean (SD) | 6.7 (6.44) | 8.2 (6.93) | 7.0 (6.55) |
| Median | 5.0 | 6.5 | 5.0 |
| Range | (0; 40) | (0; 35) | (0; 40) |
| IQ range | (2.0; 9.0) | (3.0; 12.0) | (3.0; 9.0) |
| Change from baseline | | | |
| N | 150 | 38 | 188 |
| Mean (SD) | −3.0 (3.90) | −3.8 (4.86) | −3.2 (4.11) |
| Median | −3.0 | −2.0 | −2.5 |
| Range | (−19; 9) | (−20; 3) | (−20; 9) |
| IQ range | (−5.0; 0.0) | (−6.0; −1.0) | (−5.0; −1.0) |
| Week 8 | | | |
| N | 149 | 39 | 188 |
| Mean (SD) | 4.5 (5.87) | 8.6 (8.17) | 5.4 (6.61) |
| Median | 2.0 | 6.0 | 3.0 |
| Range | (0; 33) | (0; 36) | (0; 36) |
| IQ range | (1.0; 6.0) | (2.0; 14.0) | (1.0; 6.5) |

TABLE 31-continued

Summary of the Observed Value and Change from Baseline in Swollen
Joint Count by Visit Through Week 48 for Subjects Randomized
to Guselkumab; Full Analysis Set 1 (CNTO1959PSA3003)

| | Guselkumab 100 mg q8w No Early Escape at Week 16 | Guselkumab 100 mg q8w Early Escape at Week 16 | Total |
|---|---|---|---|
| Change from baseline | | | |
| N | 149 | 39 | 188 |
| Mean (SD) | −5.1 (4.40) | −3.7 (8.15) | −4.8 (5.40) |
| Median | −5.0 | −2.0 | −4.0 |
| Range | (−20; 11) | (−36; 12) | (−36; 12) |
| IQ range | (−7.0; −3.0) | (−5.0; 0.0) | (−7.0; −2.0) |
| Week 12 | | | |
| N | 146 | 39 | 185 |
| Mean (SD) | 3.5 (4.67) | 8.9 (7.86) | 4.6 (5.91) |
| Median | 2.0 | 6.0 | 3.0 |
| Range | (0; 26) | (0; 42) | (0; 42) |
| IQ range | (0.0; 5.0) | (4.0; 14.0) | (0.0; 6.0) |
| Change from baseline | | | |
| N | 146 | 39 | 185 |
| Mean (SD) | −6.1 (4.46) | −3.4 (8.60) | −5.5 (5.67) |
| Median | −5.0 | −1.0 | −5.0 |
| Range | (−22; 2) | (−32; 18) | (−32; 18) |
| IQ range | (−8.0; −3.0) | (−4.0; 1.0) | (−7.0; −2.0) |
| Week 16 | | | |
| N | 146 | 39 | 185 |
| Mean (SD) | 3.3 (4.44) | 10.5 (7.10) | 4.8 (5.88) |
| Median | 2.0 | 9.1 | 3.0 |
| Range | (0; 21) | (0; 29) | (0; 29) |
| IQ range | (0.0; 4.0) | (4.0; 17.0) | (0.0; 7.0) |
| Change from baseline | | | |
| N | 146 | 39 | 185 |
| Mean (SD) | −6.3 (4.92) | −1.9 (10.17) | −5.4 (6.61) |
| Median | −5.0 | 1.0 | −5.0 |
| Range | (−29; 5) | (−35; 16) | (−35; 16) |
| IQ range | (−8.3; −3.0) | (−2.0; 4.0) | (−8.0; −2.0) |
| Week 20 | | | |
| N | 144 | 39 | 183 |
| Mean (SD) | 3.3 (5.78) | 7.3 (6.18) | 4.2 (6.07) |
| Median | 1.0 | 7.0 | 2.0 |
| Range | (0; 48) | (0; 23) | (0; 48) |
| IQ range | (0.0; 4.0) | (1.0; 10.0) | (0.0; 6.0) |
| Change from baseline | | | |
| N | 144 | 39 | 183 |
| Mean (SD) | −6.3 (5.69) | −5.1 (9.97) | −6.1 (6.81) |
| Median | −6.0 | −3.0 | −5.0 |
| Range | (−26; 24) | (−38; 14) | (−38; 24) |
| IQ range | (−9.0; −4.0) | (−8.0; 1.0) | (−9.0; −3.0) |
| Week 24 | | | |
| N | 146 | 38 | 184 |
| Mean (SD) | 2.6 (3.89) | 6.5 (6.16) | 3.4 (4.70) |
| Median | 1.0 | 5.0 | 2.0 |
| Range | (0; 20) | (0; 25) | (0; 25) |
| IQ range | (0.0; 4.0) | (2.0; 9.0) | (0.0; 5.0) |
| Change from baseline | | | |
| N | 146 | 38 | 184 |
| Mean (SD) | −6.9 (5.47) | −6.0 (8.84) | −6.7 (6.30) |
| Median | −6.0 | −4.0 | −6.0 |
| Range | (−33; 5) | (−36; 9) | (−36; 9) |
| IQ range | (−9.0; −4.0) | (−11.0; 0.0) | (−9.0; −3.0) |
| Week 28 | | | |
| N | 137 | 35 | 172 |
| Mean (SD) | 2.5 (3.96) | 4.7 (5.63) | 3.0 (4.42) |
| Median | 1.0 | 3.0 | 1.0 |
| Range | (0; 22) | (0; 20) | (0; 22) |
| IQ range | (0.0; 3.0) | (0.0; 8.0) | (0.0; 4.0) |

TABLE 31-continued

Summary of the Observed Value and Change from Baseline in Swollen
Joint Count by Visit Through Week 48 for Subjects Randomized
to Guselkumab; Full Analysis Set 1 (CNTO1959PSA3003)

| | Guselkumab 100 mg q8w No Early Escape at Week 16 | Guselkumab 100 mg q8w Early Escape at Week 16 | Total |
|---|---|---|---|
| Change from baseline | | | |
| N | 137 | 35 | 172 |
| Mean (SD) | −7.1 (5.01) | −7.9 (9.10) | −7.3 (6.05) |
| Median | −6.0 | −7.0 | −6.0 |
| Range | (−25; 6) | (−37; 9) | (−37; 9) |
| IQ range | (−9.0; −4.0) | (−12.0; −4.0) | (−9.5; −4.0) |
| Week 36 | | | |
| N | 130 | 34 | 164 |
| Mean (SD) | 1.9 (3.50) | 4.3 (5.05) | 2.4 (3.98) |
| Median | 0.0 | 2.0 | 0.0 |
| Range | (0; 20) | (0; 20) | (0; 20) |
| IQ range | (0.0; 2.0) | (0.0; 7.0) | (0.0; 3.5) |
| Change from baseline | | | |
| N | 130 | 34 | 164 |
| Mean (SD) | −7.8 (5.59) | −8.5 (8.08) | −8.0 (6.17) |
| Median | −7.0 | −7.5 | −7.0 |
| Range | (−33; 3) | (−37; 5) | (−37; 5) |
| IQ range | (−10.0; −5.0) | (−12.0; −4.0) | (−10.0; −5.0) |
| Week 44 | | | |
| N | 130 | 33 | 163 |
| Mean (SD) | 1.7 (3.26) | 2.8 (3.97) | 1.9 (3.43) |
| Median | 0.0 | 1.0 | 0.0 |
| Range | (0; 18) | (0; 16) | (0; 18) |
| IQ range | (0.0; 2.0) | (0.0; 4.0) | (0.0; 2.0) |
| Change from baseline | | | |
| N | 130 | 33 | 163 |
| Mean (SD) | −7.9 (5.86) | −10.0 (8.82) | −8.3 (6.59) |
| Median | −7.0 | −7.0 | −7.0 |
| Range | (−35; 4) | (−38; 4) | (−38; 4) |
| IQ range | (−10.0; −5.0) | (−13.0; −5.0) | (−11.0; −5.0) |
| Week 48 | | | |
| N | 131 | 36 | 167 |
| Mean (SD) | 1.7 (3.07) | 3.1 (4.05) | 2.0 (3.34) |
| Median | 0.0 | 1.5 | 0.0 |
| Range | (0; 13) | (0; 15) | (0; 15) |
| IQ range | (0.0; 2.0) | (0.0; 4.5) | (0.0; 3.0) |
| Change from baseline | | | |
| N | 131 | 36 | 167 |
| Mean (SD) | −8.2 (5.70) | −9.8 (9.06) | −8.5 (6.57) |
| Median | −7.0 | −7.5 | −7.0 |
| Range | (−35; 3) | (−38; 8) | (−38; 8) |
| IQ range | (−10.0; −5.0) | (−13.5; −5.0) | (−11.0; −5.0) |

Key: IQ = inter-quartile.

[a] Swollen joint count is the total number of swollen joints among the 66 joints evaluated for swelling.

MDA Status

As shown in Table 32 below, of GUS randomized subjects, the overall observed proportion of subjects achieving MDA, was 17.4% at Week 24 and 32.5% at Week 48. Of subjects who were routed to Week 16 EE, 5.3% achieved MDA at Week 24 and 22.2% at Week 48, and of those without EE, this was 20.5% at Week 24 and 35.3% at Week 48.

TABLE 32

Number of Subjects Achieving MDA by Visit Through Week 48 for Subjects
Randomized to Guselkumab; Full Analysis Set 1 (CNTO1959PSA3003)

| | Guselkumab 100 mg q8w No Early Escape at Week 16 | Guselkumab 100 mg q8w Early Escape at Week 16 | Total |
|---|---|---|---|
| Analysis set: Full Analysis Set 1 | 150 | 39 | 189 |
| Week 4 | | | |
| Subjects evaluable for MDA Response[a] | 147 | 39 | 186 |
| Subjects with MDA Response | 2 (1.4%) | 0 | 2 (1.1%) |
| Week 8 | | | |
| Subjects evaluable for MDA Response[a] | 145 | 39 | 184 |
| Subjects with MDA Response | 3 (2.1%) | 0 | 3 (1.6%) |
| Week 12 | | | |
| Subjects evaluable for MDA Response[a] | 129 | 38 | 167 |
| Subjects with MDA Response | 5 (3.9%) | 0 | 5 (3.0%) |
| Week 16 | | | |
| Subjects evaluable for MDA Response[a] | 146 | 39 | 185 |
| Subjects with MDA Response | 21 (14.4%) | 1 (2.6%) | 22 (11.9%) |
| Week 20 | | | |
| Subjects evaluable for MDA Response[a] | 124 | 37 | 161 |
| Subjects with MDA Response | 5 (4.0%) | 1 (2.7%) | 6 (3.7%) |
| Week 24 | | | |
| Subjects evaluable for MDA Response[a] | 146 | 38 | 184 |
| Subjects with MDA Response | 30 (20.5%) | 2 (5.3%) | 32 (17.4%) |
| Week 28 | | | |
| Subjects evaluable for MDA Response[a] | 126 | 35 | 161 |
| Subjects with MDA Response | 20 (15.9%) | 3 (8.6%) | 23 (14.3%) |
| Week 36 | | | |
| Subjects evaluable for MDA Response[a] | 117 | 33 | 150 |
| Subjects with MDA Response | 25 (21.4%) | 1 (3.0%) | 26 (17.3%) |
| Week 44 | | | |
| Subjects evaluable for MDA Response[a] | 122 | 32 | 154 |
| Subjects with MDA Response | 34 (27.9%) | 5 (15.6%) | 39 (25.3%) |
| Week 48 | | | |
| Subjects evaluable for MDA Response[a] | 133 | 36 | 169 |
| Subjects with MDA Response | 47 (35.3%) | 8 (22.2%) | 55 (32.5%) |

Key: CRP = C-reactive protein, DMARD = Disease-Modifying Antirheuniatic Drug, MDA = minimal disease activity, TNF = tumor necrosis factor

[a]MDA is achieved if at least 5 of the 7 criteria are met (tender joint count ≤1, swollen joint count ≤1, psoriasis activity and severity index ≤1, patient's assessment of pain ≤15, patient's global assessment of disease activity ≤20, HAQ-DI score ≤0.5, Tender entheseal points ≤1).

Resolution of Enthesitis

Resolution of enthesitis was assessed in subjects with enthesitis at baseline (LEI>0), 67% of both the GUS and PBO populations. As shown in Table 33 below, of GUS randomized subjects, the overall observed proportion of subjects achieving resolution of enthesitis, was 52.0% at Week 24 and 67.50% at Week 48. Of subjects who were routed to Week 16 EE, 61.5% achieved resolution of enthesitis at Week 48, and of those without EE, this was 69.3%.

TABLE 33

Number of Subjects Achieving Resolution of Enthesitis (LEI) by Visit through
Week 48 Among the Subjects with Enthesitis (LEI) at baseline for Subjects
Randomized to Guselkumab; Full Analysis Set 1 (CNTO1959PSA3003)

| | Guselkumab 100 mg q8w No Early Escape at Week 16 | Guselkumab 100 mg q8w Early Escape at Week 16 | Total |
|---|---|---|---|
| Analysis set: Full Analysis Set 1 Among the Subjects with Enthesitis (LEI) score >0 at Baseline | 99 | 27 | 126 |
| Week 4 | | | |
| Subjects evaluable for Resolution of Enthesitis (LEI)[a] | 99 | 26 | 125 |
| Subjects with Resolution of Enthesitis (LEI) | 21 (21.2%) | 6 (23.1%) | 27 (21.6%) |
| Week 8 | | | |
| Subjects evaluable for Resolution of Enthesitis (LEI)[a] | 98 | 27 | 125 |
| Subjects with Resolution of Enthesitis (LEI) | 39 (39.8%) | 5 (18.5%) | 44 (35.2%) |
| Week 16 | | | |
| Subjects evaluable for Resolution of Enthesitis (LEI)[a] | 95 | 27 | 122 |
| Subjects with Resolution of Enthesitis (LEI) | 52 (54.7%) | 9 (33.3%) | 61 (50.0%) |
| Week 24 | | | |
| Subjects evaluable for Resolution of Enthesitis (LEI)[a] | 96 | 27 | 123 |
| Subjects with Resolution of Enthesitis (LEI) | 52 (54.2%) | 12 (44.4%) | 64 (52.0%) |
| Week 28 | | | |
| Subjects evaluable for Resolution of Enthesitis (LEI)[a] | 91 | 25 | 116 |
| Subjects with Resolution of Enthesitis (LEI) | 51 (56.0%) | 13 (52.0%) | 64 (55.2%) |
| Week 36 | | | |
| Subjects evaluable for Resolution of Enthesitis (LEI)[a] | 84 | 24 | 108 |
| Subjects with Resolution of Enthesitis (LEI) | 57 (67.9%) | 9 (37.5%) | 66 (61.1%) |
| Week 44 | | | |
| Subjects evaluable for Resolution of Enthesitis (LEI)[a] | 85 | 24 | 109 |
| Subjects with Resolution of Enthesitis (LEI) | 59 (69.4%) | 14 (58.3%) | 73 (67.0%) |
| Week 48 | | | |
| Subjects evaluable for Resolution of Enthesitis (LEI)[a] | 88 | 26 | 114 |
| Subjects with Resolution of Enthesitis (LEI) | 61 (69.3%) | 16 (61.5%) | 77 (67.5%) |

Key: CRP = C-reactive protein, DMARD = Disease-Modifying Antirheumatic Drug, LEI = Leeds Enthesitis Index, TNF = tumor necrosis factor

[a]Enthesitis score is a total score of 6 evaluated sites (left and right: lateral epicondyle humerus, medial femoral condyle, achilles tendon insertion) with a range from 0 to 6. A negative change from baseline indicates improvement. Enthesitis resolution is established when a subject with at least one tender entheses at baseline has no tender entheses among the 6 sites included in the LEI.

FACIT-Fatigue Improvement

As shown in Table 34, of GUS randomized subjects, the overall observed proportion of subjects with ≥4-point improvement from baseline in FACIT-Fatigue score, was 58.5% at Week 24 and 69.0% at Week 48. Of GUS subjects who were routed to Week 16 EE, 60.0% achieved ≥4-point improvement in FACIT-Fatigue at Week 48, compared to 71.3% for those without EE.

TABLE 34

Number of Subjects Achieving ≥4 Improvement from Baseline in FACIT-Fatigue by Visit through Week 48 for Subjects Randomized to Guselkumab; Full Analysis Set 1 (CNTO1959PSA3003)

| | Guselkumab 100 mg q8w No Early Escape at Week 16 | Guselkumab 100 mg q8w Early Escape at Week 16 | Total |
|---|---|---|---|
| Analysis set: Full Analysis Set 1 | 150 | 39 | 189 |
| Week 8 | | | |
| Subjects evaluable for FACIT | 149 | 38 | 187 |
| Subjects with ≥4 Improvement in FACIT-Fatigue score | 71 (47.7%) | 18 (47.4%) | 89 (47.6%) |
| Week 16 | | | |
| Subjects evaluable for FACIT | 145 | 38 | 183 |
| Subjects with ≥4 Improvement in FACIT-Fatigue score | 83 (57.2%) | 21 (55.3%) | 104 (56.8%) |
| Week 24 | | | |
| Subjects evaluable for FACIT | 146 | 37 | 183 |
| Subjects with ≥4 Improvement in FACIT-Fatigue score | 83 (56.8%) | 24 (64.9%) | 107 (58.5%) |
| Week 36 | | | |
| Subjects evaluable for FACIT | 134 | 34 | 168 |
| Subjects with ≥4 Improvement in FACIT-Fatigue score | 91 (67.9%) | 21 (61.8%) | 112 (66.7%) |
| Week 48 | | | |
| Subjects evaluable for FACIT | 136 | 35 | 171 |
| Subjects with ≥4 Improvement in FACIT-Fatigue score | 97 (71.3%) | 21 (60.0%) | 118 (69.0%) |

Key: CRP = C-reactive protein, DMARD = Disease-Modifying Antirheumatic Drug, FACIT = Functional Assessment of Chronic Illness Therapy, TNF = tumor necrosis factor
[a] The FACIT-Fatigue score is calculated based on the FACIT-Fatigue questionnaire that comprises of 13 questions, with each question graded on a 5-point scale (0-4). The FACIT-Fatigue scores can range from 0 to 52 with higher scores indicating less fatigue.

Safety Through Week 56:

Week 56 safety was assessed amongst all randomized and treated participants who received at least 1 dose of guselkumab (partial or complete) according to the actual treatment received during the study, irrespective of the treatment assigned at randomization. This is also referred to as the safety analysis set. Key safety events are summarized in Table 35 below.

Through Week 56, overall, 49.8% of subjects, reported at least one adverse event. For patients who crossed over to GUS at Week 16 or Week 24, this was 46.7% and 44.4% respectively. For patients randomized to GUS, more patients reported adverse events during the $1^{st}$ 24 weeks (42.3%) than during follow-up after Week 24 (30.5%). Of GUS randomized subjects, 3.7% had a serious adverse event (SAE) through Week 24 and 2.9% during follow-up after Week 24. Of PBO-randomized patients who crossed over to GUS at Week 16, as well as of those who crossed over at Week 24, 4.4% reported an SAE. Overall, 2.5% of subjects reported adverse events resulting in discontinuation of guselkumab administration, mostly in the first 24 weeks of the study (2.1% vs 1.7%).

Through Week 56, 21.9% of GUS-treated subjects had at least one infection identified by the investigators. For GUS-randomized subjects, infections were reported more often during the $1^{st}$ 24 weeks (21.2%) than %) than during follow-up after Week 24 up to Week 56 (9.2%). Of subjects randomized to PBO, 15.6% reported infections after crossover at Week 16, 13.3% after crossover at Week 24. Two subjects (0.7%) reported one or more serious infections, one GUS- and one PBO-randomized subject, both reported a pneumonia.

Through Week 56, overall, 1.8% (n=5) of GUS-treated subjects had at least one injection site reaction.

Through Week 56, malignancy was reported in 1 (0.5%) subject. This malignancy, reported in the GUS group in study Week 19, was a prostate cancer. Given the subject's history of chronic prostatitis, and the relatively short interval between study treatment initiation and diagnosis of cancer, causality was assessed as not related to the study treatment.

No deaths, opportunistic infections, tuberculosis, suicidal ideation or behavior and anaphylactic or serum sickness reactions were reported through Week 56.

Through Week 56, the most common treatment emergent adverse event System Organ Class (SOC) observed was Infections and infestations (20.8%), of which, the most common AEs reported were nasopharyngitis (5.7%) and upper respiratory tract infection (3.6%).

Through Week 56, elevation in alanine aminotransferase (ALT) serum levels were reported as AEs in 11 subjects (3.9%), of which one reached the designation of an SAE. Elevated aspartate aminotransferase (AST) serum levels were reported as AEs in 6 subjects (2.2%). For one subject (0.4%), the elevated hepatic enzyme was reported as an SAE. Further details to these SAE will be provided in the CSR.

Through Week 56, decreases in neutrophils and white blood cell counts (reported as adverse events) were observed in 1.1% and 1.1%, respectively. None of these events reached the threshold of a SAE.

TABLE 35

Overall Summary of Treatment-emergent Adverse Events through Week 56; Safety Analysis Set 2 (CNTO1959PSA3003)

| | On Guselkumab | | | | |
|---|---|---|---|---|---|
| | Placebo crossover to Guselkumab at Week 16 | Placebo crossover to Guselkumab at Week 24 | Randomized to Guselkumab Week 0 to Week 24 | Randomized to Guselkumab Week 24 to Week 56 | Guselkumab Combined |
| Analysis set: Safety Analysis Set 2 | 45 | 45 | 189 | 174 | 279 |
| Subjects with 1 or more adverse events | 21 (46.7%) | 20 (44.4%) | 80 (42.3%) | 53 (30.5%) | 139 (49.8%) |
| Subjects with 1 or more serious adverse events | 2 (4.4%) | 2 (4.4%) | 7 (3.7%) | 5 (2.9%) | 15 (5.4%) |

TABLE 35-continued

Overall Summary of Treatment-emergent Adverse Events through
Week 56; Safety Analysis Set 2 (CNTO1959PSA3003)

| | On Guselkumab | | | | |
| | Placebo crossover to Guselkumab at Week 16 | Placebo crossover to Guselkumab at Week 24 | Randomized to Guselkumab Week 0 to Week 24 | Randomized to Guselkumab Week 24 to Week 56 | Guselkumab Combined |
|---|---|---|---|---|---|
| Subjects with 1 or more adverse events leading to discontinuation of study agent | 0 | 0 | 4 (2.1%) | 3 (1.7%) | 7 (2.5%) |
| Subjects with 1 or more adverse events with severe intensity | 0 | 0 | 5 (2.6%) | 2 (1.1%) | 7 (2.5%) |
| Subjects with 1 or more infections | 7 (15.6%) | 6 (13.3%) | 40 (21.2%) | 16 (9.2%) | 61 (21.9%) |
| Subjects with 1 or more serious infections | 0 | 1 (2.2%) | 1 (0.5%) | 0 | 2 (0.7%) |
| Subjects with 1 or more opportunistic infections | 0 | 0 | 0 | 0 | 0 |
| Subjects with 1 or more injection site reactions | 0 | 1 (2.2%) | 4 (2.1%) | 0 | 5 (1.8%) |
| Subjects with 1 or more events of suicidal ideation or behavior | 0 | 0 | 0 | 0 | 0 |
| Subjects with 1 or more events of malignancy | 0 | 0 | 1 (0.5%) | 0 | 1 (0.4%) |
| Subjects with 1 or more events of tuberculosis | 0 | 0 | 0 | 0 | 0 |
| Subjects with 1 or more events of anaphylactic reactions or serum sickness | 0 | 0 | 0 | 0 | 0 |
| Subjects with 1 or more events leading to death | 0 | 0 | 0 | 0 | 0 |

As shown in Table 36 below, results of additional secondary endpoints assessed at week 24 also showed a numerical benefit of guselkumab over placebo for achievement of ACR70, MDA, and VLDA, as well as for achieving PASI75 and PASI90 in patients with ≥3% BSA with psoriasis and IGA ≥2 at baseline. These analyses were performed using nonresponder imputation. Among participants with enthesitis or dactylitis at baseline, numerically higher proportions of guselkumab than placebo patients had enthesitis or dactylitis resolution, respectively, at week 24. The proportions of patients achieving a ≥4-point improvement in FACIT-F, reflecting clinically meaningful improvement, were higher in the guselkumab group than in the placebo group. The LS mean changes from baseline in SF-36 MCS scores were also numerically greater in the guselkumab group After week 24, response rates and mean improvements for secondary endpoints were sustained or numerically improved through week 48 in patients who were randomized to guselkumab at baseline. Among patients who crossed over from placebo to guselkumab at week 24, response rates and mean changes in the secondary endpoints increased at week 48.

Maintenance of response was evaluated for guselkumab-randomized patients achieving an ACR20, ACR50, or ACR70 response at week 24; of these patients, 83.3% (70/84), 81.1% (30/37), and 86.7% (13/15), respectively, maintained response at week 48.

TABLE 36

| | Week 24 | | Week 48 | |
|---|---|---|---|---|
| | Guselkumab 100 mg Q8W | Placebo | Guselkumab 100 mg Q8W | Placebo→ Guselkumab 100 mg Q8W |
| Treated participants according to randomized group, N | 189 | 96 | 189 | 51 |
| ACR70 response | 15 (7.9%) | 1 (1.0%) | 45 (23.8%) | 9 (17.6%) |
| % difference (95% CI)[b] | 6.8 (2.6, 11.1) | | | |
| Unadjusted p value vs. placebo[c] | 0.018 | | | |
| Enthesitis resolution (LEI score = 0)[d] | 50/126 (39.7%) | 12/64 (18.8%) | 70/126 (55.6%) | 14/35 (40.0%) |
| % difference (95% CI)[b] | 21.6 (8.8, 34.4) | | | |
| Unadjusted p value vs. placebo[c] | 0.003 | | | |
| Dactylitis resolution (DSS = 0)[e] | 30/67 (44.8%) | 9/36 (25.0%) | 45/67 (67.2%) | 11/13 (84.6%) |
| % difference (95% CI)[b] | 19.9 (2.7, 37.1) | | | |
| Unadjusted p value vs. placebo[c] | 0.040 | | | |
| IGA response (IGA 0/1 and ≥2-grade improvement from baseline)[f] | 64/133 (48.1%) | 5/53 (9.4%) | 87/133 (65.4%) | 14/23 (60.9%) |
| % difference (95% CI)[b] | 38.8 (27.3, 50.4) | | | |
| Unadjusted p value vs. placebo[c] | <0.001 | | | |
| PASI75 response[f] | 79/133 (59.4%) | 5/53 (9.4%) | 99/133 (74.4%) | 19/23 (82.6%) |
| % difference (95% CI)[b] | 49.6 (38.3, 60.9) | | | |
| Unadjusted p value vs. placebo[c] | <0.001 | | | |
| PASI90 response[f] | 68/133 (51.1%) | 4/53 (7.5%) | 89/133 (66.9%) | 14/23 (60.9%) |
| % difference (95% CI)[b] | 43.7 (32.7, 54.7) | | | |
| Unadjusted p value vs. placeboc | <0.001 | | | |
| SF-36 MCS score | | | | |
| LS mean change from baseline[g] | 2.10 (0.54, 3.65) | 0.36 (−1.52, 2.25) | — | — |
| LS mean difference (95% CI)[b] | 1.73 (−0.14, 3.61) | | — | — |
| Unadjusted p value vs. placebo[g] | 0.070 | | | |
| Mean change from baseline (SD)[h] | — | — | 3.05 (9.95) | 3.82 (8.91) |
| FACIT-F response (≥4-point improvement from baseline) | 81 (42.9%) | 20 (20.8%) | 55.6% | 51.0% |
| % difference (95% CI)[b] | 21.9 (11.2, 32.7) | | | |
| Unadjusted p value vs. placebo[c] | <0.001 | | | |
| MDA | 28 (14.8%) | 3 (3.1%) | 51 (27.0%) | 14 (27.5%) |
| % difference (95% CI)[b] | 11.7 (5.6, 17.7) | | | |
| Unadjusted p value vs. placebo[c] | 0.003 | | | |
| VLDA | 7 (3.7%) | 0 | 21 (11.1%) | 2 (3.9%) |
| % difference (95% CI)[b] | 3.7 (1.0, 6.4) | | | |
| Unadjusted p value vs. placebo[c] | 0.057 | | | |

Data shown are n (%) or n/N (%) unless stated otherwise

[a]Through week 24, patients who discontinued study agent/study participation for any reason, initiated or increased the dose of allowed csDMARDs/oral corticosteroids over baseline for PsA, initiated protocol-prohibited medications/therapies for PsA, or met EE criteria (including those incorrectly assigned to EE) were considered to be nonresponders or to have no improvement from baseline at subsequent timepoints. After week 24, patients who met the EE criteria (excluding those who were incorrectly assigned to EE) and patients who discontinued study agent/study participation for any reason were considered to be nonresponders or to have no improvement from baseline at subsequent timepoints; missing data were imputed as nonresponse or multiple imputation (assumed to be missing-at-random).

[b]CIs based on Wald statistic

[c]Unadjusted (nominal) p values based on the Cochran-Mantel-Haenszel test, stratified by baseline use of csDMARD (yes/no) and prior exposure to TNFi (1/2)

[d]In patients with LEI score ≥1 at baseline

[e]In patients with DSS score ≥1 at baseline

[f]In patients with ≥3% BSA psoriasis involvement and IGA ≥2 at baseline

[g]LSmeans and unadjusted (nominal) p values based on a mixed model for repeated measures under the missing-at-random assumption for missing data. LS means were determined only through week 24.

[h]Post-week 24, mean changes from baseline were determined using change of 0 for patients who discontinued or met the EE criteria prior to week 24 (excluding patients incorrectly assigned to EE) and multiple imputation (assumed to be missing-at-random) for missing data.

ACR, American College of Rheumatology;

BSA, body surface area;

CI, confidence interval;

csDMARD, conventional synthetic disease-modifying antirheumatic drug;

DSS, Dactylitis Severity Score;

EE, early escape;

FACIT-F, Functional Assessment of Chronic Illness Therapy-Fatigue;

IGA, Investigator's Global Assessment of psoriasis;

LEI, Leeds Enthesitis Index;

MDA, Minimal Disease Activity;

PASI, Psoriasis Area and Severity Index;

PsA, psoriatic arthritis;

Q8W, every 8 weeks;

SF-36 MCS, 36-item Short-Form Health Survey Mental Component Summary;

SD, standard deviation;

TNFi, tumor necrosis factor-inhibitor;

VLDA, Very Low Disease Activity

Discussion and Week 48/56 Conclusion(s)

Overall, the COSMOS trial, evaluating efficacy and safety of guselkumab (GUS) 100 mg at Weeks 0, 4 then q8w up to Week 44 and demonstrated in terms of efficacy: (i) superiority of GUS over PBO with respect to its primary endpoint of ACR20 response at Week 24, (ii) superiority of GUS over PBO with respect to all 4 key secondary endpoints at Week 24 (based on a predefined hierarchical testing procedure): HAQ-DI, ACR50 response, SF36-PCS, and PASI100, (iii) a benefit of GUS over PBO with regards to exploratory endpoints such as resolution of enthesitis and dactylitis, SF-36, FACIT-Fatigue etc., (iv) a high maintenance of response in joint outcomes (ACR20:91.2%; ACR50:94.6%; ACR70:81.3%) up to Week 48 of GUS therapy, and (v) a high rate of retention of patients in the study was observed (above 85% up Week 48).

Overall, GUS demonstrated robust efficacy on signs and symptoms of the joints and skin psoriasis, improved physical function and the physical component of health-related quality of life up to 48 weeks of therapy. GUS dosing regimen was safe and well-tolerated through Week 56 in this study. The safety profile of guselkumab through Week 56 in this population of psoriatic arthritis patient refractory to anti-TNF therapy is generally consistent with that demonstrated in the psoriasis or bionaive psoriatic arthritis indication. A trend towards incremental benefit over time was observed for all outcomes evaluated after Week 24. Given these trends are based on ' as observed' data, proper non-responder and multiple imputation techniques will be applied to these observations to confirm the findings. These and other exploratory analyses will be reported in the Clinical Study Report, including the effect of transitioning PBO patients to GUS.

Overall Rationale for the Study

Investigation of guselkumab in this Phase 3b PsA clinical study was supported by robust efficacy results and a favorable safety profile from Phase 3 studies in psoriasis, including the subset of patients with PsA, as well as a Phase 2a study and two Phase 3 studies with guselkumab in PsA.

Phase 3 studies of guselkumab in psoriasis include 2 large placebo- and active-comparator-controlled studies (CNTO1959PSO3001 [VOYAGE-1] and CNTO1959PSO3002 [VOYAGE-2]), which included participants with active PsA at baseline (18.6% and 18.0%, respectively). The studies consistently demonstrated that guselkumab is highly effective and that treatment leads to rapid, substantial, and clinically significant improvements in psoriasis in this population. Compared with the overall population, guselkumab was equally effective across all subpopulations, as defined by gender, baseline age, baseline weight, race, geographic region, presence or absence of PsA at baseline, and psoriasis treatment history. In both studies, guselkumab was statistically superior to placebo or adalimumab (p<0.001) for the coprimary and all major secondary endpoints.

The Phase 2a study for guselkumab in PsA, CNTO1959PSA2001, demonstrated significant improvement in symptoms, including joint symptoms, physical function, psoriasis, enthesitis, dactylitis, and quality of life in participants with active PsA and ≥3% body surface area (BSA) of psoriasis. The primary and all secondary endpoints were met in this study, with efficacy maintained through approximately 1 year of exposure among the participants in the guselkumab group. These data were confirmed in the 2 registrational Phase 3 studies (CNTO1959PSA3001 [DIS- COVER-1] and CNTO1959PSA3002 [DISCOVER-2]), validating guselkumab as an effective therapeutic intervention in PsA.

The Phase 3 studies (the DISCOVER program) mainly included biologic-naïve patients. The purpose of this study (CNTO1959PSA3003 [COSMOS]) was to further define the clinical efficacy (reduction of signs and symptoms of joint and psoriasis skin disease) and evaluate the safety of guselkumab in the treatment of patients with active PsA who previously had an inadequate response (i.e., refractory) or were intolerant to anti-TNFα therapy.

The present invention further comprises a pharmaceutical composition of an anti-IL-23 antibody for treatment of psoriatic arthritis in subjects having an inadequate response to anti-TNF therapy and packaging, wherein the antibody comprises: (i) a heavy chain variable region and a light chain variable region, the heavy chain variable region comprising: a complementarity determining region heavy chain 1 (CDRH1) amino acid sequence of SEQ ID NO:1; a CDRH2 amino acid sequence of SEQ ID NO:2; and a CDRH3 amino acid sequence of SEQ ID NO:3; and the light chain variable region comprising: a complementarity determining region light chain 1 (CDRL1) amino acid sequence of SEQ ID NO:4; a CDRL2 amino acid sequence of SEQ ID NO:5; and a CDRL3 amino acid sequence of SEQ ID NO:6; (ii) a heavy chain variable region of the amino acid sequence of SEQ ID NO:7 and a light chain variable region of the amino acid sequence of SEQ ID NO:8; or (iii) a heavy chain of the amino acid sequence of SEQ ID NO:9 and a light chain of the amino acid sequence of SEQ ID NO:10.

The invention can be described with reference to the following numbered embodiments:

1. Use of an anti-IL-23 antibody for the treatment of psoriatic arthritis in a subject in need thereof, wherein the subject showed an inadequate response to treatment with an anti-TNF therapy, wherein about 50 mg to about 150 mg the antibody is administered subcutaneously to the subject once every 4 weeks (q4w), and wherein the antibody comprises a heavy chain variable region and a light chain variable region, the heavy chain variable region comprising a complementarity determining region heavy chain 1 (CDRH1) amino acid sequence of SEQ ID NO: 1, a CDRH2 of SEQ ID NO: 2, and a CDRH3 of SEQ ID NO: 3; and the light chain variable region comprising a complementarity determining region light chain 1 (CDRL1) amino acid sequence of SEQ ID NO: 4, a CDRL2 of SEQ ID NO: 5, and a CDRL3 of SEQ ID NO: 6, and wherein the subject achieves at least a 20% improvement in the American College of Rheumatology core set disease index (ACR20) after the treatment.

2. The use of embodiment 1, wherein the antibody comprises the heavy chain variable region of the amino acid sequence of SEQ ID NO: 7, and the light chain variable region of the amino acid sequence of SEQ ID NO: 8.

3. The use of embodiment 1, wherein the antibody comprises the heavy chain amino acid sequence of SEQ ID NO: 9, and the light chain amino acid sequence of SEQ ID NO: 10.

4. The use of embodiment 1, wherein the antibody is administered at a dose of about 100 mg per administration.

5. The use of embodiment 1, wherein the ACR20 is achieved following a treatment period of about 24 weeks.

6. The use of embodiment 5, wherein the ACR20 is achieved or maintained following a treatment period of about 48 weeks.
7. The use of embodiment 1, wherein the anti-TNF therapy is an anti-TNFα antibody or TNFα non-antibody antagonist.
8. The use of embodiment 7, wherein the anti-TNFα antibody is adalimumab, golimumab, certolizumab pegol therapy, infliximab and/or biosimilars thereto and the TNFα non-antibody antagonist is etanercept and/or biosimilars thereto.
9. The use of embodiment 1, wherein, after the treatment, the subject further achieves an improvement in a disease activity determined by at least one criteria selected from the group consisting of a 50% improvement in the American College of Rheumatology core set disease index (ACR50), a 70% improvement in the American College of Rheumatology core set disease index (ACR70), Health Assessment Questionnaire Disability Index (HAQ-DI), Investigator's Global Assessment (IGA), Disease Activity Score 28 (DAS28) C-reactive protein (CRP), resolution of enthesitis, resolution of dactylitis, Leeds enthesitis index (LEI), dactylitis assessment score, Short Form Health survey (SF-36) in the mental and physical component summary (MCS and PCS), achievement of minimal disease activity (MDA), very low disease activity (VLDA), Bath Ankylosing Spondylitis Disease Activity Index (BASDAI), GRAppa Composite score (GRACE), Psoriatic ArthritiS Disease Activity Score (PASDAS), modified Composite Psoriatic Disease Activity Index (mCPDAI), Psoriatic Area and Severity Index (PAST), Dermatology Life Quality Index (DLQI), Functional Assessment of Chronic Illness Therapy (FACIT), and Patient-Reported Outcomes Measurement Information System-29 (PROMIS-29).
10. The use of embodiment 1, wherein the subject further achieves at least a 50% improvement in the American College of Rheumatology core set disease index (ACR50) after the treatment.
11. The use of embodiment 1, wherein the subject further achieves an improvement in the Health Assessment Questionnaire Disability Index (HAQ-DI) following a treatment period of at least about 24 weeks or about 48 weeks.
12. The use of embodiment 1, wherein the subject further achieves an improvement in Disease Activity Score 28 (DAS28) C-reactive protein (CRP) following a treatment period of at least about 24 weeks or about 48 weeks.
13. The use of embodiment 1, wherein the subject further achievs Investigator's Global Assessment (IGA) of 0 (clear) or 1 (minimal), or 2 or more grade reduction in the IGA, following a treatment period of at least about 24 weeks or at least about 48 weeks, wherein the subject has 3% or more body surface area (BSA) psoriatic involvement and an IGA score of 2 or more at the baseline before the treatment.
14. The use of embodiment 1, wherein the subject has had inadequate response to a standard therapy for the PsA, optionally, the subject is also administered the standard therapy during the treatment.
15. Use of an anti-IL-23 antibody for the treatment of psoriatic arthritis in a subject in need thereof, wherein the subject showed an inadequate response to treatment with an anti-TNF therapy, wherein about 50 mg to about 150 mg of an anti-IL-23 antibody is subcutaneously administered to the subject once at week 0, once at week 4, and once every 8 weeks (q8w) thereafter, wherein the antibody comprises a heavy chain variable region and a light chain variable region, the heavy chain variable region comprising a complementarity determining region heavy chain 1 (CDRH1) amino acid sequence of SEQ ID NO: 1, a CDRH2 of SEQ ID NO: 2, and a CDRH3 of SEQ ID NO: 3; and the light chain variable region comprising a complementarity determining region light chain 1 (CDRL1) amino acid sequence of SEQ ID NO: 4, a CDRL2 of SEQ ID NO: 5, and a CDRL3 of SEQ ID NO: 6, and wherein the subject has at least one psoriatic plaque of ≥2 cm diameter or nail changes consistent with psoriasis or documented history of plaque psoriasis before the treatment, and the subject achieves at least a 20% improvement in the American College of Rheumatology core set disease index (ACR20).
16. The use of embodiment 15, wherein the antibody comprises the heavy chain variable region of the amino acid sequence of SEQ ID NO: 7, and the light chain variable region of the amino acid sequence of SEQ ID NO: 8.
17. The use of embodiment 16, wherein the antibody comprises the heavy chain amino acid sequence of SEQ ID NO: 9, and the light chain amino acid sequence of SEQ ID NO: 10.
18. The use of embodiment 15, wherein the antibody is administered at a dose of about 100 mg per administration.
19. The use of embodiments 1 or 15, wherein the ACR20 is achieved following a treatment period of about 24 weeks or about 48 weeks.
20. The use of embodiment 15, wherein the anti-TNF therapy is an anti-TNFα antibody or TNFα non-antibody antagonist.
21. The use of embodiment 20, wherein the anti-TNFα antibody is adalimumab, golimumab, certolizumab pegol therapy, infliximab and/or biosimilars thereto and the TNFα non-antibody antagonist is etanercept and/or biosimilars thereto.
22. The use of embodiment 15, wherein after the treatment the subject further achieves an improvement in a disease activity determined by at least one criteria selected from the group consisting of: a 50% improvement in the American College of Rheumatology core set disease index (ACR50), a 70% improvement in the American College of Rheumatology core set disease index (ACR70), Health Assessment Questionnaire Disability Index (HAQ-DI), Investigator's Global Assessment (IGA), Disease Activity Score 28 (DAS28) C-reactive protein (CRP), resolution of enthesitis, resolution of dactylitis, Leeds enthesitis index (LEI), dactylitis assessment score, Short Form Health survey (SF-36) in the mental and physical component summary (MCS and PCS), achievement of minimal disease activity (MDA), very low disease activity (VLDA), Bath Ankylosing Spondylitis Disease Activity Index (BASDAI), GRAppa Composite score (GRACE), Psoriatic ArthritiS Disease Activity Score (PASDAS), modified Composite Psoriatic Disease Activity Index (mCPDAI), Psoriatic Area and Severity Index (PAST), Dermatology Life Quality Index (DLQI), Functional Assessment of Chronic Illness Therapy (FACIT), and Patient-Reported Outcomes Measurement Information System-29 (PROMIS-29).

23. The use of embodiment 15, wherein the subject further achieves at least a 50% improvement in the American College of Rheumatology core set disease index (ACR50) after the treatment.

24. The use of embodiment 15, wherein the subject further achieves an improvement in the Health Assessment Questionnaire Disability Index (HAQ-DI) following a treatment period of at least about 24 weeks or about 48 weeks.

25. The use of embodiment 15, wherein the subject further achieved an improvement in Disease Activity Score 28 (DAS28) C-reactive protein (CRP) following a treatment period of at least about 24 weeks or at least about 48 weeks.

26. The use of embodiment 15, wherein the subject further achievs Investigator's Global Assessment (IGA) of 0 (clear) or 1 (minimal), or 2 or more grade reduction in the IGA, following a treatment period of at least about 24 weeks, wherein the subject has 3% or more body surface area (BSA) psoriatic involvement and an IGA score of 2 or more at the baseline before the treatment 27. The use of embodiment 1, wherein the subject has had inadequate response to a standard therapy for the PsA.

28. The use of embodiment 27, wherein the subject is also administered with the standard therapy during the treatment.

29. A pharmaceutical composition of an anti-IL-23 antibody for use in treating psoriastic arthritis in a subject in need thereof having showed an inadequate response to treatment with an anti-TNF therapy, comprising:
   a. an antibody comprising: (i) a heavy chain variable region and a light chain variable region, the heavy chain variable region comprising: a complementarity determining region heavy chain 1 (CDRH1) amino acid sequence of SEQ ID NO:1; a CDRH2 amino acid sequence of SEQ ID NO:2; and a CDRH3 amino acid sequence of SEQ ID NO:3; and the light chain variable region comprising: a complementarity determining region light chain 1 (CDRL1) amino acid sequence of SEQ ID NO:4; a CDRL2 amino acid sequence of SEQ ID NO:5; and a CDRL3 amino acid sequence of SEQ ID NO:6; (ii) a heavy chain variable region of the amino acid sequence of SEQ ID NO:7 and a light chain variable region of the amino acid sequence of SEQ ID NO:8; or (iii) a heavy chain of the amino acid sequence of SEQ ID NO:9 and a light chain of the amino acid sequence of SEQ ID NO:10; and
   b. packaging comprising one or more drug product label elements including data from a randomized, double-blind, placebo-controlled, clinical study in adult men and women with moderately to severely active psoriatic arthritis with inadequate response to anti-TNF therapy.

30. A method of selling a drug product comprising guselkumab, comprising: manufacturing guselkumab; promoting that a therapy comprising guselkumab is safe and effective for treatment of a subject with active psoriatic arthritis having showed an inadequate response to treatment with an anti-TNF therapy, wherein performing the steps a) and b) results in a health care professional (HCP) to purchase the drug product; thereby selling the drug product.

Sequence List:

| SEQ ID NO: | Description | Sequence |
|---|---|---|
| 1 | HCDR1 | NYWIG |
| 2 | HCDR2 | IIDPSNSYTR YSPSFQG |
| 3 | HCDR3 | WYYKPFDV |
| 4 | LCDR1 | TGSSSNIGSG YDVH |
| 5 | LCDR2 | GNSKRPS |
| 6 | LCDR3 | ASWTDGLSLV V |
| 7 | VH | EVQLVQSGAE VKKPGESLKI SCKGSGYSFS NYWIGWVRQM PGKGLEWMGI IDPSNSYTRY SPSFQGQVTI SADKSISTAY LQWSSLKASD TAMYYCARWY YKPFDVWGQG TLVTVSS |
| 8 | VL | QSVLTQPPSV SGAPGQRVTI SCTGSSSNIG SGYDVHWYQQ LPGTAPKLLI YGNSKRPSGV PDRFSGSKSG TSASLAITGL QSEDEADYYC ASWTDGLSLV VFGGGTKLTV L |
| 9 | Heavy Chain | EVQLVQSGAE VKKPGESLKI SCKGSGYSFS NYWIGWVRQM PGKGLEWMGI IDPSNSYTRY SPSFQGQVTI SADKSISTAY LQWSSLKASD TAMYYCARWY YKPFDVWGQG TLVTVSSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKKVEPKSC DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSRDELTK NQVSLTCLVK GFYPSDIAVE WESNGQPENN YKTTPPVLDS DGSFFLYSKL TVDKSRWQQG NVFSCSVMHE ALHNHYTQKS LSLSPGK |
| 10 | Light Chain | QSVLTQPPSV SGAPGQRVTI SCTGSSSNIG SGYDVHWYQQ LPGTAPKLLI YGNSKRPSGV PDRFSGSKSG TSASLAITGL QSEDEADYYC ASWTDGLSLV VFGGGTKLTV LGQPKAAPSV TLFPPSSEEL QANKATLVCL ISDFYPGAVT VAWKADSSPV KAGVETTTPS KQSNNKYAAS SYLSLTPEQW KSHRSYSCQV THEGSTVEKT VAPTECS |

We claim:

1. A method of treating psoriatic arthritis in a subject in need thereof, wherein the subject showed an inadequate response to treatment with an anti-TNFα biologic therapy, wherein the anti-TNFα biologic therapy is an anti-TNFα antibody or TNFα non-antibody antagonist, wherein the anti-TNFα antibody is adalimumab, golimumab, certolizumab pegol therapy, infliximab and/or biosimilars thereto and the TNFα non-antibody antagonist is etanercept and/or biosimilars thereto, the method comprising subcutaneously administering to the subject 50 mg to 150 mg of an anti-IL-23 antibody once every 4 weeks (q4w), wherein the antibody comprises a heavy chain variable region and a light chain variable region, the heavy chain variable region comprising a complementarity determining region heavy chain 1 (CDRH1) amino acid sequence of SEQ ID NO: 1, a CDRH2 of SEQ ID NO: 2, and a CDRH3 of SEQ ID NO: 3; and the light chain variable region comprising a complementarity determining region light chain 1 (CDRL1) amino acid sequence of SEQ ID NO: 4, a CDRL2 of SEQ ID NO: 5, and a CDRL3 of SEQ ID NO: 6, and wherein the subject achieves an improvement in a disease activity determined by at least one criteria selected from the group consisting of a 50% improvement in the American College of Rheumatology core set disease index (ACR50), a 70% improvement in the American College of Rheumatology core set disease index (ACR70), Health Assessment Questionnaire Disability Index (HAQ-DI), Investigator's Global Assessment (IGA), Disease Activity Score 28 (DAS28)C-reactive protein (CRP), resolution of enthesitis, resolution of dactylitis, Leeds enthesitis index (LEI), dactylitis assessment score, Short Form Health survey (SF-36) in the mental and physical component summary (MCS and PCS), achievement of minimal disease activity (MDA), very low disease activity (VLDA), Bath Ankylosing Spondylitis Disease Activity Index (BASDAI), GRAppa Composite score (GRACE), Psoriatic ArthritiS Disease Activity Score (PASDAS), modified Composite Psoriatic Disease Activity Index (mCPDAI), Psoriatic Area and Severity Index (PASI), Dermatology Life Quality Index (DLQI), Functional Assessment of Chronic Illness Therapy (FACIT), and Patient-Reported Outcomes Measurement Information System-29 PROMIS-29).

2. The method of claim 1, wherein the antibody comprises the heavy chain variable region of the amino acid sequence of SEQ ID NO: 7, and the light chain variable region of the amino acid sequence of SEQ ID NO: 8.

3. The method of claim 1, wherein the antibody comprises the heavy chain amino acid sequence of SEQ ID NO: 9, and the light chain amino acid sequence of SEQ ID NO: 10.

4. The method of claim 1, wherein the antibody is administered at a dose of 100 mg per administration.

5. The method of claim 1, wherein achieving the improvement in disease activity ACR20 occurs following a treatment period of 24 weeks.

6. The method of claim 5, wherein the method further comprises maintaining the improvement in disease activity ACR20 from 24 weeks following a treatment period of 48 weeks.

7. The method of claim 1, wherein the method further comprises the subject achieving at least a 20% improvement in the American College of Rheumatology core set index (ACR20).

8. The method of claim 1, wherein the method further comprises the subject achieving at least a 50% improvement in the American College of Rheumatology core set disease index (ACR50) after the treatment.

9. The method of claim 1, wherein the method further comprises the subject achieving an improvement in a Health Assessment Questionnaire Disability Index (HAQ-DI) following a treatment period of at least 24 weeks or 48 weeks.

10. The method of claim 1, wherein the method further comprises the subject achieving an improvement in Disease Activity Score 28 (DAS28)C-reactive protein (CRP) following a treatment period of at least 24 weeks or 48 weeks.

11. The method of claim 1, wherein the method further comprises the subject achieving an Investigator's Global Assessment (IGA) of 0 (clear) or 1 (minimal), or 2 or more grade reduction in the IGA, following a treatment period of at least 24 weeks or at least 48 weeks, wherein the subject has 3% or more body surface area (BSA) psoriatic involvement and an IGA score of 2 or more at the baseline before the treatment.

12. The method of claim 1, wherein the subject has had inadequate response to a standard therapy for the PsA, optionally, the subject is also administered the standard therapy during the treatment.

13. A method of treating psoriatic arthritis in a subject in need thereof, wherein the subject showed an inadequate response to treatment with an anti-TNFα biologic therapy, wherein the anti-TNFα biologic therapy is an anti-TNFα antibody or TNFα non-antibody antagonist, wherein the anti-TNFα antibody is adalimumab, golimumab, certolizumab pegol therapy, infliximab and/or biosimilars thereto and the TNFα non-antibody antagonist is etanercept and/or biosimilars thereto, the method comprising subcutaneously administering to the subject 50 mg to 150 mg of an anti-IL-23 antibody once at week 0, once at week 4, and once every 8 weeks (q8w) thereafter, wherein the antibody comprises a heavy chain variable region and a light chain variable region, the heavy chain variable region comprising a complementarity determining region heavy chain 1 (CDRH1) amino acid sequence of SEQ ID NO: 1, a CDRH2 of SEQ ID NO: 2, and a CDRH3 of SEQ ID NO: 3; and the light chain variable region comprising a complementarity determining region light chain 1 (CDRL1) amino acid sequence of SEQ ID NO: 4, a CDRL2 of SEQ ID NO: 5, and a CDRL3 of SEQ ID NO: 6, and wherein the subject has at least one psoriatic plaque of ≥2 cm diameter or nail changes consistent with psoriasis or documented history of plaque psoriasis before the treatment, and wherein the subject achieves an improvement in a disease activity determined by at least one criteria selected from the group consisting of a 50% improvement in the American College of Rheumatology core set disease index (ACR50), a 70% improvement in the American College of Rheumatology core set disease index (ACR70), Health Assessment Questionnaire Disability Index (HAQ-DI), Investigator's Global Assessment (IGA), Disease Activity Score 28 (DAS28)C-reactive protein (CRP), resolution of enthesitis, resolution of dactylitis, Leeds enthesitis index (LEI), dactylitis assessment score, Short Form Health survey (SF-36) in the mental and physical component summary (MCS and PCS), achievement of minimal disease activity (MDA), very low disease activity (VLDA), Bath Ankylosing Spondylitis Disease Activity Index (BASDAI), GRAppa Composite score (GRACE), Psoriatic Arthritis Disease Activity Score (PASDAS), modified Composite Psoriatic Disease Activity Index (mCPDAI), Psoriatic Area and Severity Index (PASI), Dermatology Life Quality Index (DLQI), Functional Assessment of Chronic Illness Therapy (FACIT), and Patient-Reported Outcomes Measurement Information System-29 (PROMIS-29)).

14. The method of claim 13, wherein the antibody comprises the heavy chain variable region of the amino acid sequence of SEQ ID NO: 7, and the light chain variable region of the amino acid sequence of SEQ ID NO: 8.

15. The method of claim 14, wherein the antibody comprises the heavy chain amino acid sequence of SEQ ID NO: 9, and the light chain amino acid sequence of SEQ ID NO: 10.

16. The method of claim 13, wherein the antibody is administered at a dose of 100 mg per administration.

17. The method of claim 13, wherein achieving the improvement in disease activity occurs following a treatment period of 24 weeks or 48 weeks.

18. The method of claim 13, wherein the method further comprises the subject achieving at least a 20% improvement in the American College of Rheumatology core set disease index (ACR20).

19. The method of claim 13, wherein the method further comprises the subject achieving at least a 50% improvement in the American College of Rheumatology core set disease index (ACR50) after the treatment.

20. The method of claim 13, wherein the method further comprises the subject achieving an improvement in a Health Assessment Questionnaire Disability Index (HAQ-DI) following a treatment period of at least 24 weeks or 48 weeks.

21. The method of claim 13, wherein the method further comprises the subject achieving an improvement in Disease Activity Score 28 (DAS28)C-reactive protein (CRP) following a treatment period of at least 24 weeks or at least 48 weeks.

22. The method of claim 13, wherein the method further comprises the subject achieving an Investigator's Global Assessment (IGA) of 0 (clear) or 1 (minimal), or 2 or more grade reduction in the IGA, following a treatment period of at least 24 weeks, wherein the subject has 3% or more body surface area (BSA) psoriatic involvement and an IGA score of 2 or more at the baseline before the treatment.

23. The method of claim 1, wherein the subject has had inadequate response to a standard therapy for the PsA.

24. The method of claim 23, wherein the subject is also administered with the standard therapy during the treatment.

25. A method of treating psoriatic arthritis in a subject in need thereof, wherein the subject showed an inadequate response to treatment with an anti-TNFα biologic therapy, wherein the anti-TNFα biologic therapy is an anti-TNFα antibody or TNFα non-antibody antagonist, wherein the anti-TNFα antibody is adalimumab, golimumab, certolizumab pegol therapy, infliximab and/or biosimilars thereto and the TNFα non-antibody antagonist is etanercept and/or biosimilars thereto, the method comprising subcutaneously administering to the subject 100 mg of an anti-IL-23 antibody once at week 0, once at week 4, and every 8 weeks (q8w) thereafter, wherein the antibody comprises a heavy chain variable region and a light chain variable region, the heavy chain variable region comprising a complementarity determining region heavy chain 1(CDRH1) amino acid sequence of SEQ ID NO: 1, a CDRH2 of SEQ ID NO: 2, and a CDRH3 of SEQ ID NO: 3; and the light chain variable region comprising a complementarity determining region light chain 1 (CDRL1) amino acid sequence of SEQ ID NO: 4, a CDRL2 of SEQ ID NO: 5,and a CDRL3 of SEQ ID NO: 6, and wherein the subject achieves an improvement in a disease activity determined by at least one criteria selected from the group consisting of a 50% improvement in the American College of Rheumatology core set disease index (ACR50), a 70% improvement in the American College of Rheumatology core set disease index (ACR70), Health Assessment Questionnaire Disability Index (HAQ-DI), Investigator's Global Assessment (IGA), Disease Activity Score 28 (DAS28) C-reactive protein (CRP), resolution of enthesitis, resolution of dactylitis, Leeds enthesitis index (LEI), dactylitis assessment score, Short Form Health survey (SF-36) in the mental and physical component summary (MCS and PCS), achievement of minimal disease activity (MDA), very low disease activity (VLDA), Bath Ankylosing Spondylitis Disease Activity Index (BASDAI), GRAppa Composite score (GRACE), Psoriatic ArthritiS Disease Activity Score (PASDAS), modified Composite Psoriatic Disease Activity Index (mCPDAI), Psoriatic Area and Severity Index (PASI), Dermatology Life Quality Index (DLQI), Functional Assessment of Chronic Illness Therapy (FACIT), and Patient-Reported Outcomes Measurement Information System-29 (PROMIS-29).

26. The method of claim 25, wherein the antibody comprises the heavy chain variable region of the amino acid sequence of SEQ ID NO: 7, and the light chain variable region of the amino acid sequence of SEQ ID NO: 8.

27. The method of claim 25, wherein the antibody comprises the heavy chain amino acid sequence of SEQ ID NO: 9, and the light chain amino acid sequence of SEQ ID NO: 10.

28. The method of claim 25, wherein achieving the improvement in disease activity occurs following a treatment period of 24 weeks.

29. The method of claim 28, wherein the method further comprises maintaining the improvement in disease activity from 24 weeks following a treatment period of 48 weeks.

30. The method of claim 27, wherein achieving the improvement in disease activity occurs following a treatment period of 24 weeks.

31. The method of claim 30, wherein the method further comprises maintaining the improvement in disease activity from 24 weeks following a treatment period of 48 weeks.

32. The method of claim 3, wherein the antibody is administered at a dose of 100 mg per administration.

33. The method of claim 3, wherein achieving the improvement in disease activity occurs following a treatment period of 24 weeks.

34. The method of claim 33, wherein the method further comprises maintaining the improvement in disease activity from 24 weeks following a treatment period of 48 weeks.

* * * * *